United States Patent
De Silva et al.

(10) Patent No.: US 12,319,742 B1
(45) Date of Patent: Jun. 3, 2025

(54) ANTIBODIES THAT BIND TNFRSF25

(71) Applicant: SHATTUCK LABS, INC., Austin, TX (US)

(72) Inventors: Suresh De Silva, Austin, TX (US); Mahmud Hussain, Austin, TX (US); Anne Lai, Austin, TX (US); Derek Franklin, Austin, TX (US); Taylor Schreiber, Austin, TX (US)

(73) Assignee: SHATTUCK LABS, INC., Austin, TX (US)

( * ) Notice: Subject to any disclaimer, the term of this patent is extended or adjusted under 35 U.S.C. 154(b) by 0 days.

(21) Appl. No.: 19/036,915

(22) Filed: Jan. 24, 2025

Related U.S. Application Data

(60) Provisional application No. 63/720,903, filed on Nov. 15, 2024, provisional application No. 63/706,966, filed on Oct. 14, 2024, provisional application No. 63/700,056, filed on Sep. 27, 2024, provisional application No. 63/677,519, filed on Jul. 31, 2024, provisional application No. 63/570,593, filed on Mar. 27, 2024, provisional application No. 63/624,600, filed on Jan. 24, 2024.

(51) Int. Cl.
| | |
|---|---|
| *C07K 16/00* | (2006.01) |
| *A61K 39/395* | (2006.01) |
| *A61P 1/04* | (2006.01) |
| *A61P 29/00* | (2006.01) |
| *C07K 16/28* | (2006.01) |

(52) U.S. Cl.
CPC .......... *C07K 16/2878* (2013.01); *A61P 1/04* (2018.01); *A61P 29/00* (2018.01); *C07K 2317/24* (2013.01); *C07K 2317/31* (2013.01); *C07K 2317/56* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,083,784 B2 | 8/2006 | Dall'Acqua et al. |
| 7,371,826 B2 | 5/2008 | Presta |
| 7,670,600 B2 | 3/2010 | Dall'Acqua et al. |
| 7,704,497 B2 | 4/2010 | Dall'Acqua et al. |
| 7,785,791 B2 | 8/2010 | Presta |
| 8,088,376 B2 | 1/2012 | Chamberlain et al. |
| 8,394,925 B2 | 3/2013 | Chamberlain et al. |
| 8,546,543 B2 | 10/2013 | Lazar |
| 9,803,023 B2 | 10/2017 | Chamberlain et al. |
| 10,336,818 B2 | 7/2019 | Chamberlain et al. |
| 10,683,359 B2 * | 6/2020 | Schreiber ............... A61P 35/00 |
| 2016/0039912 A1 | 2/2016 | Mimoto et al. |
| 2017/0190781 A1 | 7/2017 | Mills et al. |
| 2018/0312599 A1 | 11/2018 | Schreiber et al. |
| 2018/0319889 A1 | 11/2018 | Croft et al. |
| 2021/0102002 A1 | 4/2021 | Bernett et al. |
| 2022/0112307 A1 | 4/2022 | Chamberlain et al. |
| 2022/0306735 A1 | 9/2022 | Dekosky et al. |

FOREIGN PATENT DOCUMENTS

WO  WO 2015/152430 A1  10/2015

OTHER PUBLICATIONS

Buttó, L. F. et al., "Death-Domain-Receptor 3 Deletion Normalizes Inflammatory Gene Expression and Prevents Ileitis in Experimental Crohn's Disease," *Inflamm Bowel Dis.*, 25.1 (2019): 14-26.
Invitation to pay additional fees issued in International Patent Application No. PCT/IB2025/050833, mailed Mar. 14, 2025.
Ko, S. et al., "Recent Achievements and Challenges in Prolonging the Serum Half-Lives of Therapeutic IgG Antibodies Through Fc Engineering," *BioDrugs*, 35 (2021): 147-157.

* cited by examiner

*Primary Examiner* — Meera Natarajan
(74) *Attorney, Agent, or Firm* — Parker Highlander PLLC

(57) ABSTRACT

Provided herein are antibodies and antibody fragments that bind to human TNFRSF25. The antibodies may be monoclonal and/or biparatopic antibodies and/or single-chain fragment variable (scFv) antibodies. Methods of treating or preventing diseases or disorders associated with inflammation and/or autoimmunity are provided, comprising administering to a patient in need thereof an effective amount of a human TNFRSF25-binding antibody.

17 Claims, 36 Drawing Sheets

Specification includes a Sequence Listing.

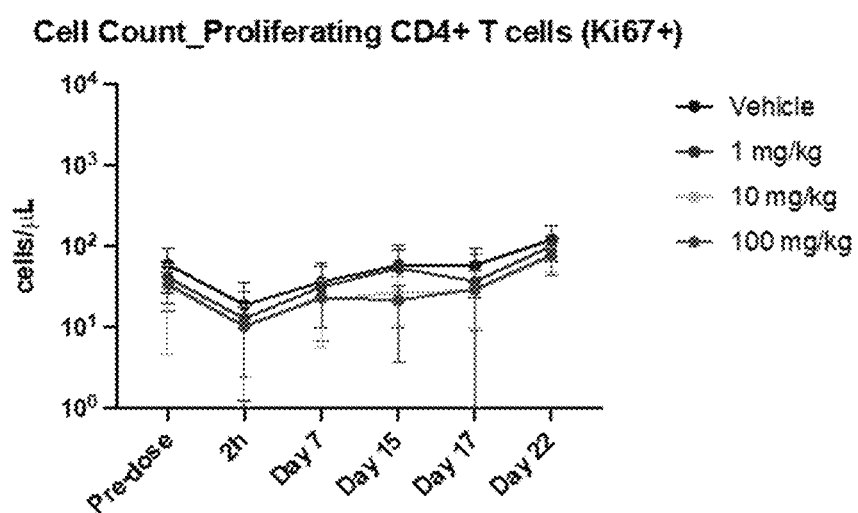
FIG. 18C, continued

ANTIBODIES THAT BIND TNFRSF25

REFERENCE TO RELATED APPLICATIONS

The present application claims the priority benefit of U.S. provisional application No. 63/624,600, filed Jan. 24, 2024, U.S. provisional application No. 63/570,593, filed Mar. 27, 2024, U.S. provisional application No. 63/677,519, filed Jul. 31, 2024, U.S. provisional application No. 63/700,056, filed Sep. 27, 2024, U.S. provisional application No. 63/706,966, filed Oct. 14, 2024, U.S. provisional application No. 63/720,903, filed Nov. 15, 2024, the entire contents of each of which are incorporated herein by reference.

REFERENCE TO A SEQUENCE LISTING

This application contains a Sequence Listing XML, which has been submitted electronically and is hereby incorporated by reference in its entirety. Said Sequence Listing XML, created on Jan. 24, 2025, is named STKLP0006US.xml and is 150,605 bytes in size.

BACKGROUND

1. Field

The present invention relates generally to the fields of medicine and immunology. More particularly, it concerns antibodies that bind to TNFRSF25 and methods of their use.

2. Description of Related Art

Tumor necrosis factor receptor super-family 25 (TNFRSF25) is a member of the tumor necrosis factor receptor super-family (TNFRSF). TNFRSF25 is also known as death receptor 3 (DR3), lymphocyte-associated receptor of death (LARD), APO-3, TRAMP, and WSL-1. TNFRSF25 is expressed on T cells and some other cells including endothelial cells, epithelial cells, osteoblasts, B cells, natural killer T (NKT) cells, and type 2 innate lymphoid cells (ILC2).

TNFRSF25 activation is mediated by tumor necrosis factor (TNF)-like cytokine 1A (TL1A; also known as TNF super family 15; TNFSF15), which is expressed by endothelial cells as well as lymphocyte, plasma cells, dendritic cells, macrophages, monocytes, and synovial fibroblasts. TL1A is also expressed in kidney, lung, prostate, and thymus. TL1A exerts multiple effects on adaptive immune cells by binding TNFRSF25, which affects activation, proliferation, and differentiation of different immune cells, such as helper T cells, regulatory T cells, B cells, as well as production of cytokines, such as interferon-γ (IFN-γ), interleukin (IL)-2, IL-13, tumor necrosis factor alpha (TNF-α), and granulocyte macrophage-colony stimulating factor (GM-CSF). TL1A and TNFRSF25 are also involved in promoting apoptosis and necroptotic cell death.

Binding of TL1A to TNFRSF25 has been related to several inflammatory diseases, such as inflammatory bowel diseases, ulcerative colitis, Crohn's disease, rheumatoid arthritis, psoriasis, atherosclerosis, asthma, multiple sclerosis, primary biliary cirrhosis, systemic lupus erythematosus, and ankylosing spondylitis. Soluble TL1A can be detected in serum and body fluids of patients with T cell-mediated inflammatory autoimmune diseases, such as rheumatoid arthritis, psoriatic arthritis, and ankylosing spondylitis.

Blocking TL1A from binding to TNFRSF25 and/or blocking activation of TNFRSF25 can reduce inflammatory responses. However, soluble TL1A is not constitutively expressed and has a short serum half-life; TL1A expression is tightly regulated by TLR stimulation. As such, anti-TL1A antibodies must act within a short window in order to avoid pathway activation. On the other hand, TNFRSF25 is constitutively expressed. However, previously known anti-TNFRSF25 antibodies are reported to have agonistic activity, which may promote deleterious inflammatory responses such as T-cell proliferation and cytokine production by T cells.

As such, TNFRSF25-binding antibodies that block TL1A from binding to TNFRSF25 and/or block activation of TNFRSF25 without residual agonism of TNRFSF25 are needed.

SUMMARY

Provided herein are monoclonal antibodies and antibody fragments that bind to TNFRSF25, wherein the antibodies or antibody fragments comprise clone-paired heavy and light chain CDR sequences derived from the clone-paired heavy chain and light chain variable sequences of: (a) SEQ ID NO: 50 and SEQ ID NO: 51; (b) SEQ ID NO: 52 and SEQ ID NO: 53; (c) SEQ ID NO: 54 and SEQ ID NO: 55; (d) SEQ ID NO: 94 and SEQ ID NO: 95; (e) SEQ ID NO: 96 and SEQ ID NO: 97; (f) SEQ ID NO: 98 and SEQ ID NO: 99; (g) SEQ ID NO: 100 and SEQ ID NO: 97; (h) SEQ ID NO: 94 and SEQ ID NO: 97; (i) SEQ ID NO: 94 and SEQ ID NO: 99; (j) SEQ ID NO: 96 and SEQ ID NO: 95; (k) SEQ ID NO: 96 and SEQ ID NO: 99; (l) SEQ ID NO: 98 and SEQ ID NO: 95; (m) SEQ ID NO: 98 and SEQ ID NO: 97; (n) SEQ ID NO: 100 and SEQ ID NO: 95; or (o) SEQ ID NO: 100 and SEQ ID NO: 99. For example, the clone-paired heavy and light chain CDR sequences may be: (a) SEQ ID NOs: 7-12; (b) SEQ ID NOs: 13-18; (c) SEQ ID NOs: 19-24; (d) SEQ ID NOs: 30-35; (e) SEQ ID NOs: 36-41; (f) SEQ ID NOs: 42-47; (g) SEQ ID NOs: 7, 8, 77, and 10-12; (h) SEQ ID NOs: 7, 8, 78, 79, 11, and 80; (i) SEQ ID NOs: 81, 8, 79, 83, 11, and 84; (j) SEQ ID NOs: 7-9, 86, 11, and 87; (k) SEQ ID NOs: 7, 8, 77, 79, 11, and 80; (l) SEQ ID NOs: 7, 8, 77, 83, 11, and 84; (m) SEQ ID NOs: 7, 8, 77, 86, 11, and 87; (n) SEQ ID NOs: 7, 8, 78, and 10-12; (o) SEQ ID NOs: 7, 8, 78, 83, 11, and 84; (p) SEQ ID NOs: 7, 8, 78, 86, 11, and 87; (q) SEQ ID NOs: 81, 8, 82, and 10-12; (r) SEQ ID NOs: 81, 8, 82, 79, 11, and 80; (s) SEQ ID NOs: 81, 8, 82, 86, 11, and 87; (t) SEQ ID NOs: 7, 8, 85, and 10-12; (u) SEQ ID NOs: 7, 8, 85, 79, 11, and 80; (v) SEQ ID NOs: 7, 8, 85, 83, 11, and 84; (w) SEQ ID NOs: 30, 31, 88, 33, 34, and 35; (x) SEQ ID NOs: 30, 31, 89, 90, 34, and 80; (y) SEQ ID NOs: 30, 31, 91, 90, 34, and 80; (z) SEQ ID NOs: 30-32, 90, 34, and 80; (a') SEQ ID NOs: 30, 31, 88, 90, 34, and 80; (b') SEQ ID NOs: 30, 31, 88, 90, 34, and 80; (c') SEQ ID NOs: 30, 31, 88, 90, 34, and 80; (d') SEQ ID NOs: 30, 31, 89, and 33-35; (e') SEQ ID NOs: 30, 31, 89, 90, 34, and 80; (f') SEQ ID NOs: 30, 31, 89, 90, 34, and 80; (g') SEQ ID NOs: 30, 31, 91, and 33-35; (h') SEQ ID NOs: 30, 31, 91, 90, 34, and 80; (i') SEQ ID NOs: 30, 31, 91, 90, 34, and 80; (j') SEQ ID NOs: 30-32, 90, 34, and 80; (k') SEQ ID NOs: 30-32, 90, 34, and 80; (l') SEQ ID NOs: 138-143; or (m') SEQ ID NOs: 144-147, 29, and 148. The CDR sequences of the monoclonal antibodies and antibody fragments may comprise one, two, or three substitutions, deletions, and/or insertions relative to the CDR sequences derived from the clone-paired heavy chain and light chain variable sequences of: (a) SEQ ID NO: 50 and SEQ ID NO: 51; (b) SEQ ID NO: 52 and SEQ ID NO: 53; (c) SEQ ID NO: 54 and SEQ ID NO: 55; (d) SEQ ID NO: 94 and SEQ ID NO: 95; (e) SEQ ID NO: 96 and SEQ ID NO: 97; (f) SEQ ID NO: 98 and SEQ ID NO:

99; (g) SEQ ID NO: 100 and SEQ ID NO: 97; (h) SEQ ID NO: 94 and SEQ ID NO: 97; (i) SEQ ID NO: 94 and SEQ ID NO: 99; (j) SEQ ID NO: 96 and SEQ ID NO: 95; (k) SEQ ID NO: 96 and SEQ ID NO: 99; (l) SEQ ID NO: 98 and SEQ ID NO: 95; (m) SEQ ID NO: 98 and SEQ ID NO: 97; (n) SEQ ID NO: 100 and SEQ ID NO: 95; (o) SEQ ID NO: 100 and SEQ ID NO: 99; or (p) SEQ ID NO: 92 and SEQ ID NO: 93. The monoclonal antibodies and antibody fragments may comprise clone-paired heavy chain and light chain variable sequences having, independently, at least 70%, at least 80%, at least 90%, at least 95%, at least 96%, at least 97%, at least 98%, at least 99%, or 100% identity to the sequences of: (a) SEQ ID NO: 50 and SEQ ID NO: 51; (b) SEQ ID NO: 52 and SEQ ID NO: 53; (c) SEQ ID NO: 54 and SEQ ID NO: 55; (d) SEQ ID NO: 94 and SEQ ID NO: 95; (e) SEQ ID NO: 96 and SEQ ID NO: 97; (f) SEQ ID NO: 98 and SEQ ID NO: 99; (g) SEQ ID NO: 100 and SEQ ID NO: 97; (h) SEQ ID NO: 94 and SEQ ID NO: 97; (i) SEQ ID NO: 94 and SEQ ID NO: 99; (j) SEQ ID NO: 96 and SEQ ID NO: 95; (k) SEQ ID NO: 96 and SEQ ID NO: 99; (l) SEQ ID NO: 98 and SEQ ID NO: 95; (m) SEQ ID NO: 98 and SEQ ID NO: 97; (n) SEQ ID NO: 100 and SEQ ID NO: 95; (o) SEQ ID NO: 100 and SEQ ID NO: 99; or (p) SEQ ID NO: 92 and SEQ ID NO: 93. The monoclonal antibodies and antibody fragments may comprise clone-paired heavy and light chain sequences having, independently, at least 70%, at least 80%, at least 90%, at least 95%, at least 96%, at least 97%, at least 98%, at least 99%, or 100% identity to the sequences of: (a) SEQ ID NO: 59 and SEQ ID NO: 60; (b) SEQ ID NO: 61 and SEQ ID NO: 62; (c) SEQ ID NO: 63 and SEQ ID NO: 64; or (d) SEQ ID NO: 127 and SEQ ID NO: 128; (e) SEQ ID NO: 129 and SEQ ID NO: 130; (f) SEQ ID NO: 131 and SEQ ID NO: 132; (g) SEQ ID NO: 133 and SEQ ID NO: 130; (h) SEQ ID NO: 127 and SEQ ID NO: 130; (i) SEQ ID NO: 127 and SEQ ID NO: 132; (j) SEQ ID NO: 129 and SEQ ID NO: 128; (k) SEQ ID NO: 129 and SEQ ID NO: 132; (l) SEQ ID NO: 131 and SEQ ID NO: 128; (m) SEQ ID NO: 131 and SEQ ID NO: 130; (n) SEQ ID NO: 133 and SEQ ID NO: 128; (o) SEQ ID NO: 133 and SEQ ID NO: 132; (p) SEQ ID NO: 151 and SEQ ID NO: 152; or (q) SEQ ID NO: 137 and SEQ ID NO: 128.

Provided herein are monoclonal antibodies and antibody fragments may comprise clone-paired heavy chain and light chain variable sequences having, independently, at least 70%, at least 80%, at least 90%, at least 95%, at least 96%, at least 97%, at least 98%, at least 99%, or 100% identity to the sequences of SEQ ID NO: 48 and SEQ ID NO: 49. The monoclonal antibodies and antibody fragments may comprise clone-paired heavy chain and light chain sequences having, independently, at least 70%, at least 80%, at least 90%, at least 95%, at least %%, at least 97%, at least 98%, at least 99%, or 100% identity to the sequences of (a) SEQ ID NO: 56 and SEQ ID NO: 57; (b) SEQ ID NO: 58 and SEQ ID NO: 57; (c) SEQ ID NO: 134 and SEQ ID NO: 57; (d) SEQ ID NO: 150 and SEQ ID NO: 57; (e) SEQ ID NO: 153 and SEQ ID NO: 57; (f) SEQ ID NO: 151 and SEQ ID NO: 152; or (g) SEQ ID NO: 135 and SEQ ID NO: 57.

The antibody fragments may be a recombinant scFv (single chain fragment variable) antibody, Fab fragment, F(ab')2 fragment, or Fv fragment. The antibodies may be chimeric antibodies, biparatopic antibodies, or bispecific antibodies. The antibodies and antibody fragments may be IgG antibodies or recombinant IgG antibodies or antibody fragments.

The antibody fragment may be a recombinant scFv (single chain fragment variable) antibody comprising clone-paired heavy chain and light chain variable sequences having, independently, at least 70%, at least 80%, at least 90%, at least 95%, at least 96%, at least 97%, at least 98%, at least 99%, or 100% identity to the sequences of: (a) SEQ ID NO: 50 and SEQ ID NO: 51; (b) SEQ ID NO: 52 and SEQ ID NO: 53; (c) SEQ ID NO: 54 and SEQ ID NO: 55; (d) SEQ ID NO: 94 and SEQ ID NO: 95; (e) SEQ ID NO: 96 and SEQ ID NO: 97; (f) SEQ ID NO: 98 and SEQ ID NO: 99; (g) SEQ ID NO: 100 and SEQ ID NO: 97; (h) SEQ ID NO: 94 and SEQ ID NO: 97; (i) SEQ ID NO: 94 and SEQ ID NO: 99; (j) SEQ ID NO: 96 and SEQ ID NO: 95; (k) SEQ ID NO: 96 and SEQ ID NO: 99; (l) SEQ ID NO: 98 and SEQ ID NO: 95; (m) SEQ ID NO: 98 and SEQ ID NO: 97; (n) SEQ ID NO: 100 and SEQ ID NO: 95; (o) SEQ ID NO: 100 and SEQ ID NO: 99; or (p) SEQ ID NO: 92 and SEQ ID NO: 93. The heavy chain and light chain variable sequences may be connected by a flexible linker, such as, for example, a Gly-Ser linker. The flexible linker may comprise or consist of the sequence of GGRGSGGGGSGSGGS (SEQ ID NO: 101) or GGGGSGGGGSGGGGS (SEQ ID NO: 102). The antibody fragment may be a recombinant scFv (single chain fragment variable) antibody comprising or consisting of a sequence having at least 70%, at least 80%, at least 90%, at least 95%, at least 96%, at least 97%, at least 98%, at least 99%, or 100% identity to the sequence of any one of SEQ ID NOs: 103-126.

The antibodies or antibody fragments may bind to TNFRSF25 with a $K_D$ of 50 nM or lower, 10 nM or lower, 5 nM or lower, 1 nM or lower, 0.75 nM or lower, 0.5 nM or lower, 0.1 nM or lower, 75 pM or lower, 50 pM or lower, 25 pM or lower, 10 pM or lower, 7.5 pM or lower, or 5 pM or lower, as measured by surface plasmon resonance or biolayer interferometry.

Provided herein are biparatopic antibodies comprising a first binding part that binds to a first epitope of human TNFRSF25 and a second binding part that binds to a second epitope of human TNFRSF25, wherein the first binding part comprises clone-paired heavy and light chain CDR sequences derived from the clone-paired heavy chain and light chain variable sequences of SEQ ID NO: 48 and SEQ ID NO: 49, and wherein the second binding part comprises clone-paired heavy and light chain CDR sequence derived from the clone-paired heavy chain and light chain variable sequences of (a) SEQ ID NO: 50 and SEQ ID NO: 51; (b) SEQ ID NO: 52 and SEQ ID NO: 53; or (c) SEQ ID NO: 54 and SEQ ID NO: 55. The first binding part may comprise clone-paired heavy and light chain CDR sequences of: (a) SEQ ID NOs: 1-6 or (b) SEQ ID NOs: 25-29 and 6, and the second binding part may comprise clone-paired heavy and light chain CDR sequences of: (a) SEQ ID NOs: 7-12; (b) SEQ ID NOs: 13-18; (c) SEQ ID NOs: 19-24; (d) SEQ ID NOs: 30-35; (e) SEQ ID NOs: 36-41; or (f) SEQ ID NOs: 42-47. The first binding part may comprise clone-paired heavy chain and light chain variable sequences having, independently, at least 70%, at least 80%, at least 90%, at least 95%, at least 96%, at least 97%, at least 98%, at least 99%, or 100% identity to the sequences of SEQ ID NO: 48 and SEQ ID NO: 49, and the second binding part may comprise clone-paired heavy chain and light chain variable sequences having, independently, at least 70%, at least 80%, at least 90%, at least 95%, at least 96%, at least 97%, at least 98%, at least 99%, or 100% identity to the sequences of: (a) SEQ ID NO: 50 and SEQ ID NO: 51; (b) SEQ ID NO: 52 and SEQ ID NO: 53; or (c) SEQ ID NO: 54 and SEQ ID NO: 55. The first binding part may comprise clone-paired heavy and light chain sequences having, independently, at least 70%, at least 80%, at least 90%, at least 95%, at least 96%, at least 97%, at least 98%, at least 99%, or 100% identity to the sequences of (a) SEQ ID NO: 56 and SEQ ID NO: 57; (b) SEQ ID NO: 58 and SEQ ID NO: 57; (c) SEQ ID NO: 65 and SEQ ID NO: 57; or (d) SEQ ID NO: 136 and SEQ ID NO: 57, and the second binding part may comprise clone-paired heavy and light chain sequences having, independently, at least 70%, at least 80%, at least 90%, at least 95%, at least 96%, at least 97%, at least 98%, at least 99%, or 100% identity to the sequences of: (a) SEQ ID NO: 59 and SEQ ID NO: 60; (b) SEQ ID NO: 61 and SEQ ID NO: 62; (c) SEQ ID NO: 63 and SEQ ID NO: 64; (d) SEQ ID NO: 66 and SEQ ID NO: 60; (e) SEQ ID NO: 67 and SEQ ID NO: 62; or (f) SEQ ID NO: 68 and SEQ ID NO: 64.

Provided herein are isolated nucleic acid molecules encoding the antibody heavy chain variable region, the light chain variable region, the heavy chain, or the light chain of any one of the antibodies provided herein. Provided herein are isolated nucleic acid molecules encoding an scFv provided herein. Also provided herein are expression vectors comprising said nucleic acids.

Provided herein are hybridomas or engineered cells comprising a nucleic acid molecule encoding the antibody heavy chain variable region, the light chain variable region, the heavy chain, or the light chain of any one of the antibodies provided herein. Provided herein are methods of making any one of the antibodies provided herein, the method comprising culturing the hybridoma or engineered cell under conditions that allow expression of the antibody or antibody fragment or biparatopic antibody and optionally isolating the antibody or antibody fragment or biparatopic antibody from the culture.

Provided herein are pharmaceutical formulations comprising any one of the antibodies provided herein.

Provided herein are methods of treating a patient having a disease or disorder associated with inflammation and/or autoimmunity, the method comprising administering to the patient a pharmaceutical formulation comprising any one of the antibodies provided herein. The disease or disorder may be ulcerative colitis, Crohn's disease, rheumatoid arthritis, psoriasis, atherosclerosis, asthma, multiple sclerosis, primary biliary cirrhosis, systemic lupus erythematosus, or ankylosing spondylitis. The administering may preserve epithelial barrier integrity. The administering may protect against intestinal damage, such as, for example, TL1A-mediated intestinal damage.

Any of the antibodies, antibody fragments, or biparatopic antibodies provided herein may be for use in treating or preventing a disease or disorder associated with inflammation and/or autoimmunity in a patient.

Provided herein is the use of an antibody or antibody fragment or biparatopic antibody as provided herein or a pharmaceutical formulation as provided herein, in the manufacture of a medicament for treating or preventing a disease or disorder associated with inflammation and/or autoimmunity.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) TNFRSF25 was precoated on MSD assay plates followed by adding scFv supernatant at 2-fold serial-dilutions followed by detection of the myc tag present on the C-terminus of the scFv's. (FIG. 2B) scFv supernatant were serially diluted and added to an MSD-plate pre-coated with TNFRSF25. Next, TL1A was added to the scFv-TNFRSF25 complex followed by detection of remaining TL1A. The lower the TL1A remains, the higher the blocking activity of a given scFv. Some background blocking by the negative control arose from the matrix effect from the unpurified nature of the scFv supernatant and hence is considered as a background signal.

(FIG. 3A) CD16-mediated NFAT activation. 033-scFv derived anti-TNFRSF25 antibodies were first incubated with CHOK1 cells expressing TNFRSF25 for 1 hr. Antibody-opsonized CHOK1 cells were further incubated with Jurkat cells expressing cell surface Fc receptor CD16A and NFAT-Luciferase reporter gene at 1:4 ratio. Luciferase activity resulting from CD16-mediated NFAT activation was measured after 6 hours using a luminometer. (FIG. 3B) Binding of anti-TNFSF25 containing Fc-silencing mutations to FcγR1 as determined by BLI. Sensorgram represent BLI-trace of the analytes (at 300 nM) as indicated in the legend. (FIG. 3C) SL-061 (and SL-034) have no detectable FcγR1 (CD64) mediated DR3 receptor activation or residual agonistic function. HEK293 cells (either parental or CD64-expressing) were seeded into separate 96-well plates and incubated for 5 hours for the cells to adhere. Subsequently, anti-TNFRSF25 antibodies [32 pM] and an equal number of DR3$^+$ Jurkat-NFkB-Luciferase reporter cells were added to the individual HEK293 cells (parental and CD64$^+$) containing plates and incubated for 5 hours. BioGlo luciferase substrate (Promega) was added in a 1:1 ratio and allowed to incubate at room temperature for 10 minutes. The HEK293 parental and CD64$^+$ cells containing plates were subsequently read on a luminescence plate reader. Data analysis subtracted the parental plate values from the CD64$^+$ plate for each antibody to measure the effect of CD64-mediated crosslinking and activation.

(FIG. 5A) BLI assay was performed using the Octet Red 96e instrument. Streptavidin biosensors were loaded with biotinylated recombinant human TNFRSF25-His tagged (Acro #TN5-H52H3) as the ligand. During the association phase, biosensors were incubated with SL-061 at the concentrations indicated for 600 seconds, followed by a 600-second dissociation phase. Complete kinetic parameters were indeterminable by BLI. (FIG. 5B) SPR was performed on a Biacore 8K instrument. Biotinylated recombinant human TNFRSF25-His tagged (Acro #TN5-H52H3) was loaded on a streptavidin sensor chip SA (Cytiva) at 50 nM, followed by flowing SL-061 at the concentrations indicated for an association phase of 2 min and then for a dissociation phase of 30 min. (FIG. 5C) Binding specificity of SL-033 with recombinant receptors. TNFRSF family proteins TNFR1 or TNFR2, as well as the decoy Receptor, DcR3 was immobilized onto a MSD plate and allowed to bind SL-033 (or a positive control) at various concentrations. Following a washing step, SL-033 was detected using a sulfo-tagged anti-human Fc Antibody (or anti-HIS sulfo-tagged antibody as appropriate for the positive controls). SL-033 showed no detectable binding to the receptors tested.

IL18 stimulation). Human PBMCs were stimulated with IL-12 and IL-18 for 24 hours to upregulate TNFRSF25 expression. After 24 hours, cells were treated with various concentrations of anti-TNFRSF25 antibody with or without TL1A (100 ng/mL). Supernatant was harvested after 48 hours for analysis of IFNγ level by MSD. Dotted line represents IFNγ level produced by PBMCs in the absence of TL1A.

Figure 12:
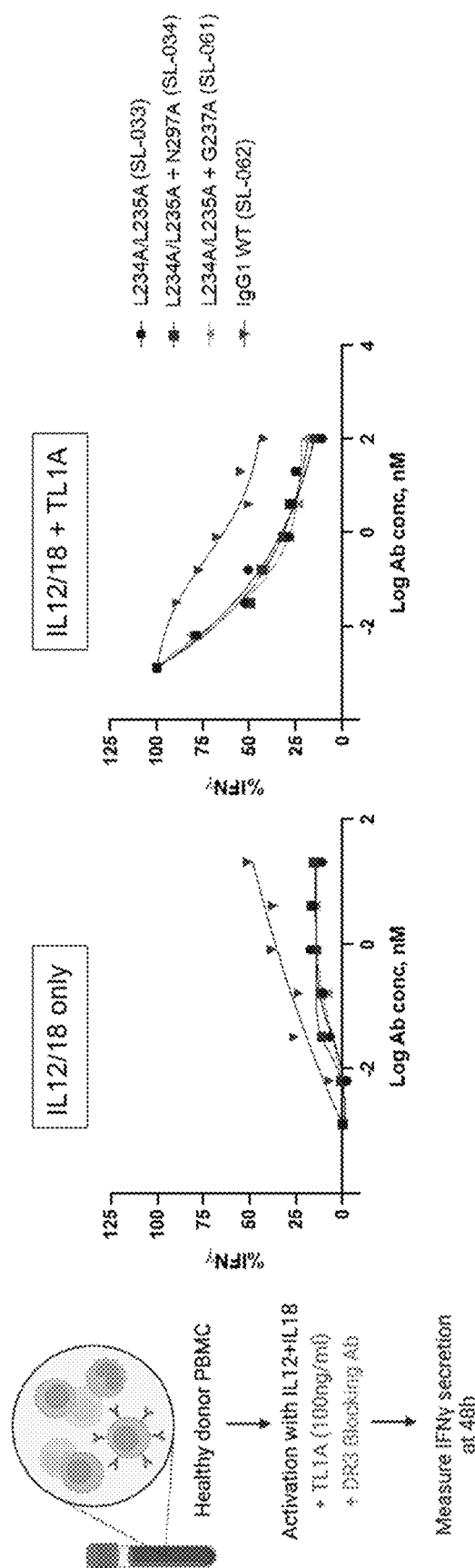

FIG. 12. Enhanced blockade of IFNγ secretion by SL-033 with Fc-silencing mutations (IL12/IL18 stimulation). Human PBMCs were stimulated with IL-12 and IL-18 for 24 hours to upregulate TNFRSF25 expression. After 24 hours, cells were treated with various concentrations of anti-TNFRSF25 with or without TL1A (100 ng/mL). Supernatant was harvested after 48 hours for analysis of IFNγ levels by MSD. IFNγ concentration was normalized to level produced by untreated PBMCs stimulated IL12/18+TL1A.

Figure 13:
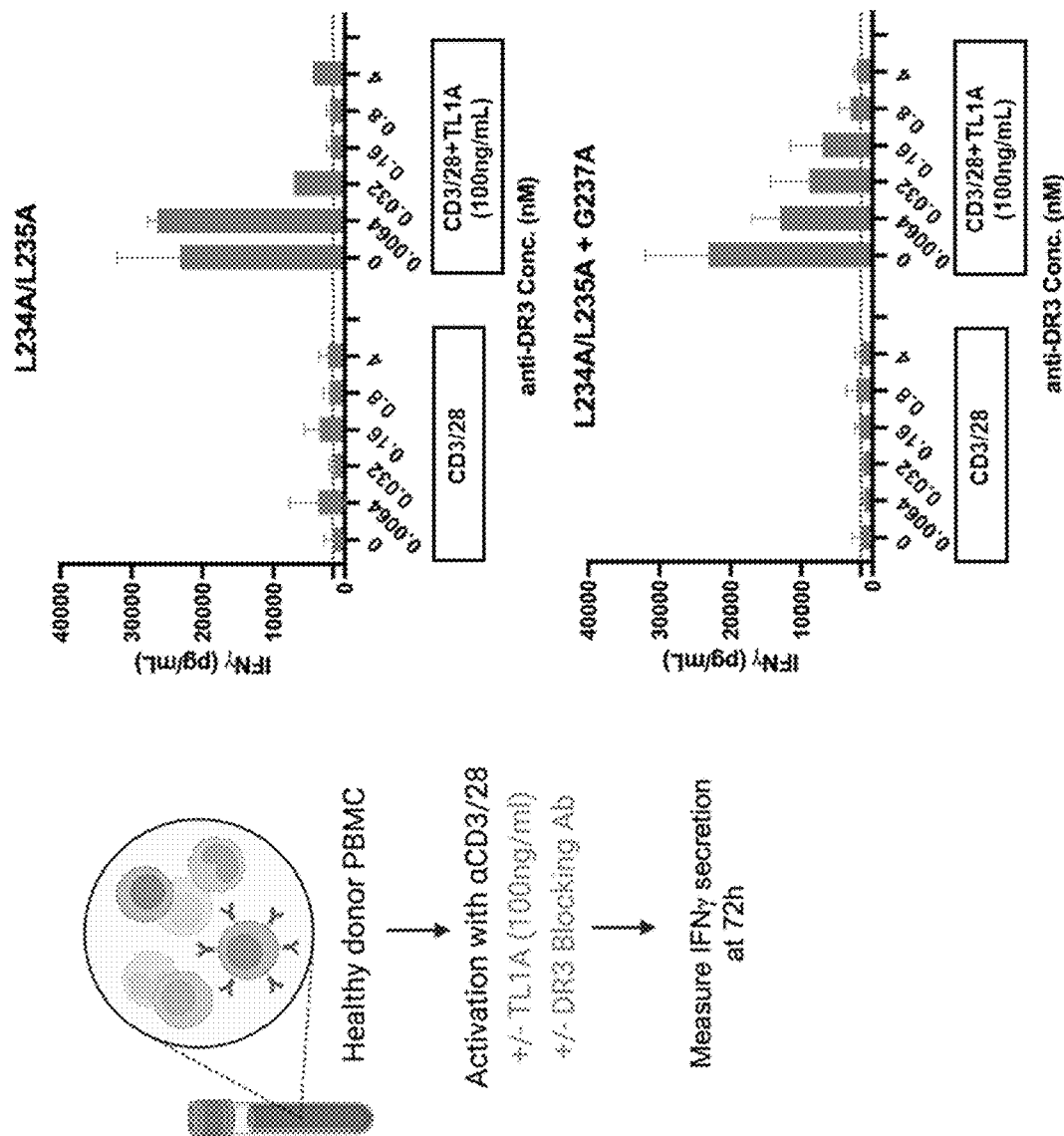

FIG. 13. Comparable IFNγ blocking by SL-033 (L234A/L235A) and SL-061 (L234A/L235A+G237A) under CD3/CD28 stimulation conditions with no evidence of residual agonism. Human PBMCs were stimulated with CD3/CD28 complexes+/−TL1A (100 ng/mL) and treated with various concentrations of anti-TNFRSF25 antibodies. Supernatant was harvested after 72 hours for analysis of IFNγ levels by MSD. Dotted line indicates IFNγ level produced by CD3/CD28 stimulated cells in the absence of TL1A.

Figure 14:
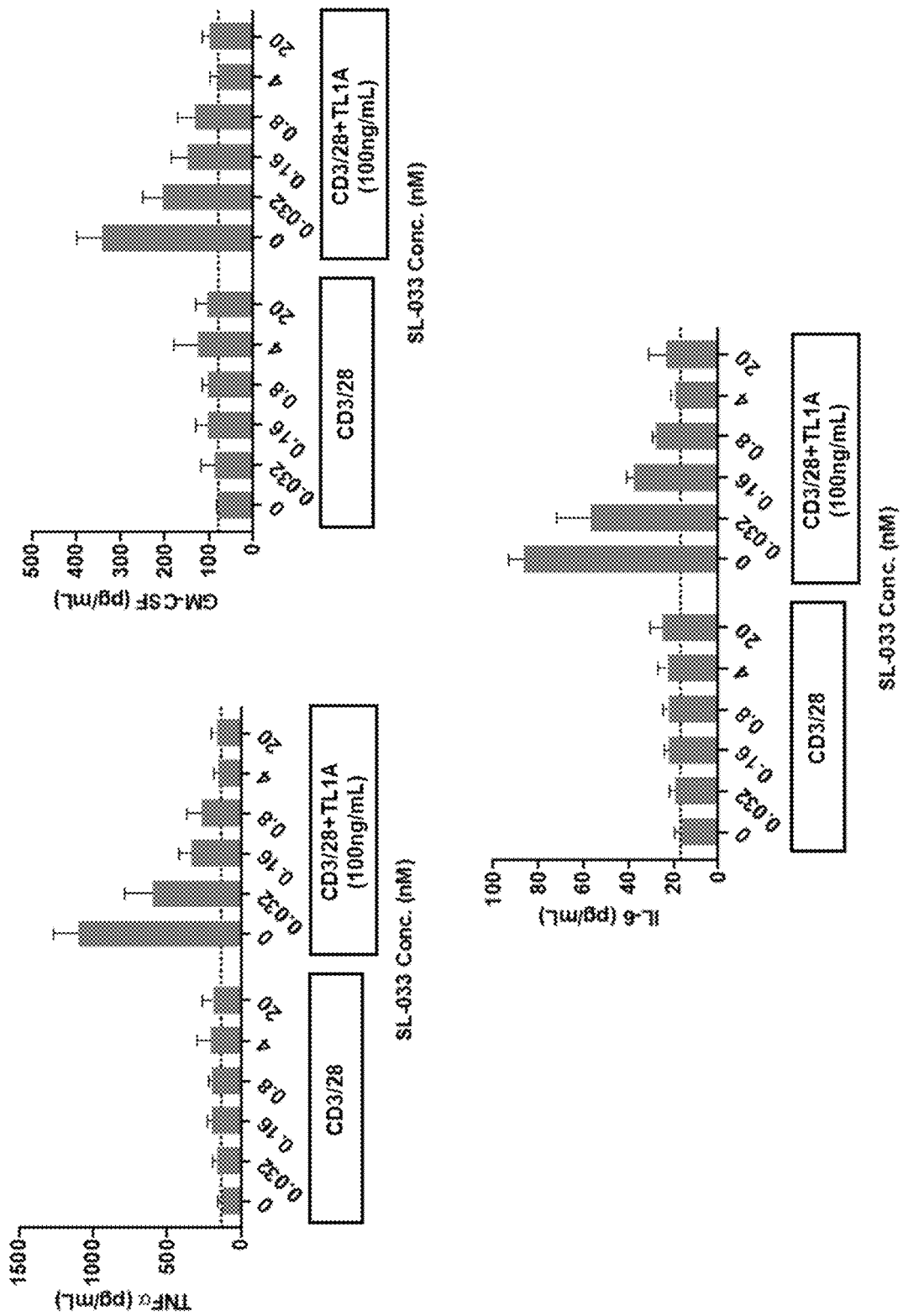

FIG. 14. SL-033 (L234A/L235A) blocks TL1A-induced secretion of TNFα, IL-6, and GM-CSF with no evidence of residual agonism. Human PBMCs were stimulated with CD3/CD28 complexes+/−TL1A (100 ng/mL) and treated with various concentrations of anti-TNFRSF25 antibodies. Supernatant was harvested after 72 hours for analysis of cytokine levels by MSD. Dotted line indicates cytokine levels produced by CD3/CD28 stimulated cells in the absence of TL1A.

Figure 15:
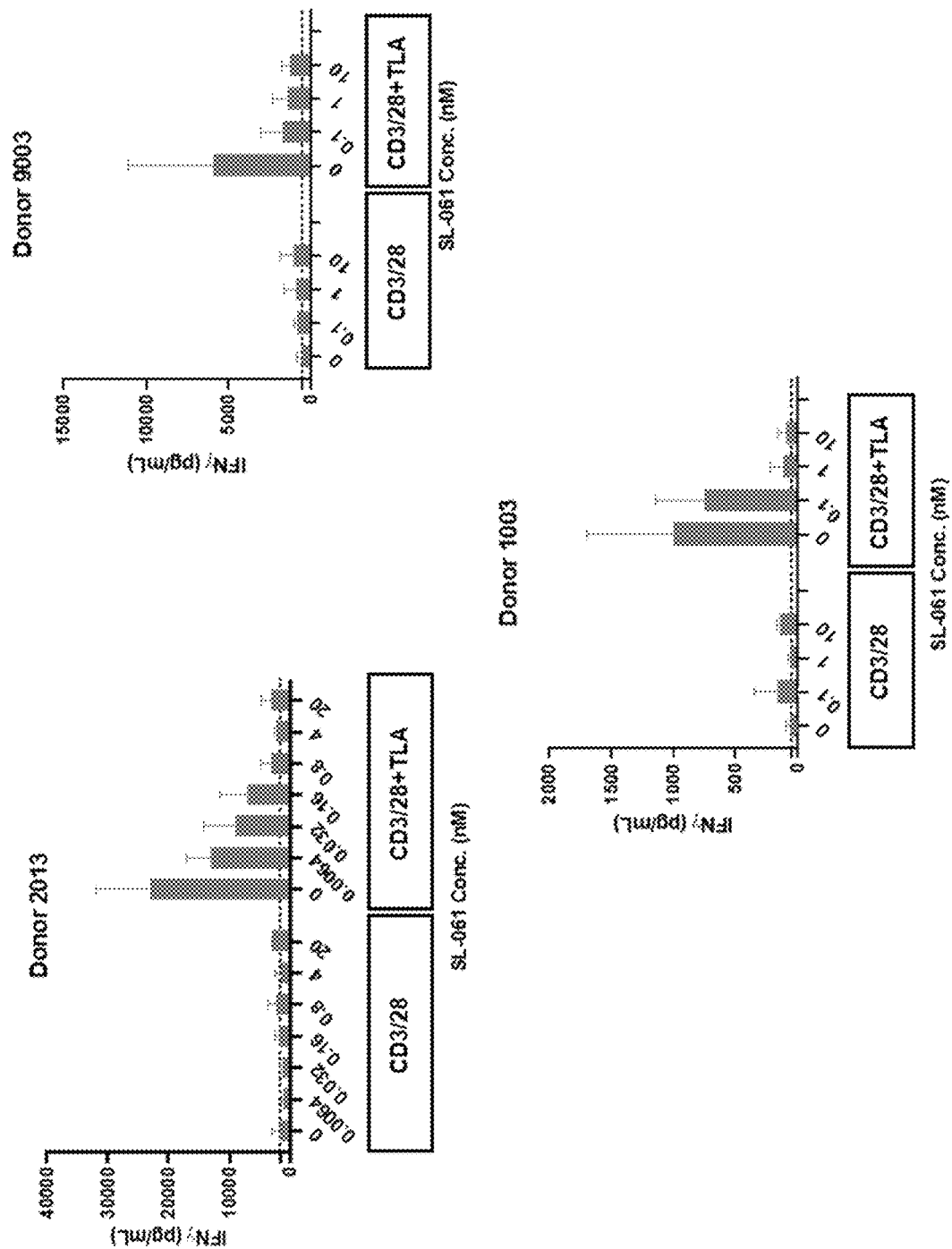

FIG. 15. SL-061 (L234A/L235A+G237A) blocks TL1A-induced IFNγ secretion by lymphocytes stimulated with CD3/CD28 (3 Healthy Donors). Human PBMCs from three individual healthy donors were stimulated with CD3/CD28 complexes+/−TL1A (100 ng/mL) and treated with various concentrations of anti-TNFRSF25 antibody. Supernatant was harvested after 72 hours for analysis of IFNγ levels by MSD. Dotted line indicates IFNγ level produced by CD3/CD28 stimulated cells in the absence of TL1A.

Figure 16:
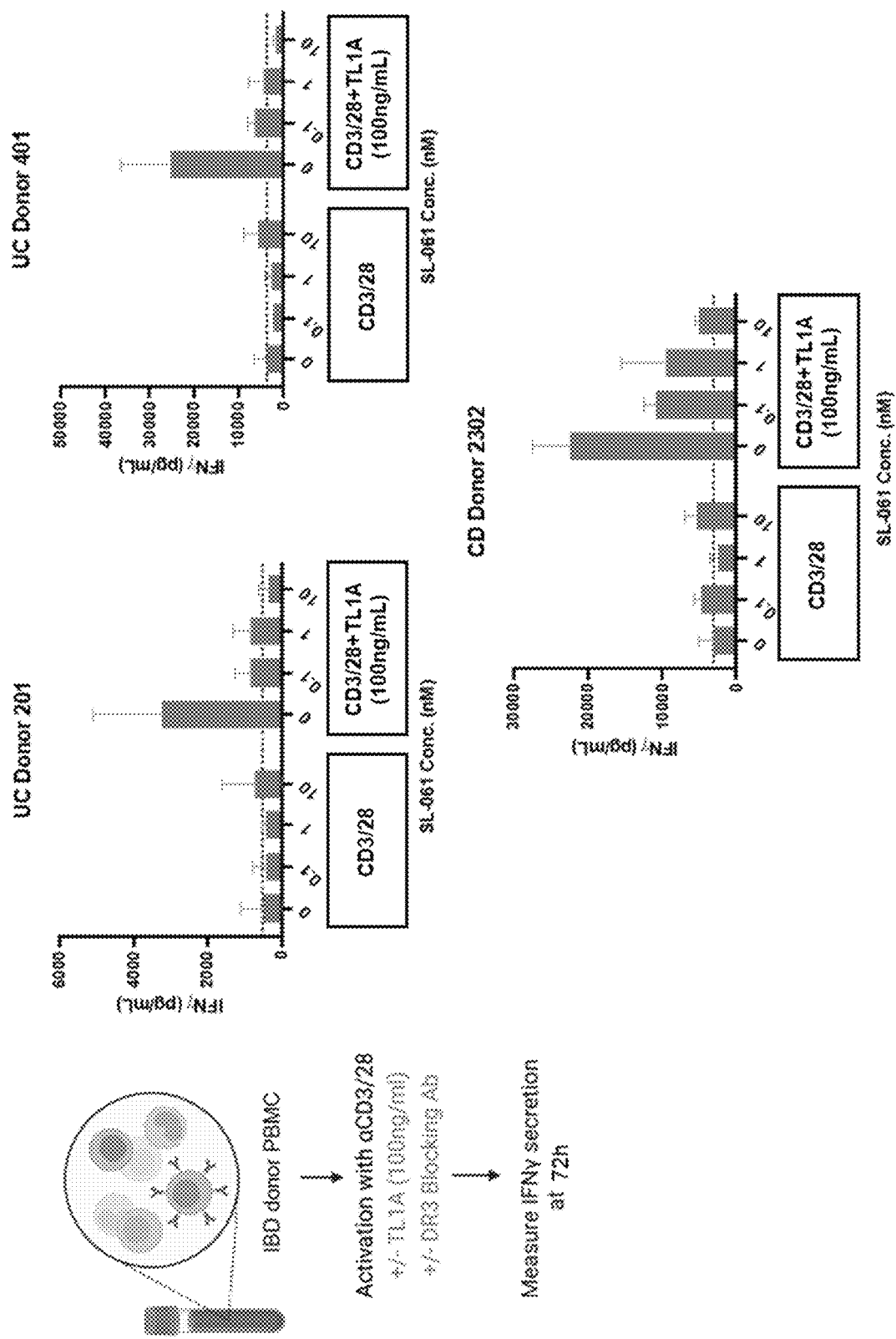

FIG. 16. SL-061 (L234A/L235A+G237A) blocks TL1A-induced IFNγ secretion from IBD patient PBMCs with no evidence of residual agonism. Human PBMCs derived from donors with ulcerative colitis (UC) or Crohn's Disease (CD) were stimulated with CD3/CD28 complexes+/−TL1A (100 ng/mL) and treated with various concentrations of anti-TNFRSF25 antibody. Supernatant was harvested after 72 hours for analysis of IFNγ levels by MSD. Dotted line indicates IFNγ level produced by CD3/CD28 stimulated cells in the absence of TL1A.

Figure 17A:
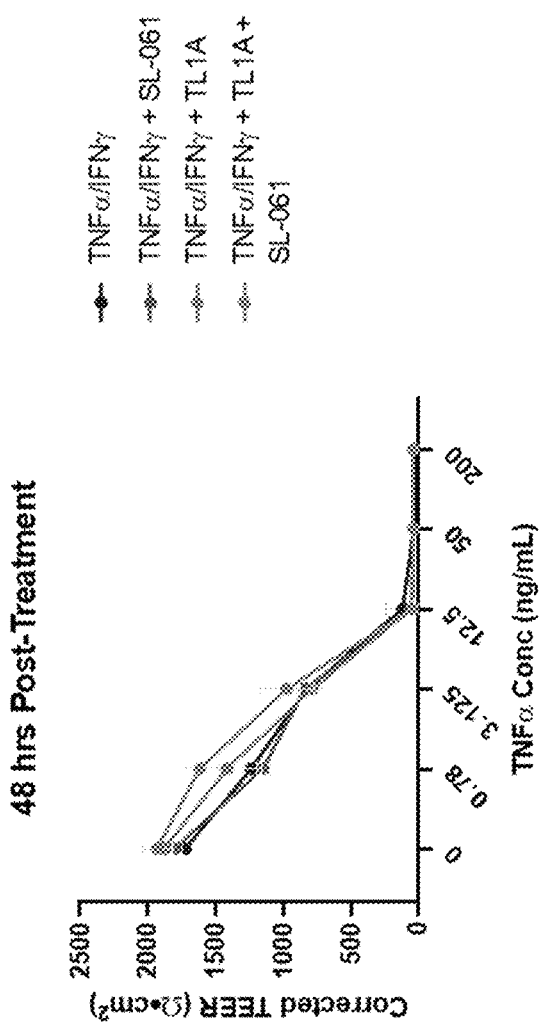

FIG. 17A. Treatment with SL-061 did not result in toxicity to the intestinal epithelial barrier. The RepliGut® intestinal culture system was employed to assess the toxicity of an SL-061 antibody under inflammatory conditions. Human intestinal stem cells were seeded in a transwell system featuring a semi-permeable membrane coated with a biomimetic scaffold composed of a collagen hydrogel, which promotes the differentiation of stem cells into a monolayer of intestinal epithelial cells, closely mimicking the in vivo intestinal epithelium. The cells were cultured according to the RepliGut® protocol, allowing for the formation of a fully differentiated, polarized epithelial monolayer. The resulting epithelial monolayer possessed a population of polarized and differentiated cells, representing a physiologically relevant model system for toxicity evaluation. Once the monolayer was established (6-7 days), the cultured cells were exposed to SL-061 at a fixed concentration of 5 μg/mL in the presence of varying concentrations of pro-inflammatory cytokines, TNFα and IFNγ. These cytokines were added to mimic an inflammatory environment, with their concentrations varied to assess dose-dependent effects. Barrier function was evaluated by measuring transepithelial electrical resistance (TEER) daily throughout the experiment.

Figure 17B:
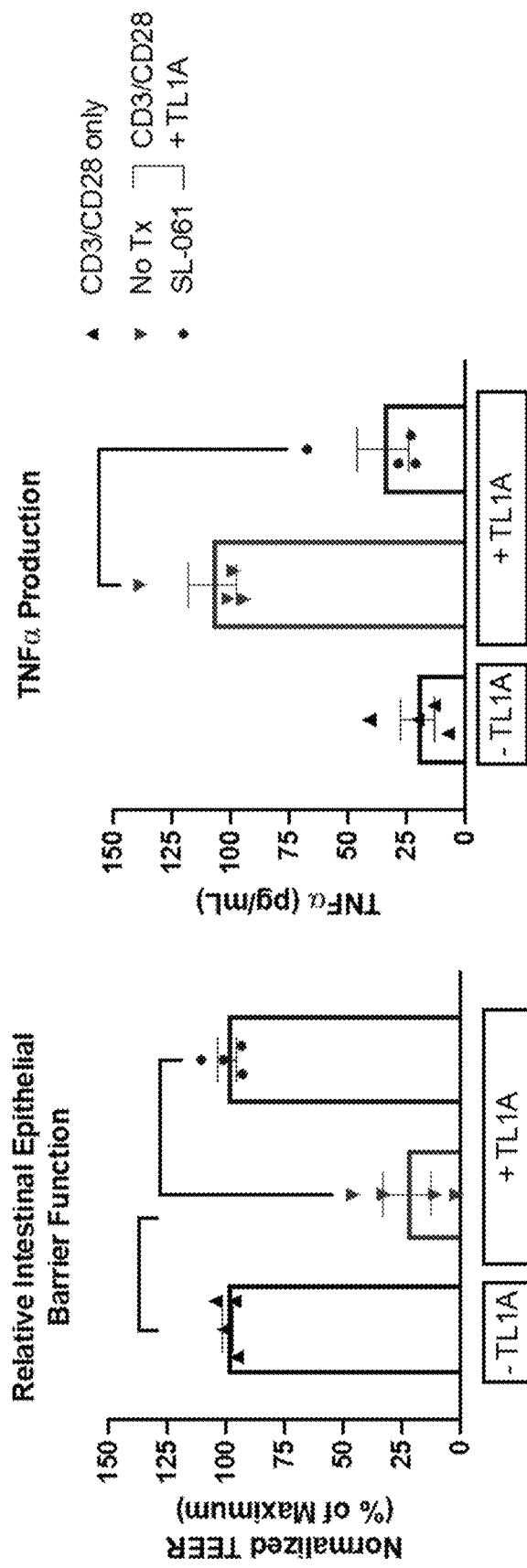

FIG. 17B. SL-061 inhibited TL1A-mediated intestinal epithelial barrier disruption and production of inflammatory cytokines by PBMCs. The effects of SL-061 on intestinal barrier function were evaluated using a co-culture system of pre-activated peripheral blood mononuclear cells (PBMCs) and the RepliGut® intestinal epithelial model. PBMCs derived from a healthy donor were pre-activated with anti-CD3/CD28 complexes and recombinant TL1A to stimulate the production of inflammatory cytokines. After 24 hours, pre-activated PBMCs were added to the basal compartment of the RepliGut® intestinal culture system while SL-061 (5 μg/mL) was applied to both the apical and basal compartments. Intestinal barrier integrity was assessed by daily TEER measurements. TEER values were normalized to the maximum value in each well to account for well-to-well variability.

Figure 18A:
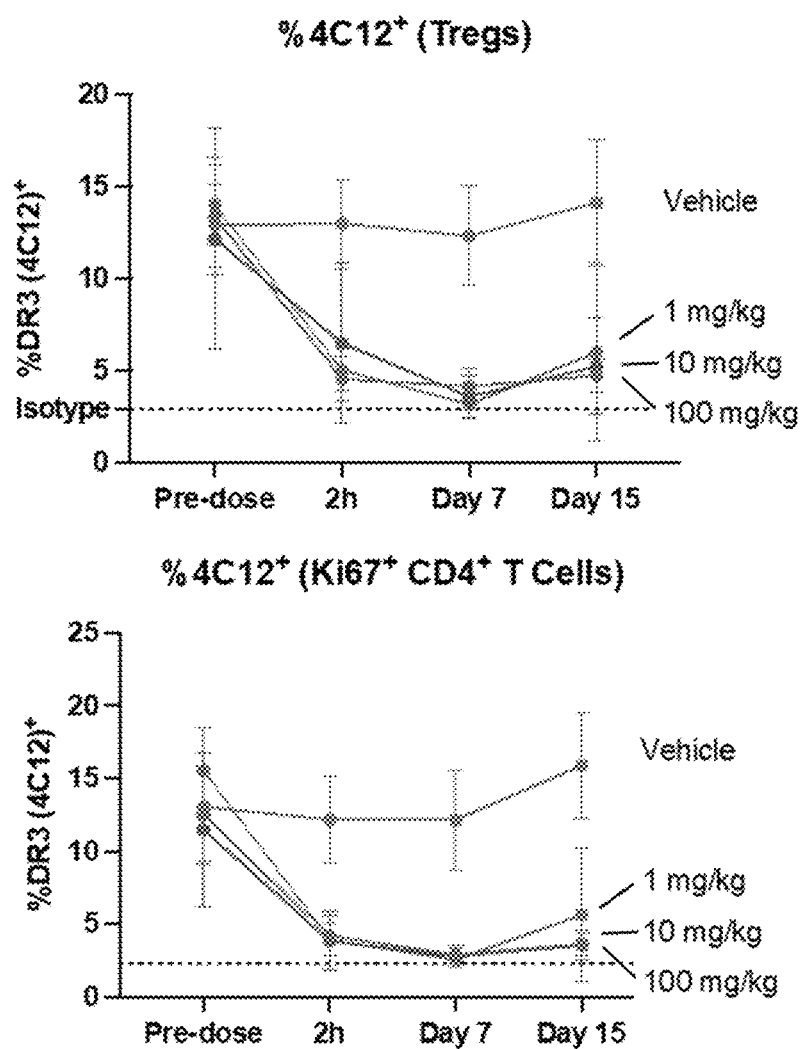
Figure 18B:
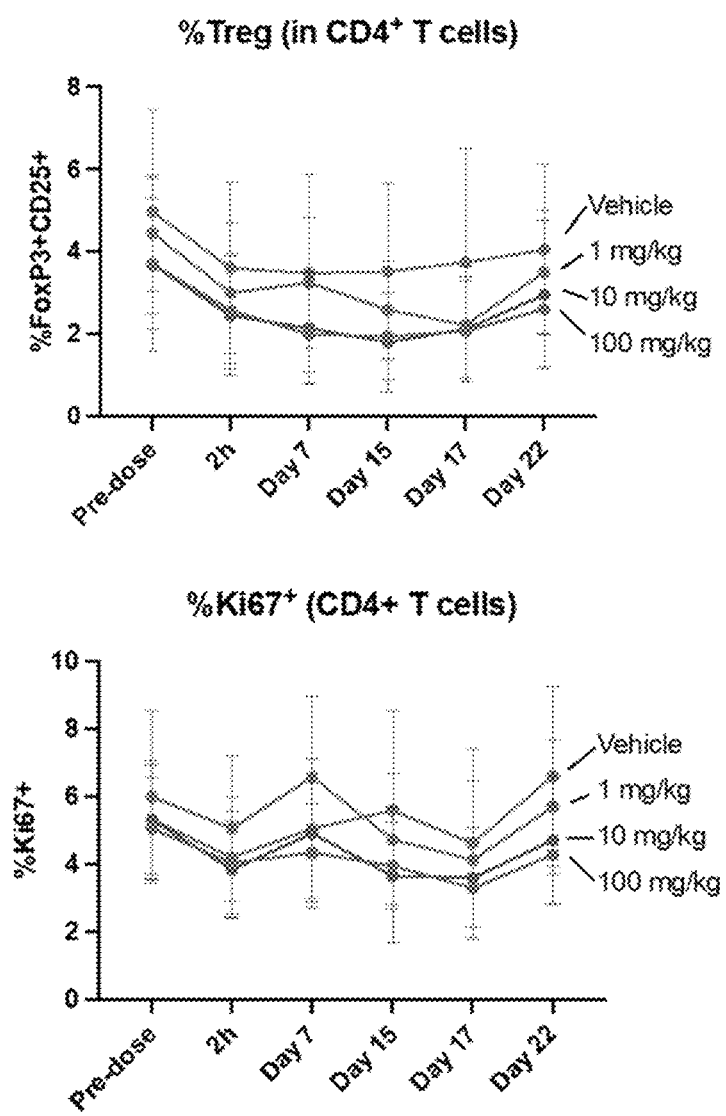
Figure 18C:
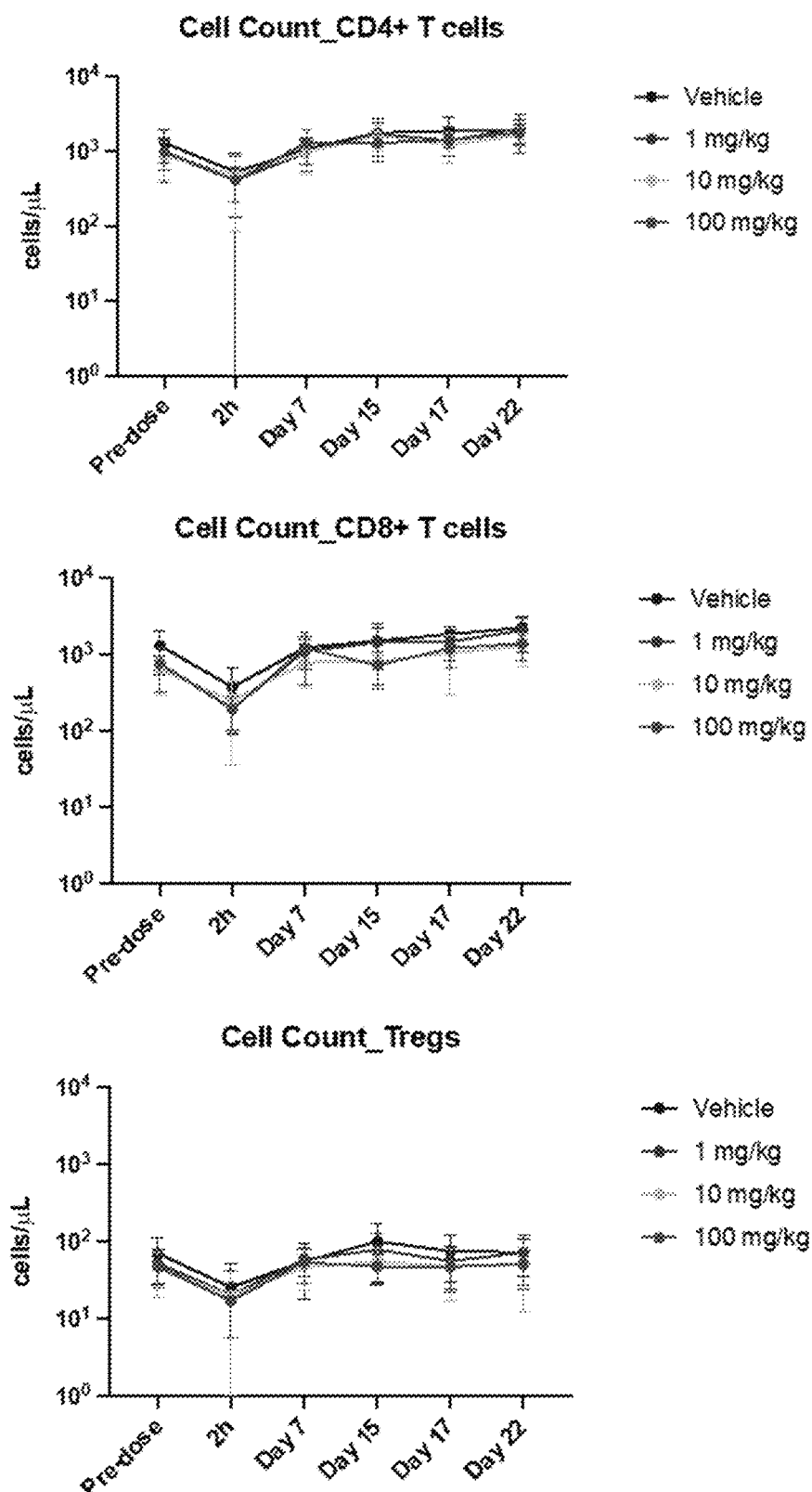

FIGS. 18A-18C. Receptor occupancy and immunophenotyping analysis in non-human primates. FIG. 18A. SL-061 Receptor Occupancy (Indirect): Blockade of anti-TNFRSF25 (clone 4C12) Binding to Tregs and Proliferating CD4+ T Cells (Ki-67+). FIG. 18B. SL-061 treatment did not result in increased frequency of Tregs or proliferating CD4+ T cells. FIG. 18C. SL-061 treatment did not result in expansion of T cells.

Figure 19A:
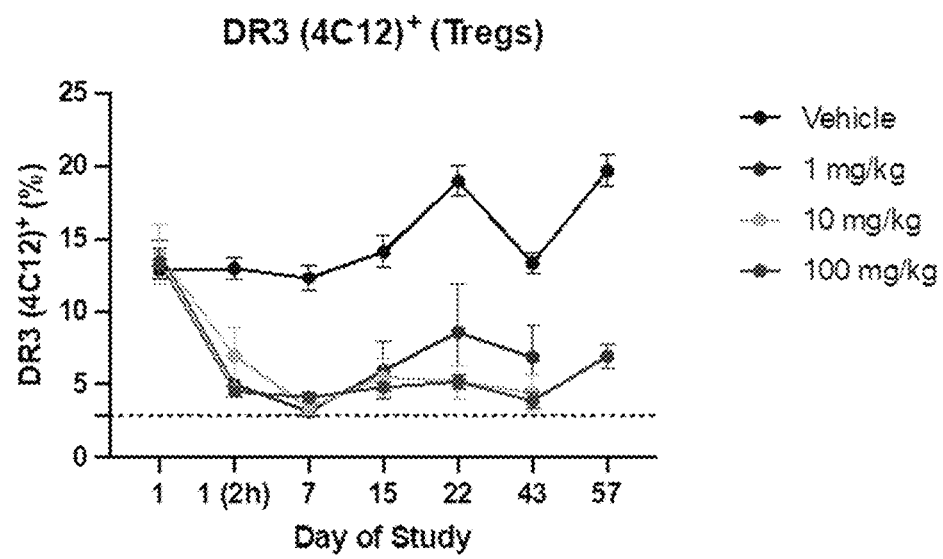
Figure 19B:
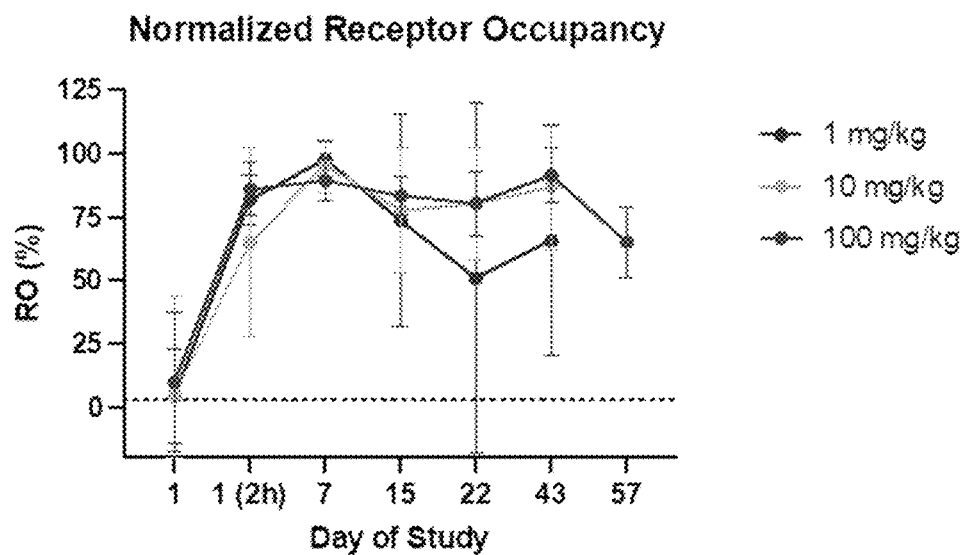

FIGS. 19A-19B. Receptor occupancy. NHPs were administered SL-325 at 1, 10, or 100 mg/kg or vehicle control on Days 1, 15, and 29. (FIG. 19A) The percentage of DR3-positive Tregs was measured by flow cytometry using anti-DR3 antibody (clone 4C12). The dotted line represents background staining level determined using isotype control antibody. (FIG. 19B) Receptor occupancy was calculated by normalizing the DR3+ percentage to vehicle control (set as 100%) and isotype control staining (set as 0%). Data are presented as mean±SD. Timepoints shown are pre-dose and 2 hours post-first dose on Day 1, and Days 7, 15, 22, 43, and 57. The 57-day timepoint includes only recovery animals in vehicle and 100 mg/kg groups.

Figure 20A:
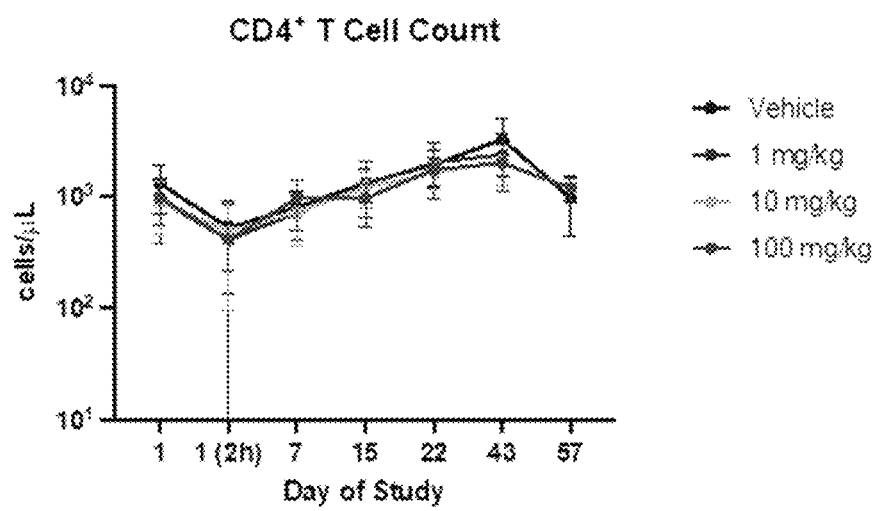
Figure 20B:
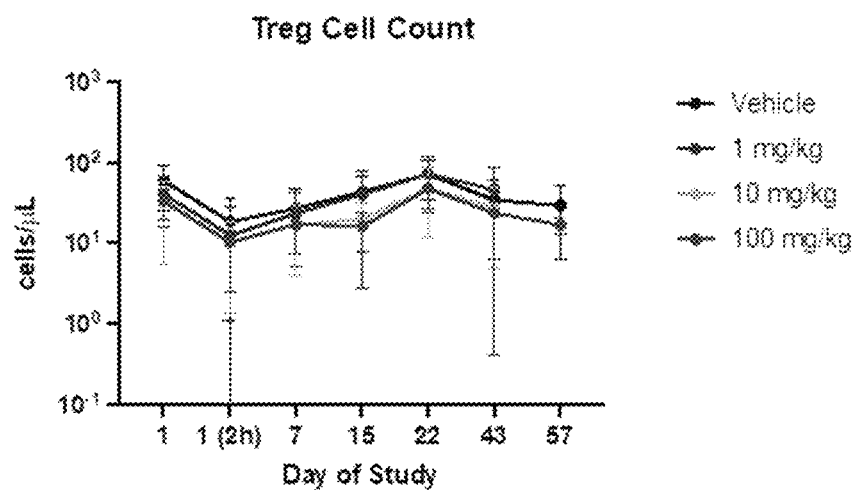
Figure 20C:
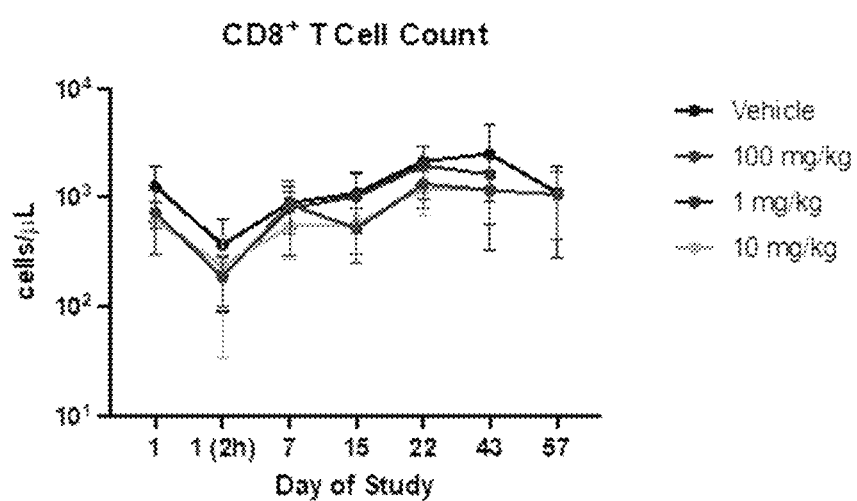

FIGS. 20A-20C. Absolute cell counts. NHPs were administered SL-325 at 1, 10, or 100 mg/kg or vehicle control on Days 1, 15, and 29. Absolute counts of (FIG. 20A) CD4+ T cells, (FIG. 20B) CD8+ T cells, and (FIG. 20C) Tregs were determined by flow cytometry using counting beads. Data are presented as mean±SD. Timepoints shown are pre-dose and 2 hours post-first dose on Day 1, and Days 7, 15, 22, 43, and 57. The 57-day timepoint includes only recovery animals in vehicle and 100 mg/kg groups.

Figure 21A:
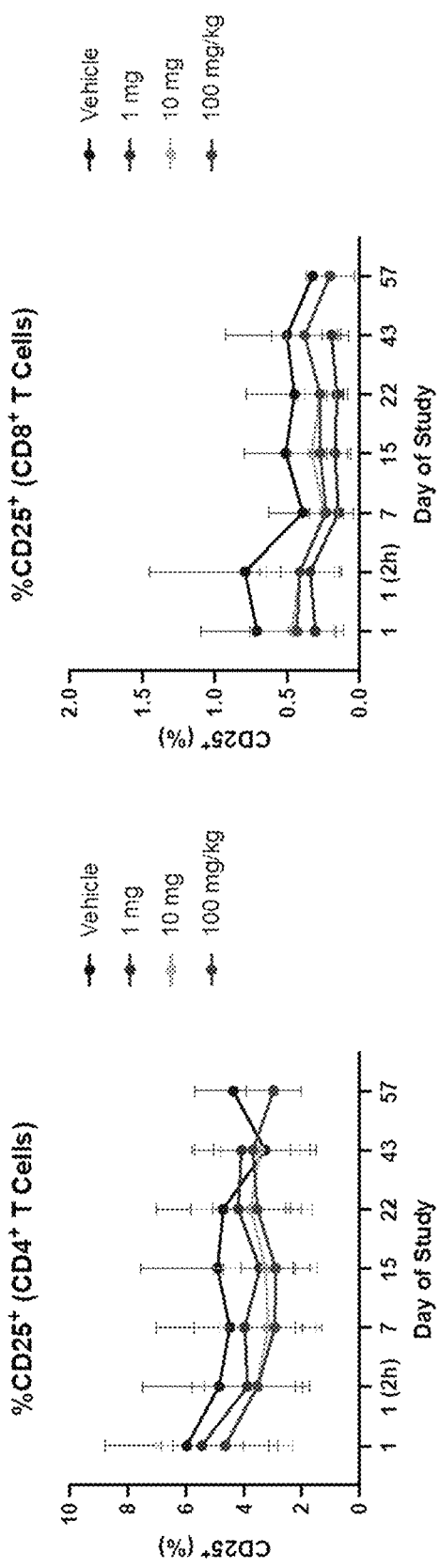
Figure 21B:
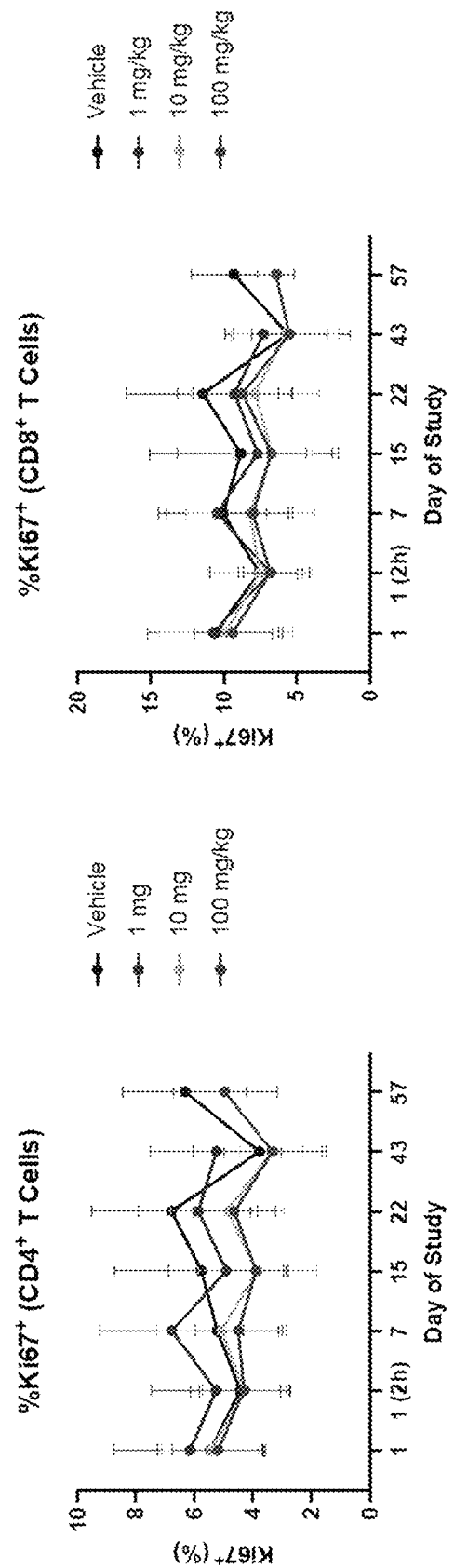
Figure 21C:
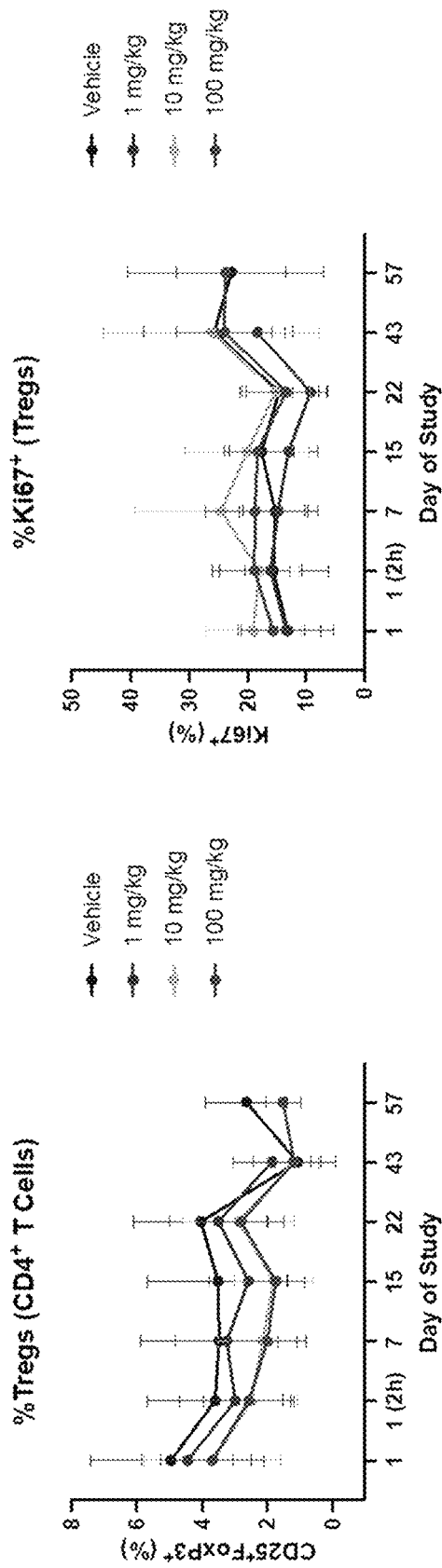

FIGS. 21A-21C. T-Cell Activation and Proliferation. NHPs were administered SL-325 at 1, 10, or 100 mg/kg or vehicle control on Days 1, 15, and 29. (FIG. 21A) The percentage of CD25+ cells among CD4+ T cells (left) and CD8+ T cells (right) was measured to assess T cell activation status. (FIG. 21B) T cell proliferation was evaluated by measuring the percentage of Ki67+ cells in CD4+ T cells (left) and CD8+ T cells (right). (FIG. 21C) The frequency of Tregs within CD4+ T cells (left) and the percentage of Ki67+ Tregs (right) were determined by flow cytometry.

Data are presented as mean±SD. Timepoints shown are pre-dose and 2 hours post-first dose on Day 1, and Days 7, 15, 22, 43, and 57. The 57-day timepoint includes only recovery animals in vehicle and 100 mg/kg groups.

DETAILED DESCRIPTION

Provided herein are monoclonal antibodies and biparatopic antibodies that bind to human TNFRSF25 and have clone-paired CDRs from the heavy and light chains as illustrated in Tables 1 and 2 as well as clone-paired heavy and light chain variable regions as illustrated in Table 3. Furthermore, clone-paired heavy and light chains for the disclosed antibodies are illustrated in Table 4. Exemplary biparatopic antibodies are illustrated in Table 5. Exemplary scFv constructs are illustrated in Table 6. Such antibodies may be produced using methods described herein. These antibodies block TL1A binding to cell-surface TNFRSF25; block TL1A-induced secretion of TNFalpha, IL-6, GM-CSF, and IFNgamma; do not agonize cell-surface TNFRSF25; and/or do not induce internalization of cell-surface TNFRSF25.

TABLE 1

CDRs of heavy and light chain variable sequences of the antibodies as predicted by KABAT numbering.

| Clone | Chain | CDR1 | CDR2 | CDR3 |
|---|---|---|---|---|
| SL-033 | Heavy | GYSAAWN (SEQ ID NO: 1) | RTYYRSKWYNDYAV SVKS (SEQ ID NO: 2) | DYYGSESYYNRGYY YYGMDV (SEQ ID NO: 3) |
|  | Light | RASPGISSALA (SEQ ID NO: 4) | DESSQES (SEQ ID NO: 5) | QQFNDYPLT (SEQ ID NO: 6) |
| SL-034 | Heavy | GYSAAWN (SEQ ID NO: 1) | RTYYRSKWYNDYAV SVKS (SEQ ID NO: 2) | DYYGSESYYNRGYY YYGMDV (SEQ ID NO: 3) |
|  | Light | RASPGISSALA (SEQ ID NO: 4) | DESSQES (SEQ ID NO: 5) | QQFNDYPLT (SEQ ID NO: 6) |
| SL-061 | Heavy | GYSAAWN (SEQ ID NO: 1) | RTYYRSKWYNDYAV SVKS (SEQ ID NO: 2) | DYYGSESYYNRGYY YYGMDV (SEQ ID NO: 3) |
|  | Light | RASPGISSALA (SEQ ID NO: 4) | DESSQES (SEQ ID NO: 5) | QQFNDYPLT (SEQ ID NO: 6) |
| NH24 | Heavy | SYGMS (SEQ ID NO: 7) | YISSSGGHTYYADS VKG (SEQ ID NO: 8) | GSGSFDY (SEQ ID NO: 9) |
|  | Light | QASQDITNYLS (SEQ ID NO: 10) | DASNLET (SEQ ID NO: 11) | QQYDTLPIT (SEQ ID NO: 12) |
| NH46 | Heavy | ELSMH (SEQ ID NO: 13) | GYDPEDGESIFAQK FQG (SEQ ID NO: 14) | DLNWEDAFDV (SEQ ID NO: 15) |
|  | Light | SGSGSNIGNYYVA (SEQ ID NO: 16) | DNNKRPS (SEQ ID NO: 17) | GTWDTSLTAGDIYV (SEQ ID NO: 18) |
| SL-038 | Heavy | NHDMN (SEQ ID NO: 19) | YISSASGLISYADS VRG (SEQ ID NO: 20) | DPAYSGNYALDF (SEQ ID NO: 21) |
|  | Light | TLSSELSSYTIV (SEQ ID NO: 22) | LKSDGSHGKGD (SEQ ID NO: 23) | GAGYTLAGQYGWV (SEQ ID NO: 24) |
| NH24-35 | Heavy | SYGMS (SEQ ID NO: 7) | YISSSGGHTYYADS VKG (SEQ ID NO: 8) | YSGAFDH (SEQ ID NO: 77) |
|  | Light | QASQDITNYLS (SEQ ID NO: 10) | DASNLET (SEQ ID NO: 11) | QQYDTLPIT (SEQ ID NO: 12) |
| NH24-47 | Heavy | SYGMS (SEQ ID NO: 7) | YISSSGGHTYYADS VKG (SEQ ID NO: 8) | YSGAFDR (SEQ ID NO: 78) |
|  | Light | QASQDISNYLS (SEQ ID NO: 79) | DASNLET (SEQ ID NO: 11) | QQYDNLPIT (SEQ ID NO: 80) |

TABLE 1-continued

CDRs of heavy and light chain variable sequences of the antibodies as predicted by KABAT numbering.

| Clone | Chain | CDR1 | CDR2 | CDR3 |
|---|---|---|---|---|
| NH24-72 | Heavy | SYGMN (SEQ ID NO: 81) | YISSSGGHTYYADS VKG (SEQ ID NO: 8) | GQGPFEY (SEQ ID NO: 79) |
|  | Light | QASQDISNYLS (SEQ ID NO: 83) | DASNLET (SEQ ID NO: 11) | QQYDNLPIT (SEQ ID NO: 84) |
| NH24-162 | Heavy | SYGMS (SEQ ID NO: 7) | YISSSGGHTYYADS VKG (SEQ ID NO: 8) | GSGSFDY (SEQ ID NO: 9) |
|  | Light | QASQDISNYLS (SEQ ID NO: 86) | DASNLET (SEQ ID NO: 11) | QQYDNLPIT (SEQ ID NO: 87) |
| NH24-35/47 | Heavy | SYGMS (SEQ ID NO: 7) | YISSSGGHTYYADS VKG (SEQ ID NO: 8) | ARYSGAFDH (SEQ ID NO: 77) |
|  | Light | QASQDISNYLS (SEQ ID NO: 79) | DASNLET (SEQ ID NO: 11) | QQYDNLPIT (SEQ ID NO: 80) |
| NH24-35/72 | Heavy | SYGMS (SEQ ID NO: 7) | YISSSGGHTYYADS VKG (SEQ ID NO: 8) | ARYSGAFDH (SEQ ID NO: 77) |
|  | Light | QASQDISNYLS (SEQ ID NO: 83) | DASNLET (SEQ ID NO: 11) | QQYDNLPIT (SEQ ID NO: 84) |
| NH24-35/162 | Heavy | SYGMS (SEQ ID NO: 7) | YISSSGGHTYYADS VKG (SEQ ID NO: 8) | ARYSGAFDH (SEQ ID NO: 77) |
|  | Light | QASQDISNYLS (SEQ ID NO: 86) | DASNLET (SEQ ID NO: 11) | QQYDNLPIT (SEQ ID NO: 87) |
| NH24-47/35 | Heavy | SYGMS (SEQ ID NO: 7) | YISSSGGHTYYADS VKG (SEQ ID NO: 8) | ARYSGAFDR (SEQ ID NO: 78) |
|  | Light | QASQDITNYLS (SEQ ID NO: 10) | DASNLET (SEQ ID NO: 11) | QQYDTLPIT (SEQ ID NO: 12) |
| NH24-47/72 | Heavy | SYGMS (SEQ ID NO: 7) | YISSSGGHTYYADS VKG (SEQ ID NO: 8) | ARYSGAFDR (SEQ ID NO: 78) |
|  | Light | QASQDISNYLS (SEQ ID NO: 83) | DASNLET (SEQ ID NO: 11) | QQYDNLPIT (SEQ ID NO: 84) |
| NH24-47/162 | Heavy | SYGMS (SEQ ID NO: 7) | YISSSGGHTYYADS VKG (SEQ ID NO: 8) | ARYSGAFDR (SEQ ID NO: 78) |
|  | Light | QASQDISNYLS (SEQ ID NO: 86) | DASNLET (SEQ ID NO: 11) | QQYDNLPIT (SEQ ID NO: 87) |
| NH24-72/35 | Heavy | SYGMN (SEQ ID NO: 81) | YISSSGGHTYYADS VKG (SEQ ID NO: 8) | ARGQGPFEY (SEQ ID NO: 82) |
|  | Light | (SEQ ID NO: 10) | (SEQ ID NO: 11) | QQYDTLPIT (SEQ ID NO: 12) |
| NH24-72/47 | Heavy | SYGMN (SEQ ID NO: 81) | YISSSGGHTYYADS VKG (SEQ ID NO: 8) | ARGQGPFEY (SEQ ID NO: 82) |
|  | Light | QASQDISNYLS (SEQ ID NO: 79) | DASNLET (SEQ ID NO: 11) | QQYDNLPIT (SEQ ID NO: 80) |

TABLE 1-continued

CDRs of heavy and light chain variable sequences of the antibodies as predicted by KABAT numbering.

| Clone | Chain | CDR1 | CDR2 | CDR3 |
|---|---|---|---|---|
| NH24-72/162 | Heavy | SYGMN (SEQ ID NO: 81) | YISSSGGHTYYADS VKG (SEQ ID NO: 8) | ARGQGPFEY (SEQ ID NO: 82) |
| | Light | QASQDISNYLS (SEQ ID NO: 86) | DASNLET (SEQ ID NO: 11) | QQYDNLPIT (SEQ ID NO: 87) |
| NH24-162/35 | Heavy | SYGMS (SEQ ID NO: 7) | YISSSGGHTYYADS VKG (SEQ ID NO: 8) | ARGSGSFDY (SEQ ID NO: 85) |
| | Light | QASQDITNYLS (SEQ ID NO: 10) | DASNLET (SEQ ID NO: 11) | QQYDTLPIT (SEQ ID NO: 12) |
| NH24-162/47 | Heavy | SYGMS (SEQ ID NO: 7) | YISSSGGHTYYADS VKG (SEQ ID NO: 8) | ARGSGSFDY (SEQ ID NO: 85) |
| | Light | QASQDISNYLS (SEQ ID NO: 79) | DASNLET (SEQ ID NO: 11) | QQYDNLPIT (SEQ ID NO: 80) |
| NH24-162/72 | Heavy | SYGMS (SEQ ID NO: 7) | YISSSGGHTYYADS VKG (SEQ ID NO: 8) | ARGSGSFDY (SEQ ID NO: 85) |
| | Light | QASQDISNYLS (SEQ ID NO: 83) | DASNLET (SEQ ID NO: 11) | QQYDNLPIT (SEQ ID NO: 84) |
| SL-061mut213 | Heavy | SYSAAWN (SEQ ID NO: 138) | RTYYRSKWENDYAV SVKS (SEQ ID NO: 139) | DYYGSESYYNRGYY YYGLDV (SEQ ID NO: 140) |
| | Light | RASPSISSALA (SEQ ID NO: 141) | DESSQEG (SEQ ID NO: 142) | QQFNEYPLT (SEQ ID NO: 143) |

TABLE 2

CDRs of heavy and light chain variable sequences of the antibodies as predicted by IMGT numbering.

| Clone | Chain | CDR1 | CDR2 | CDR3 |
|---|---|---|---|---|
| SL-033 | Heavy | GDSVSGYSAA (SEQ ID NO: 25) | TYYRSKWYN (SEQ ID NO: 26) | ARDYYGSESYYNRG YYYYGMDV (SEQ ID NO: 27) |
| | Light | PGISSA (SEQ ID NO: 28) | DES (SEQ ID NO: 29) | QQFNDYPLT (SEQ ID NO: 6) |
| SL-034 | Heavy | GDSVSGYSAA (SEQ ID NO: 25) | TYYRSKWYN (SEQ ID NO: 26) | ARDYYGSESYYNRG YYYYGMDV (SEQ ID NO: 27) |
| | Light | PGISSA (SEQ ID NO: 28) | DES (SEQ ID NO: 29) | QQFNDYPLT (SEQ ID NO: 6) |
| SL-061 | Heavy | GDSVSGYSAA (SEQ ID NO: 25) | TYYRSKWYN (SEQ ID NO: 26) | ARDYYGSESYYNRG YYYYGMDV (SEQ ID NO: 27) |
| | Light | PGISSA (SEQ ID NO: 28) | DES (SEQ ID NO: 29) | QQFNDYPLT (SEQ ID NO: |

TABLE 2-continued

CDRs of heavy and light chain variable sequences of the antibodies as predicted by IMGT numbering.

| Clone | Chain | CDR1 | CDR2 | CDR3 |
|---|---|---|---|---|
| NH24 | Heavy | GFTFSSYG (SEQ ID NO: 30) | ISSSGGHT (SEQ ID NO: 31) | ARGSGSFDY (SEQ ID NO: 32) |
|  | Light | QDITNY (SEQ ID NO: 33) | DAS (SEQ ID NO: 34) | QQYDTLPIT (SEQ ID NO: 35) |
| NH46 | Heavy | GSTVKELS (SEQ ID NO: 36) | YDPEDGES (SEQ ID NO: 37) | ATDLNWEDAFDV (SEQ ID NO: 38) |
|  | Light | GSNIGNYY (SEQ ID NO: 39) | DNN (SEQ ID NO: 40) | GTWDTSLTAGDIYV (SEQ ID NO: 41) |
| SL-038 | Heavy | GFTFSNHD (SEQ ID NO: 42) | ISSASGLI (SEQ ID NO: 43) | ARDPAYSGNYALDE (SEQ ID NO: 44) |
|  | Light | SELSSYT (SEQ ID NO: 45) | LKSDGSH (SEQ ID NO: 46) | GAGYTLAGQYGWV (SEQ ID NO: 47) |
| NH24-35 | Heavy | GFTFSSYG (SEQ ID NO: 30) | ISSSGGHT (SEQ ID NO: 31) | ARYSGAFDH (SEQ ID NO: 88) |
|  | Light | QDITNY (SEQ ID NO: 33) | DAS (SEQ ID NO: 34) | QQYDTLPIT (SEQ ID NO: 35) |
| NH24-47 | Heavy | GFTFSSYG (SEQ ID NO: 30) | ISSSGGHT (SEQ ID NO: 31) | ARYSGAFDR (SEQ ID NO: 89) |
|  | Light | QDISNY (SEQ ID NO: 90) | DAS (SEQ ID NO: 34) | QQYDNLPIT (SEQ ID NO: 80) |
| NH24-72 | Heavy | GFTFSSYG (SEQ ID NO: 30) | ISSSGGHT (SEQ ID NO: 31) | ARGQGPFEY (SEQ ID NO: 91) |
|  | Light | QDISNY (SEQ ID NO: 90) | DAS (SEQ ID NO: 34) | QQYDNLPIT (SEQ ID NO: 80) |
| NH24-162 | Heavy | GFTFSSYG (SEQ ID NO: 30) | ISSSGGHT (SEQ ID NO: 31) | ARGSGSFDY (SEQ ID NO: 32) |
|  | Light | QDISNY (SEQ ID NO: 90) | DAS (SEQ ID NO: 34) | QQYDNLPIT (SEQ ID NO: 80) |
| NH24-35/47 | Heavy | GFTFSSYG (SEQ ID NO: 30) | ISSSGGHT (SEQ ID NO: 31) | ARYSGAFDH (SEQ ID NO: 88) |
|  | Light | QDISNY (SEQ ID NO: 90) | DAS (SEQ ID NO: 34) | QQYDNLPIT (SEQ ID NO: 80) |
| NH24-35/72 | Heavy | GFTFSSYG (SEQ ID NO: 30) | ISSSGGHT (SEQ ID NO: 31) | ARYSGAFDH (SEQ ID NO: 88) |
|  | Light | QDISNY (SEQ ID NO: 90) | DAS (SEQ ID NO: 34) | QQYDNLPIT (SEQ ID NO: 80) |
| NH24-35/162 | Heavy | GFTFSSYG (SEQ ID NO: 30) | ISSSGGHT (SEQ ID NO: 31) | ARYSGAFDH (SEQ ID NO: 88) |
|  | Light | QDISNY (SEQ ID NO: 90) | DAS (SEQ ID NO: 34) | QQYDNLPIT (SEQ ID NO: 80) |

TABLE 2-continued

CDRs of heavy and light chain variable sequences of the antibodies as predicted by IMGT numbering.

| Clone | Chain | CDR1 | CDR2 | CDR3 |
|---|---|---|---|---|
| NH24-47/35 | Heavy | GFTFSSYG (SEQ ID NO: 30) | ISSSGGHT (SEQ ID NO: 31) | ARYSGAFDR (SEQ ID NO: 89) |
| | Light | QDITNY (SEQ ID NO: 33) | DAS (SEQ ID NO: 34) | QQYDTLPIT (SEQ ID NO: 35) |
| NH24-47/72 | Heavy | GFTFSSYG (SEQ ID NO: 30) | ISSSGGHT (SEQ ID NO: 31) | ARYSGAFDR (SEQ ID NO: 89) |
| | Light | QDISNY (SEQ ID NO: 90) | DAS (SEQ ID NO: 34) | QQYDNLPIT (SEQ ID NO: 80) |
| NH24-47/162 | Heavy | GFTFSSYG (SEQ ID NO: 30) | ISSSGGHT (SEQ ID NO: 31) | ARYSGAFDR (SEQ ID NO: 89) |
| | Light | QDISNY (SEQ ID NO: 90) | DAS (SEQ ID NO: 34) | QQYDNLPIT (SEQ ID NO: 80) |
| NH24-72/35 | Heavy | GFTFSSYG (SEQ ID NO: 30) | ISSSGGHT (SEQ ID NO: 31) | ARGQGPFEY (SEQ ID NO: 91) |
| | Light | QDITNY (SEQ ID NO: 33) | DAS (SEQ ID NO: 34) | QQYDTLPIT (SEQ ID NO: 35) |
| NH24-72/47 | Heavy | GFTFSSYG (SEQ ID NO: 30) | ISSSGGHT (SEQ ID NO: 31) | ARGQGPFEY (SEQ ID NO: 91) |
| | Light | QDISNY (SEQ ID NO: 90) | DAS (SEQ ID NO: 34) | QQYDNLPIT (SEQ ID NO: 80) |
| NH24-72/162 | Heavy | GFTFSSYG (SEQ ID NO: 30) | ISSSGGHT (SEQ ID NO: 31) | ARGQGPFEY (SEQ ID NO: 91) |
| | Light | QDISNY (SEQ ID NO: 90) | DAS (SEQ ID NO: 34) | QQYDNLPIT (SEQ ID NO: 80) |
| NH24-162/47 | Heavy | GFTFSSYG (SEQ ID NO: 30) | ISSSGGHT (SEQ ID NO: 31) | ARGSGSFDY (SEQ ID NO: 32) |
| | Light | QDISNY (SEQ ID NO: 90) | DAS (SEQ ID NO: 34) | QQYDNLPIT (SEQ ID NO: 80) |
| NH24-162/72 | Heavy | GFTFSSYG (SEQ ID NO: 30) | ISSSGGHT (SEQ ID NO: 31) | ARGSGSFDY (SEQ ID NO: 32) |
| | Light | QDISNY (SEQ ID NO: 90) | DAS (SEQ ID NO: 34) | QQYDNLPIT (SEQ ID NO: 80) |
| SL-061mut213 | Heavy | GDSVSSYSAA (SEQ ID NO: 144) | TYYRSKWEN (SEQ ID NO: 145) | ARDYYGSESYYNRGYYYYGLDV (SEQ ID NO: 146) |
| | Light | PSISSA (SEQ ID NO: 147) | DES (SEQ ID NO: 29) | QQFNEYPLT (SEQ ID NO: 148) |

TABLE 3

Amino acid sequences of the monoclonal antibody variable regions.

| Clone | Chain | Variable Sequence |
|---|---|---|
| SL-033 | Heavy | QVQLQQSGPGLVKPSQTLSLICAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSS (SEQ ID NO: 48) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIK (SEQ ID NO: 49) |
| SL-034 | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSS (SEQ ID NO: 48) |
| | Light | AIQLTQSPSSLSASVGDRVTITCRASPGISSALAWYQQKPGKAPKLLMY DESSQESGVPSRFSGSGSGIDFTLTISSLQPEDFATYYCQQFNDYPLTF GGGTKVEIK (SEQ ID NO: 49) |
| SL-061 | Heavy | QVQLQQSGPGLVKPSQTLSLICAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSS (SEQ ID NO: 48) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIK (SEQ ID NO: 49) |
| NH24 | Heavy | EVQLVESGGGSVQPGGSLRLSCAASGFTFSSYGMSWIRQAPGKGLEWIS YISSSGGHTYYADSVKGRFTI SRDNAKNSLYLQMNSLRAEDTAVYYCAR GSGSFDYWGQGTLVTVSS (SEQ ID NO: 50) |
| | Light | DIVMTQSPSSLSASVGDRVTITCQASQDITNYLSWYQQKPGKAPKLLIS DASNLETGIPSRFSGSGSGTDFTFTISSLQPEDIATYYCQQYDTLPITF GQGTRLEIK (SEQ ID NO: 51) |
| NH46 | Heavy | QVQLVQSGSEVKKPGASVRVSCKVSGSTVKELSMHWVRQAPGKGLEWMG GYDPEDGESIFAQKFQGRVNMTEDRSTDTAYMELSSLRSEDTAVYYCAT DLNWEDAFDVWGQGTMVTVSS (SEQ ID NO: 52) |
| | Light | QSVLTQPPSVSAAPGQKVTISCSGSGSNIGNYYVAWYQQFPGTAPKLLI YDNNKRPSGIPDRFSGSKSGTSATLGITGLQTGDEADYYCGTWDISLTA GDIYVFGTGTKVTVL (SEQ ID NO: 53) |
| SL-038 | Heavy | EVQLVESGGGLSQPGNSLQLSCEASGFTFSNHDMNWVRQAPGKGLEWVA YISSASGLISYADSVRGRFTISRDNAKNSLFLQMNNLKSEDTAMYYCAR DPAYSGNYALDFWGQGTQVTVSS (SEQ ID NO: 54) |
| | Light | QPVLTQSPSASASLSGSVKLICTLSSELSSYTIVWYQQQPDKAPKYVMY LKSDGSHGKGDIPDRFSGSSSGAHRYLSVSNVQSEDDATYFCGAGYTL AGQYGWVFGSGTKVTVL (SEQ ID NO: 55) |
| NH24-35 | Heavy | EVQLVESGGGSVQPGGSLRLSCAASGFTFSSYGMSWIRQAPGKGLEWVS YISSSGGHTYYADSVKGRFTISRDNAKNSLYLQMNSLRAEDTAVYYCAR YSGAFDHWGQGTLVTVSS (SEQ ID NO: 94) |
| | Light | DIVMTQSPSSLSASVGDRVTITCQASQDITNYLSWYQQKPGKAPKLLIN DASNLETGVPSRFSGSGSGTDFTFTI SSLQPEDIATYYCQQYDTLPITF GQGTRLEIKR (SEQ ID NO: 95) |
| NH24-47 | Heavy | EVQLVESGGGSVQPGGSLRLSCAASGFTFSSYGMSWVRQAPGKGLEWIS YISSSGGHTYYADSVKGRFTI SRDNAKNSLYLQMNSLRAEDTAVYYCAR YSGAFDRWGQGTPVTVSS (SEQ ID NO: 96) |
| | Light | DIVMTQSPSSLSASVGDRVTITCQASQDISNYLSWYQQKPGKAPKLLIS DASNLETGVPSRFSGSGSGTDFTFTI SSLQPEDIATYYCQQYDNLPITF GQGTRLEIKR (SEQ ID NO: 97) |
| NH24-72 | Heavy | EVQLVESGGGSVQPGGSLRLSCAASGFTFSSYGMNWIRQAPGKGLEWIT YISSSGGHTYYADSVKGRFTISRDNAKNSLYLQMNSLRAEDTAVYYCAR GQGPFEYWGQGTLVTVSS (SEQ ID NO: 98) |
| | Light | DIVMTQSPSSLSASVGDRVTITCQASQDISNYLSWYQQKPGKAPKLLIN DASNLETGVPSRFSGSGSGTDFTFTI SSLQPEDIATYYCQQYDNLPITF GQGTRLEIKR (SEQ ID NO: 99) |
| NH24-162 | Heavy | EVQLVESGGGSVQPGGSLRLSCAASGFTFSSYGMSWVRQAPGKGLEWIS YISSSGGHTYYADSVKGQFTI SRDNAKNSLYLQMNSLRAEDTAVYYCAR GSGSFDYWGQGTLVTVSS (SEQ ID NO: 100) |
| | Light | DIVMTQSPSSLSASVGDRVTITCQASQDISNYLSWYQQKPGKAPKLLIS DASNLETGVPSRFSGSGSGTDFTFTI SSLQPEDIATYYCQQYDNLPITF GQGTRLEIKR (SEQ ID NO: 97) |
| NH24-35/47 | Heavy | EVQLVESGGGSVQPGGSLRLSCAASGFTFSSYGMSWIRQAPGKGLEWVS YISSSGGHTYYADSVKGRFTI SRDNAKNSLYLQMNSLRAEDTAVYYCAR YSGAFDHWGQGTLVTVSS (SEQ ID NO: 94) |

TABLE 3-continued

Amino acid sequences of the monoclonal antibody variable regions.

| Clone | Chain | Variable Sequence |
|---|---|---|
| | Light | DIVMTQSPSSLSASVGDRVTITCQASQDI SNYLSWYQQKPGKAPKLLIS DASNLETGVPSRFSGSGSGTDFTFTI SSLQPEDIATYYCQQYDNLPITF GQGTRLEIKR (SEQ ID NO: 97) |
| NH24-35/72 | Heavy | EVQLVESGGGSVQPGGSLRLSCAASGFTFSSYGMSWIRQAPGKGLEWVS YISSSGGHTYYADSVKGRFTI SRDNAKNSLYLQMNSLRAEDTAVYYCAR YSGAFDHWGQGTLVTVSS (SEQ ID NO: 94) |
| | Light | DIVMTQSPSSLSASVGDRVTITCQASQDISNYLSWYQQKPGKAPKLLIN DASNLETGVPSRFSGSGSGTDFTFTISSLQPEDIATYYCQQYDNLPITF GQGTRLEIKR (SEQ ID NO: 99) |
| NH24-47/35 | Heavy | EVQLVESGGGSVQPGGSLRLSCAASGFTFSSYGMSWVRQAPGKGLEWIS YISSSGGHTYYADSVKGRFTISRDNAKNSLYLQMNSLRAEDTAVYYCAR YSGAFDRWGQGTPVTVSS (SEQ ID NO: 96) |
| | Light | DIVMTQSPSSLSASVGDRVTITCQASQDITNYLSWYQQKPGKAPKLLIN DASNLETGVPSRFSGSGSGTDFTFTI SSLQPEDIATYYCQQYDTLPITF GQGTRLEIKR (SEQ ID NO: 95) |
| NH24-47/72 | Heavy | EVQLVESGGGSVQPGGSLRLSCAASGFTFSSYGMSWVRQAPGKGLEWIS YISSSGGHTYYADSVKGRFTI SRDNAKNSLYLQMNSLRAEDTAVYYCAR YSGAFDRWGQGTPVTVSS (SEQ ID NO: 96) |
| | Light | DIVMTQSPSSLSASVGDRVTITCQASQDISNYLSWYQQKPGKAPKLLIN DASNLETGVPSRFSGSGSGTDFTFTISSLQPEDIATYYCQQYDNLPITF GQGTRLEIKR (SEQ ID NO: 99) |
| NH24-72/35 | Heavy | EVQLVESGGGSVQPGGSLRLSCAASGFTFSSYGMNWIRQAPGKGLEWIT YISSSGGHTYYADSVKGRFTI SRDNAKNSLYLQMNSLRAEDTAVYYCAR GQGPFEYWGQGTLVTVSS (SEQ ID NO: 98) |
| | Light | DIVMTQSPSSLSASVGDRVTITCQASQDITNYLSWYQQKPGKAPKLLIN DASNLETGVPSRFSGSGSGTDFTFTI SSLQPEDIATYYCQQYDTLPITF GQGTRLEIKR (SEQ ID NO: 95) |
| NH24-72/47 | Heavy | EVQLVESGGGSVQPGGSLRLSCAASGFTFSSYGMNWIRQAPGKGLEWIT YISSSGGHTYYADSVKGRFTI SRDNAKNSLYLQMNSLRAEDTAVYYCAR GQGPFEYWGQGTLVTVSS (SEQ ID NO: 98) |
| | Light | DIVMTQSPSSLSASVGDRVTITCQASQDI SNYLSWYQQKPGKAPKLLIS DASNLETGVPSRFSGSGSGTDFTFTISSLQPEDIATYYCQQYDNLPITF GQGTRLEIKR (SEQ ID NO: 97) |
| NH24-162/35 | Heavy | EVQLVESGGGSVQPGGSLRLSCAASGFTFSSYGMSWVRQAPGKGLEWIS YISSSGGHTYYADSVKGQFTI SRDNAKNSLYLQMNSLRAEDTAVYYCAR GSGSFDYWGQGTLVTVSS (SEQ ID NO: 100) |
| | Light | DIVMTQSPSSLSASVGDRVTITCQASQDITNYLSWYQQKPGKAPKLLIN DASNLETGVPSRFSGSGSGTDFTFTISSLQPEDIATYYCQQYDTLPITF GQGTRLEIKR (SEQ ID NO: 95) |
| NH24-162/72 | Heavy | EVQLVESGGGSVQPGGSLRLSCAASGFTFSSYGMSWVRQAPGKGLEWIS YISSSGGHTYYADSVKGQFTI SRDNAKNSLYLQMNSLRAEDTAVYYCAR GSGSFDYWGQGTLVTVSS (SEQ ID NO: 100) |
| | Light | DIVMTQSPSSLSASVGDRVTITCQASQDISNYLSWYQQKPGKAPKLLIN DASNLETGVPSRFSGSGSGTDFTFTISSLQPEDIATYYCQQYDNLPITF GQGTRLEIKR (SEQ ID NO: 99) |
| SL-061mut 213 | Heavy | QVQLQQSGPGLVKPSQTLSLTCAISGDSVSSYSAAWNWIRQSPSRGLEW LGRTYYRSKWENDYAVSVKSRITINPDTSKNOFSLQLNSVTPEDTAVYY CARDYYGSESYYNRGYYYYGLDVWGQGTTVTVSS (SEQ ID NO: 92) |
| | Light | AIQLTQSPSSLSASVGDRVTITCRASPSISSALAWYQQKPGKAPKLLMY DESSQEGSVPSRFSGSGSGTDFTLTISSLQPEDFATYYCQQFNEYPLIF GGGTKVEIKR (SEQ ID NO: 93) |

TABLE 4

Amino acid sequences of the monoclonal antibody heavy and light chains with an Fc-silent IgG1 backbone.

| Clone | Chain | Variable Sequence |
|---|---|---|
| SL-033 | Heavy | QVQLQQSGPGLVKPSQTLSLTCAISGDSVSGYSAAWNWIRQSPSRGLEW LGRTYYRSKWYNDYAVSVKSRITINPDTSKNOFSLQLNSVTPEDTAVYY CARDYYGSESYYNRGYYYYGMDVWGQGTTVTVSSASTKGPSVFPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP |

TABLE 4-continued

Amino acid sequences of the monoclonal antibody heavy and light chains with an Fc-silent IgG1 backbone.

| Clone | Chain | Variable Sequence |
|---|---|---|
| | | APEAAGGPSVFLFPPKPKDILMISRIPEVTCVVVDVSHEDPEVKENWYV DGVEVHNAKTKPREEQYNSTYRVVSVLIVLHQDWLNGKEYKCKVSNKAL PAPIEKTISKAKGQPREPQVYTLPPSREEMTKNQVSLTCLVKGFYPSDI AVEWESNGQPENNYKITPPVLDSGSFFLYSKLTVDKSRWQQGNVFSCS VMHEALHNHYTQKSLSLSPGK (SEQ ID NO: 56) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVIKSENRGEC (SEQ ID NO: 57) |
| SL-034 | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSSASTKGPSVFPLAPSS KSTSGGTAALGCLVKDYFPEPVTVSWNSGALISGVHTFPAVLQSSGLYS LSSVVTVPSSSLGTQTYICNVNHKPSNTKVDKKVEPKSCDKTHTCPPCP APEAAGGPSVFLFPPKPKDTLMISRTPEVTCVVVDVSHEDPEVKENWYV DGVEVHNAKTKPREEQYASTYRVVSVLIVLHQDWLNGKEYKCKVSNKAL PAPIEKTISKAKGQPREPQVYTLPPSREEMTKNQVSLTCLVKGFYPSDI AVEWESNGQPENNYKITPPVLDSDGSFFLYSKLTVDKSRWQQGNVFSCS VMHEALHNHYTQKSLSLSPGK (SEQ ID NO: 58) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRIVAAPSVFIFPPSDEQLKSGTASVVCLLNNFYPREAKVQ WKVDNALQSGNSQESVTEQDSKDSTYSLSSTLILSKADYEKHKVYACEV THQGLSSPVTKSENRGEC (SEQ ID NO: 57) |
| NH24 | Heavy | EVQLVESGGGSVQPGGSLRLSCAASGFTFSSYGMSWIRQAPGKGLEWIS YISSSGGHTYYADSVKGRFTISRDNAKNSLYLQMNSLRAEDTAVYYCAR GSGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGAPSVELFPPK PKDTLMISRTPEVTCVVVDVSHEDPEVKFNWYVDGVEVHNAKTKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 59) |
| | Light | DIVMTQSPSSLSASVGDRVTITCQASQDITNYLSWYQQKPGKAPKLLIS DASNLETGIPSRFSGSGSGTDFTFTISSLQPEDIATYYCQQYDTLPITF GQGTRLEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVTKSENRGEC (SEQ ID NO: 60) |
| NH46 | Heavy | QVQLVQSGSEVKKPGASVRVSCKVSGSTVKELSMHWVRQAPGKGLEWMG GYDPEDGESIFAQKFQGRVNMTEDRSTDTAYMELSSLRSEDTAVYYCAT DLNWEDAFDVWGQGTMVTVSSASTKGPSVFPLAPSSKSTSGGTAALGCL VKDYFPEPVTVSWNSGALTSGVHTFPAVLQSSGLYSLSSVVTVPSSSLG TQTYICNVNHKPSNTKVDKKVEPKSCDKTHTCPPCPAPEAAGAPSVFLF PPKPKDTLMISRTPEVTCVVVDVSHEDPEVKFNWYVDGVEVHNAKIKPR EEQYNSTYRVVSVLIVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQK SLSLSPGK (SEQ ID NO: 61) |
| | Light | QSVLTQPPSVSAAPGQKVTISCSGSGSNIGNYYVAWYQQFPGTAPKLLI YDNNKRPSGIPDRFSGSKSGTSATLGITGLQTGDEADYYCGTWDTSLTA GDIYVFGTGTKVTVLRTVAAPSVFIFPPSDEQLKSGTASVVCLLNNFYP REAKVQWKVDNALQSGNSQESVTEQDSKDSTYSLSSTLILSKADYEKHK VYACEVTHQGLSSPVIKSENRGEC (SEQ ID NO: 62) |
| SL-038 | Heavy | EVQLVESGGGLSQPGNSLQLSCEASGFTFSNHDMNWVRQAPGKGLEWVA YISSASGLISYADSVRGRFTISRDNAKNSLFLQMNNLKSEDTAMYYCAR DPAYSGNYALDFWGQGTQVTVSSASTKGPSVFPLAPSSKSTSGGTAALG CLVKDYFPEPVTVSWNSGALISGVHTFPAVLQSSGLYSLSSVVTVPSSS LGTQTYICNVNHKPSNTKVDKKVEPKSCDKTHTCPPCPAPEAAGGPSVF LFPPKPKDTLMISRTPEVTCVVVDVSHEDPEVKFNWYVDGVEVHNAKIK PREEQYNSTYRVVSVLIVLHQDWLNGKEYKCKVSNKALPAPIEKTISKA KGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNHYT QKSLSLSPGK (SEQ ID NO: 63) |
| | Light | QPVLTQSPSASASLSGSVKLICTLSSELSSYTIVWYQQQPDKAPKYVMY LKSDGSHGKGDIPDRFSGSSSGAHRYLSVSNVQSEDDATYFCGAGYTL AGQYGWVFGSGTKVTVLRTVAAPSVFIFPPSDEQLKSGTASVVCLLNNF YPREAKVQWKVDNALQSGNSQESVTEQDSKDSTYSLSSTLTLSKADYEK HKVYACEVTHQGLSSPVIKSENRGEC (SEQ ID NO: 64) |

TABLE 4-continued

Amino acid sequences of the monoclonal antibody heavy and light chains with an Fc-silent IgG1 backbone.

| Clone | Chain | Variable Sequence |
|---|---|---|
| NH24-35 (GILA LA + G237A) | Heavy | EVQLVESGGGSVQPGGSLRLSCAASGFTFSSYGMSWIRQAPGKGLEWVS YISSSGGHTYYADSVKGRFTISRDNAKNSLYLQMNSLRAEDTAVYYCAR YSGAFDHWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKFNWYVDGVEVHNAKTKPREEQ YNSTYRVVSVLIVLHQDWLNGKEYKCKVSNKALPAPIEKTISKAKGQPR EPQVYTLPPSREEMTKNQVSLICLVKGFYPSDIAVEWESNGQPENNYKT TPPVLDSDGSFFLYSKLTVDKSRWQQGNVFSCSVMHEALHNHYTQKSLS LSPGK (SEQ ID NO: 127) |
| | Light | DIVMTQSPSSLSASVGDRVTITCQASQDITNYLSWYQQKPGKAPKLLIN DASNLETGVPSRFSGSGSGTDFTFTISSLQPEDIATYYCQQYDTLPITF GQGTRLEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVIKSENRGEC (SEQ ID NO: 128) |
| NH24-35 (GILA LA + N297A) | Heavy | EVQLVESGGGSVQPGGSLRLSCAASGFTFSSYGMSWIRQAPGKGLEWVS YISSSGGHTYYADSVKGRFTISRDNAKNSLYLQMNSLRAEDTAVYYCAR YSGAFDHWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGGPSVFLFPPK PKDTLMISRTPEVTCVVVDVSHEDPEVKFNWYVDGVEVHNAKIKPREEQ YASTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 137) |
| | Light | DIVMTQSPSSLSASVGDRVTITCQASQDITNYLSWYQQKPGKAPKLLIN DASNLETGVPSRFSGSGSGTDFTFTISSLQPEDIATYYCQQYDTLPITF GQGTRLEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVIKSENRGEC (SEQ ID NO: 128) |
| NH24-47 | Heavy | EVQLVESGGGSVQPGGSLRLSCAASGFTFSSYGMSWVRQAPGKGLEWIS YISSSGGHTYYADSVKGRFTISRDNAKNSLYLQMNSLRAEDTAVYYCAR YSGAFDRWGQGTPVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKFNWYVDGVEVHNAKIKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 129) |
| | Light | DIVMTQSPSSLSASVGDRVTITCQASQDISNYLSWYQQKPGKAPKLLIS DASNLETGVPSRFSGSGSGIDFTFTISSLQPEDIATYYCQQYDNLPITF GQGTRLEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSENRGEC (SEQ ID NO: 130) |
| NH24-72 | Heavy | EVQLVESGGGSVQPGGSLRLSCAASGFTFSSYGMNWIRQAPGKGLEWIT YISSSGGHTYYADSVKGRFTISRDNAKNSLYLQMNSLRAEDTAVYYCAR GQGPFEYWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKENWYVDGVEVHNAKIKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 131) |
| | Light | DIVMTQSPSSLSASVGDRVTITCQASQDISNYLSWYQQKPGKAPKLLIN DASNLETGVPSRFSGSGSGTDFTFTISSLQPEDIATYYCQQYDNLPITF GQGTRLEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVIKSENRGEC (SEQ ID NO: 132) |
| NH24-162 | Heavy | EVQLVESGGGSVQPGGSLRLSCAASGFTFSSYGMSWVRQAPGKGLEWIS YISSSGGHTYYADSVKGQFTISRDNAKNSLYLQMNSLRAEDTAVYYCAR GSGSFDYWGQGTLVTVSSASTKGPSVFPLAPSSKSTSGGTAALGCLVKD YFPEPVTVSWNSGALISGVHTFPAVLQSSGLYSLSSVVTVPSSSLGTQT YICNVNHKPSNTKVDKKVEPKSCDKTHTCPPCPAPEAAGAPSVELFPPK PKDTLMISRTPEVTCVVVDVSHEDPEVKFNWYVDGVEVHNAKTKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 133) |

TABLE 4-continued

Amino acid sequences of the monoclonal antibody heavy and light chains with an Fc-silent IgG1 backbone.

| Clone | Chain | Variable Sequence |
|---|---|---|
| | Light | DIVMTQSPSSLSASVGDRVTITCQASQDISNYLSWYQQKPGKAPKLLIS<br>DASNLETGVPSRFSGSGSGTDFTFTISSLQPEDIATYYCQQYDNLPITF<br>GQGTRLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSENRGEC (SEQ ID NO: 130) |
| NH24-<br>35/47 | Heavy | EVQLVESGGGSVQPGGSLRLSCAASGFTFSSYGMSWIRQAPGKGLEWVS<br>YISSSGGHTYYADSVKGRFTISRDNAKNSLYLQMNSLRAEDTAVYYCAR<br>YSGAFDHWGQGTLVTVSSASTKGPSVFPLAPSSKSTSGGTAALGCLVKD<br>YFPEPVTVSWNSGALISGVHIFPAVLQSSGLYSLSSVVTVPSSSLGTQT<br>YICNVNHKPSNTKVDKKVEPKSCDKTHTCPPCPAPEAAGAPSVFLFPPK<br>PKDTLMISRTPEVTCVVVDVSHEDPEVKFNWYVDGVEVHNAKIKPREEQ<br>YNSTYRVVSVLIVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 127) |
| | Light | DIVMTQSPSSLSASVGDRVTITCQASQDISNYLSWYQQKPGKAPKLLIS<br>DASNLETGVPSRFSGSGSGTDFTFTISSLQPEDIATYYCQQYDNLPITF<br>GQGTRLEIKRTVAAPSVFIFPPSDEQLKSGTASVVCLLNNFYPREAKVQ<br>WKVDNALQSGNSQESVTEQDSKDSTYSLSSTLILSKADYEKHKVYACEV<br>THQGLSSPVTKSENRGEC (SEQ ID NO: 130) |
| NH24-<br>35/72 | Heavy | EVQLVESGGGSVQPGGSLRLSCAASGFTFSSYGMSWIRQAPGKGLEWVS<br>YISSSGGHTYYADSVKGRFTISRDNAKNSLYLQMNSLRAEDTAVYYCAR<br>YSGAFDHWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQT<br>YICNVNHKPSNTKVDKKVEPKSCDKTHTCPPCPAPEAAGAPSVELFPPK<br>PKDTLMISRTPEVTCVVVDVSHEDPEVKFNWYVDGVEVHNAKIKPREEQ<br>YNSTYRVVSVLTVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 127) |
| | Light | DIVMTQSPSSLSASVGDRVTITCQASQDISNYLSWYQQKPGKAPKLLIN<br>DASNLETGVPSRFSGSGSGTDFTFTISSLQPEDIATYYCQQYDNLPITF<br>GQGTRLEIKRTVAAPSVFIFPPSDEQLKSGTASVVCLLNNFYPREAKVQ<br>WKVDNALQSGNSQESVTEQDSKDSTYSLSSTLILSKADYEKHKVYACEV<br>THQGLSSPVIKSFNRGEC (SEQ ID NO: 132) |
| NH24-<br>47/35 | Heavy | EVQLVESGGGSVQPGGSLRLSCAASGFTFSSYGMSWVRQAPGKGLEWIS<br>YISSSGGHTYYADSVKGRFTISRDNAKNSLYLQMNSLRAEDTAVYYCAR<br>YSGAFDRWGQGTPVTVSSASTKGPSVFPLAPSSKSTSGGTAALGCLVKD<br>YFPEPVTVSWNSGALISGVHTFPAVLQSSGLYSLSSVVTVPSSSLGTQT<br>YICNVNHKPSNTKVDKKVEPKSCDKTHTCPPCPAPEAAGAPSVFLFPPK<br>PKDTLMISRTPEVTCVVVDVSHEDPEVKFNWYVDGVEVHNAKTKPREEQ<br>YNSTYRVVSVLIVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 129) |
| | Light | DIVMTQSPSSLSASVGDRVTITCQASQDITNYLSWYQQKPGKAPKLLIN<br>DASNLETGVPSRFSGSGSGTDFTFTISSLQPEDIATYYCQQYDTLPITF<br>GQGTRLEIKRTVAAPSVFIFPPSDEQLKSGTASVVCLLNNFYPREAKVQ<br>WKVDNALQSGNSQESVTEQDSKDSTYSLSSTLILSKADYEKHKVYACEV<br>THQGLSSPVIKSENRGEC (SEQ ID NO: 128) |
| NH24-<br>47/72 | Heavy | EVQLVESGGGSVQPGGSLRLSCAASGFTFSSYGMSWVRQAPGKGLEWIS<br>YISSSGGHTYYADSVKGRFTISRDNAKNSLYLQMNSLRAEDTAVYYCAR<br>YSGAFDRWGQGTPVTVSSASTKGPSVFPLAPSSKSTSGGTAALGCLVKD<br>YFPEPVTVSWNSGALISGVHTFPAVLQSSGLYSLSSVVTVPSSSLGTQT<br>YICNVNHKPSNTKVDKKVEPKSCDKTHTCPPCPAPEAAGAPSVFLFPPK<br>PKDTLMISRTPEVTCVVVDVSHEDPEVKENWYVDGVEVHNAKTKPREEQ<br>YNSTYRVVSVLIVLHQDWLNGKEYKCKVSNKALPAPIEKTISKAKGQPR<br>EPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLS<br>LSPGK (SEQ ID NO: 129) |
| | Light | DIVMTQSPSSLSASVGDRVTITCQASQDISNYLSWYQQKPGKAPKLLIN<br>DASNLETGVPSRFSGSGSGTDFTFTISSLQPEDIATYYCQQYDNLPITF<br>GQGTRLEIKRIVAAPSVFIFPPSDEQLKSGTASVVCLLNNFYPREAKVQ<br>WKVDNALQSGNSQESVTEQDSKDSTYSLSSTLILSKADYEKHKVYACEV<br>THQGLSSPVTKSENRGEC (SEQ ID NO: 132) |
| NH24-<br>72/35 | Heavy | EVQLVESGGGSVQPGGSLRLSCAASGFTFSSYGMNWIRQAPGKGLEWIT<br>YISSSGGHTYYADSVKGRFTISRDNAKNSLYLQMNSLRAEDTAVYYCAR<br>GQGPFEYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQT<br>YICNVNHKPSNTKVDKKVEPKSCDKTHTCPPCPAPEAAGAPSVFLFPPK |

TABLE 4-continued

Amino acid sequences of the monoclonal antibody heavy and light chains with an Fc-silent IgG1 backbone.

| Clone | Chain | Variable Sequence |
|---|---|---|
| | | PKDTLMISRTPEVTCVVVDVSHEDPEVKENWYVDGVEVHNAKTKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 131) |
| | Light | DIVMTQSPSSLSASVGDRVTITCQASQDITNYLSWYQQKPGKAPKLLIN DASNLETGVPSRFSGSGSGTDFTFTISSLQPEDIATYYCQQYDTLPITF GQGTRLEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSENRGEC (SEQ ID NO: 128) |
| NH24-72/47 | Heavy | EVQLVESGGGSVQPGGSLRLSCAASGFTFSSYGMNWIRQAPGKGLEWIT YISSSGGHTYYADSVKGRFTISRDNAKNSLYLQMNSLRAEDTAVYYCAR GQGPFEYWGQGTLVTVSSASTKGPSVFPLAPSSKSTSGGTAALGCLVKD YFPEPVTVSWNSGALISGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKENWYVDGVEVHNAKTKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 131) |
| | Light | DIVMTQSPSSLSASVGDRVTITCQASQDISNYLSWYQQKPGKAPKLLIS DASNLETGVPSRFSGSGSGTDFTFTISSLQPEDIATYYCQQYDNLPITF GQGTRLEIKRIVAAPSVFIFPPSDEQLKSGTASVVCLLNNFYPREAKVQ WKVDNALQSGNSQESVTEQDSKDSTYSLSSTLILSKADYEKHKVYACEV THQGLSSPVIKSENRGEC (SEQ ID NO: 130) |
| NH24-162/35 | Heavy | EVQLVESGGGSVQPGGSLRLSCAASGFTFSSYGMSWVRQAPGKGLEWIS YISSSGGHTYYADSVKGQFTISRDNAKNSLYLQMNSLRAEDTAVYYCAR GSGSFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKFNWYVDGVEVHNAKTKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 133) |
| | Light | DIVMTQSPSSLSASVGDRVTITCQASQDITNYLSWYQQKPGKAPKLLIN DASNLETGVPSRFSGSGSGTDFTFTISSLQPEDIATYYCQQYDTLPITF GQGTRLEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVTKSENRGEC (SEQ ID NO: 128) |
| NH24-162/72 | Heavy | EVQLVESGGGSVQPGGSLRLSCAASGFTFSSYGMSWVRQAPGKGLEWIS YISSSGGHTYYADSVKGQFTISRDNAKNSLYLQMNSLRAEDTAVYYCAR GSGSFDYWGQGTLVTVSSASTKGPSVFPLAPSSKSTSGGTAALGCLVKD YFPEPVTVSWNSGALISGVHTFPAVLQSSGLYSLSSVVTVPSSSLGTQT YICNVNHKPSNTKVDKKVEPKSCDKTHTCPPCPAPEAAGAPSVFLFPPK PKDTLMISRTPEVTCVVVDVSHEDPEVKENWYVDGVEVHNAKIKPREEQ YNSTYRVVSVLIVLHQDWLNGKEYKCKVSNKALPAPIEKTISKAKGQPR EPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLS LSPGK (SEQ ID NO: 133) |
| | Light | DIVMTQSPSSLSASVGDRVTITCQASQDISNYLSWYQQKPGKAPKLLIN DASNLETGVPSRFSGSGSGTDFTFTISSLQPEDIATYYCQQYDNLPITF GQGTRLEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVIKSENRGEC (SEQ ID NO: 132) |
| SL-061 | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSSASTKGPSVFPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP APEAAGAPSVFLFPPKPKDTLMISRTPEVTCVVVDVSHEDPEVKENWYV DGVEVHNAKTKPREEQYNSTYRVVSVLIVLHQDWLNGKEYKCKVSNKAL PAPIEKTISKAKGQPREPQVYTLPPSREEMTKNQVSLTCLVKGFYPSDI AVEWESNGQPENNYKTTPPVLDSDGSFFLYSKLTVDKSRWQQGNVFSCS VMHEALHNHYTQKSLSLSPGK (SEQ ID NO: 134) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVIKSENRGEC (SEQ ID NO: 57) |

TABLE 4-continued

Amino acid sequences of the monoclonal antibody heavy and light chains with an Fc-silent IgG1 backbone.

| Clone | Chain | Variable Sequence |
|---|---|---|
| SL-061_YTE | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSSASTKGPSVFPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP APEAAGAPSVFLFPPKPKDTLYITREPEVTCVVVDVSHEDPEVKENWYV DGVEVHNAKTKPREEQYNSTYRVVSVLIVLHQDWLNGKEYKCKVSNKAL PAPIEKTISKAKGQPREPQVYTLPPSREEMTKNQVSLTCLVKGFYPSDI AVEWESNGQPENNYKITPPVLDSDGSFFLYSKLTVDKSRWQQGNVFSCS VMHEALHNHYTQKSLSLSPGK (SEQ ID NO: 150) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC (SEQ ID NO: 57) |
| SL-061_LS | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSSASTKGPSVFPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP APEAAGAPSVFLFPPKPKDTLMISRTPEVTCVVVDVSHEDPEVKENWYV DGVEVHNAKTKPREEQYNSTYRVVSVLIVLHQDWLNGKEYKCKVSNKAL PAPIEKTISKAKGQPREPQVYTLPPSREEMTKNQVSLTCLVKGFYPSDI AVEWESNGQPENNYKITPPVLDSDGSFFLYSKLTVDKSRWQQGNVFSCS VLHEALHSHYTQKSLSLSPGK (SEQ ID NO: 153) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC (SEQ ID NO: 57) |
| SL-062 | Heavy | QVQLQQSGPGLVKPSQTLSLTCAISGDSVSGYSAAWNWIRQSPSRGLEW LGRTYYRSKWYNDYAVSVKSRITINPDTSKNQFSLQLNSVTPEDTAVYY CARDYYGSESYYNRGYYYYGMDVWGQGTTVTVSSASTKGPSVEPLAPSS KSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCP APELLGGPSVFLFPPKPKDTLMISRTPEVTCVVVDVSHEDPEVKENWYV DGVEVHNAKIKPREEQYNSTYRVVSVLIVLHQDWLNGKEYKCKVSNKAL PAPIEKTISKAKGQPREPQVYTLPPSREEMTKNQVSLTCLVKGFYPSDI AVEWESNGQPENNYKTTPPVLDSDGSFFLYSKLIVDKSRWQQGNVFSCS VMHEALHNHYTQKSLSLSPGK (SEQ ID NO: 135) |
| | Light | AIQLTQSPSSLSASVGDRVTITCRASPGISSALAWYQQKPGKAPKLLMY DESSQESGVPSRFSGSGSGTDFTLTISSLQPEDFATYYCQQFNDYPLTF GGGTKVEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVTKSFNRGEC (SEQ ID NO: 57) |
| SL-061mut 213 | Heavy | QVQLQQSGPGLVKPSQTLSLTCAISGDSVSSYSAAWNWIRQSPSRGLEW LGRTYYRSKWENDYAVSVKSRITINPDTSKNQFSLQLNSVTPEDTAVYY CARDYYGSESYYNRGYYYYGLDVWGQGTTVTVSSASTKGPSVFPLAPSS KSTSGGTAALGCLVKDYFPEPVTVSWNSGALISGVHTFPAVLQSSGLYS LSSVVTVPSSSLGTQTYICNVNHKPSNTKVDKKVEPKSCDKTHTCPPCP APEAAGAPSVFLFPPKPKDTLMISRTPEVTCVVVDVSHEDPEVKENWYV DGVEVHNAKTKPREEQYNSTYRVVSVLIVLHQDWLNGKEYKCKVSNKAL PAPIEKIISKAKGQPREPQVYTLPPSREEMTKNQVSLTCLVKGFYPSDI AVEWESNGQPENNYKTTPPVLDSDGSFFLYSKLTVDKSRWQQGNVFSCS VMHEALHNHYTQKSLSLSPGK (SEQ ID NO: 151) |
| | Light | AIQLTQSPSSLSASVGDRVTITCRASPSISSALAWYQQKPGKAPKLLMY DESSQEGSVPSRFSGSGSGTDFTLTISSLQPEDFATYYCQQFNEYPLTF GGGTKVEIKRTVAAPSVFIFPPSDEQLKSGTASVVCLLNNFYPREAKVQ WKVDNALQSGNSQESVTEQDSKDSTYSLSSTLILSKADYEKHKVYACEV THQGLSSPVTKSFNRGEC (SEQ ID NO: 152) |

TABLE 5

Amino acid sequences of the biparatopic antibody heavy and light chains with an Fc-silent IgG1 backbone and knob-into-hole mutations.

| Candidate | Chain | Variable Sequence |
|---|---|---|
| 1 | SL-033 Heavy (Knob) | QVQLQQSGPGLVKPSQTLSLTCAISGDSVSGYSAAWNWIRQSPSR GLEWLGRTYYRSKWYNDYAVSVKSRITINPDTSKNQFSLQLNSVT PEDTAVYYCARDYYGSESYYNRGYYYYGMDVWGQGTTVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHICPPCPAPEAAGGPSVFLFPPKPKDTLMISR TPEVTCVVVDVSHEDPEVKFNWYVDGVEVHNAKTKPREEQYNSTY RVVSVLIVLHQDWLNGKEYKCKVSNKALPAPIEKTISKAKGQPRE PQVYTLPPCREEMTKNQVSLWCLVKGFYPSDIAVEWESNGQPENN YKTTPPVLDSDGSFFLYSKLTVDKSRWQQGNVFSCSVMHEALHNH YTQKSLSLSPGK (SEQ ID NO: 65) |
| | SL-033 Light | AIQLTQSPSSLSASVGDRVTITCRASPGISSALAWYQQKPGKAPK LLMYDESSQESGVPSRFSGSGSGTDFTLTISSLQPEDFATYYCQQ FNDYPLTFGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 57) |
| | NH24 Heavy (Hole) | EVQLVESGGGSVQPGGSLRLSCAASGFTFSSYGMSWIRQAPGKGL EWISYISSSGGHTYYADSVKGRFTISRDNAKNSLYLQMNSLRAED TAVYYCARGSGSFDYWGQGTLVTVSSASTKGPSVFPLAPSSKSTS GGTAALGCLVKDYFPEPVTVSWNSGALTSGVHTFPAVLQSSGLYS LSSVVTVPSSSLGTQTYICNVNHKPSNTKVDKKVEPKSCDKTHTC PPCPAPEAAGGPSVFLFPPKPKDTLMISRTPEVTCVVVDVSHEDP EVKFNWYVDGVEVHNAKIKPREEQYNSTYRVVSVLIVLHQDWLNG KEYKCKVSNKALPAPIEKTISKAKGQPREPQVCTLPPSREEMTKN QVSLSCAVKGFYPSDIAVEWESNGQPENNYKTTPPVLDSDGSFFL VSKLTVDKSRWQQGNVFSCSVMHEALHNHYTQKSLSLSPGK (SEQ ID NO: 66) |
| | NH24 Light | DIVMTQSPSSLSASVGDRVTITCQASQDITNYLSWYQQKPGKAPK LLISDASNLETGIPSRFSGSGSGTDFTFTISSLQPEDIATYYCQQ YDTLPITFGQGTRLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 60) |
| 2 | SL-033 Heavy (Knob) | QVQLQQSGPGLVKPSQTLSLICAISGDSVSGYSAAWNWIRQSPSR GLEWLGRTYYRSKWYNDYAVSVKSRITINPDTSKNQFSLQLNSVT PEDTAVYYCARDYYGSESYYNRGYYYYGMDVWGQGTTVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHTCPPCPAPEAAGGPSVFLFPPKPKDILMISR TPEVTCVVVDVSHEDPEVKFNWYVDGVEVHNAKTKPREEQYNSTY RVVSVLTVLHQDWLNGKEYKCKVSNKALPAPIEKTISKAKGQPRE PQVYTLPPCREEMTKNQVSLWCLVKGFYPSDIAVEWESNGQPENN YKTTPPVLDSDGSFFLYSKLTVDKSRWQQGNVFSCSVMHEALHNH YTQKSLSLSPGK (SEQ ID NO: 65) |
| | SL-033 Light | AIQLTQSPSSLSASVGDRVTITCRASPGISSALAWYQQKPGKAPK LLMYDESSQESGVPSRFSGSGSGTDFTLTISSLQPEDFATYYCQQ FNDYPLTFGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 57) |
| | NH46 Heavy (Hole) | QVQLVQSGSEVKKPGASVRVSCKVSGSTVKELSMHWVRQAPGKGL EWMGGYDPEDGESIFAQKFQGRVNMTEDRSTDTAYMELSSLRSED TAVYYCATDLNWEDAFDVWGQGTMVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPEAAGGPSVFLFPPKPKDTLMISRTPEVTCVVVDVSH EDPEVKFNWYVDGVEVHNAKTKPREEQYNSTYRVVSVLIVLHQDW LNGKEYKCKVSNKALPAPIEKTISKAKGQPREPQVCTLPPSREEM TKNQVSLSCAVKGFYPSDIAVEWESNGQPENNYKTTPPVLDSDGS FFLVSKLTVDKSRWQQGNVFSCSVMHEALHNHYTQKSLSLSPGK (SEQ ID NO: 67) |
| | NH46 Light | QSVLIQPPSVSAAPGQKVTISCSGSGSNIGNYYVAWYQQFPGTAP KLLIYDNNKRPSGIPDRFSGSKSGTSATLGITGLQTGDEADYYCG TWDTSLTAGDIYVFGTGTKVTVLRTVAAPSVFIFPPSDEQLKSGT ASVVCLLNNFYPREAKVQWKVDNALQSGNSQESVTEQDSKDSTYS LSSTLTLSKADYEKHKVYACEVTHQGLSSPVTKSENRGEC (SEQ ID NO: 62) |

TABLE 5-continued

Amino acid sequences of the biparatopic antibody heavy and light chains with an Fc-silent IgG1 backbone and knob-into-hole mutations.

| Candidate | Chain | Variable Sequence |
|---|---|---|
| 3 | SL-033 Heavy (Knob) | QVQLQQSGPGLVKPSQTLSLICAISGDSVSGYSAAWNWIRQSPSR GLEWLGRTYYRSKWYNDYAVSVKSRITINPDTSKNQFSLQLNSVT PEDTAVYYCARDYYGSESYYNRGYYYYGMDVWGQGTTVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHTCPPCPAPEAAGGPSVFLFPPKPKDILMISR TPEVTCVVVDVSHEDPEVKFNWYVDGVEVHNAKTKPREEQYNSTY RVVSVLIVLHQDWLNGKEYKCKVSNKALPAPIEKTISKAKGQPRE PQVYTLPPCREEMTKNQVSLWCLVKGFYPSDIAVEWESNGQPENN YKTTPPVLDSDGSFFLYSKLTVDKSRWQQGNVFSCSVMHEALHNH YTQKSLSLSPGK (SEQ ID NO: 65) |
| | SL-033 Light | AIQLTQSPSSLSASVGDRVTITCRASPGISSALAWYQQKPGKAPK LLMYDESSQESGVPSRFSGSGSGTDFTLTISSLQPEDFATYYCQQ FNDYPLTFGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 57) |
| | SL-038 Heavy (Hole) | EVQLVESGGGLSQPGNSLQLSCEASGFTFSNHDMNWVRQAPGKGL EWVAYISSASGLISYADSVRGRFTISRDNAKNSLFLQMNNLKSED TAMYYCARDPAYSGNYALDFWGQGTQVTVSSASTKGPSVEPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCD KTHTCPPCPAPEAAGGPSVFLFPPKPKDTLMISRTPEVTCVVVDV SHEDPEVKFNWYVDGVEVHNAKTKPREEQYNSTYRVVSVLIVLHQ DWLNGKEYKCKVSNKALPAPIEKTISKAKGQPREPQVCTLPPSRE EMTKNQVSLSCAVKGFYPSDIAVEWESNGQPENNYKTTPPVLDSD GSFFLVSKLTVDKSRWQQGNVFSCSVMHEALHNHYTQKSLSLSPG K (SEQ ID NO: 68) |
| | SL-038 Light | QPVLTQSPSASASLSGSVKLICTLSSELSSYTIVWYQQQPDKAPK YVMYLKSDGSHGKGDGIPDRFSGSSSGAHRYLSVSNVQSEDDATY FCGAGYTLAGQYGWVFGSGTKVTVLRTVAAPSVFIFPPSDEQLKS GTASVVCLLNNFYPREAKVQWKVDNALQSGNSQESVTEQDSKDST YSLSSTLILSKADYEKHKVYACEVTHQGLSSPVTKSENRGEC SEQ ID NO: 64) |
| 4 | SL-059 Heavy (Knob_pI_ENG) | QVQLQQSGPGLVKPSQTLSLTCAISGDSVSGYSAAWNWIRQSPSR GLEWLGRTYYRSKWYNDYAVSVKSRITINPDTSKNQFSLQLNSVT PEDTAVYYCARDYYGSESYYNRGYYYYGMDVWGQGTTVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSDTK VDKKVEPKSCDKTHTCPPCPAPEAAGGPSVFLFPPKPKDILMISR TPEVTCVVVDVSHEDPEVKENWYVDGVEVHNAKTKPREEEYNSTY RVVSVLTVLHQDWLNGKEYKCKVSNKALPAPIEKTISKAKGQPRE PQVYTLPPCREEMTKNQVSLWCLVKGFYPSDIAVEWESDGQPENN YKTTPPVLDSDGSFFLYSKLTVDKSRWEQGDVFSCSVMHEALHNH YTQKSLSLSPGK (SEQ ID NO: 136) |
| | SL-033 Light | AIQLTQSPSSLSASVGDRVTITCRASPGISSALAWYQQKPGKAPK LLMYDESSQESGVPSRFSGSGSGTDFTLTISSLQPEDFATYYCQQ FNDYPLTFGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 57) |
| | NH24 Heavy (Hole) | EVQLVESGGGSVQPGGSLRLSCAASGFTFSSYGMSWIRQAPGKGL EWISYISSSGGHTYYADSVKGRFTISRDNAKNSLYLQMNSLRAED TAVYYCARGSGSFDYWGQGTLVTVSSASTKGPSVFPLAPSSKSTS GGTAALGCLVKDYFPEPVTVSWNSGALISGVHIFPAVLQSSGLYS LSSVVTVPSSSLGTQTYICNVNHKPSNTKVDKKVEPKSCDKTHTC PPCPAPEAAGGPSVFLFPPKPKDTLMISRTPEVTCVVVDVSHEDP EVKFNWYVDGVEVHNAKIKPREEQYNSTYRVVSVLIVLHQDWING KEYKCKVSNKALPAPIEKTISKAKGQPREPQVCTLPPSREEMTKN QVSLSCAVKGFYPSDIAVEWESNGQPENNYKITPPVLDSDGSFFL VSKLTVDKSRWQQGNVFSCSVMHEALHNHYTQKSLSLSPGK (SEQ ID NO: 66) |
| | NH24 Light | DIVMTQSPSSLSASVGDRVTITCQASQDITNYLSWYQQKPGKAPK LLISDASNLETGIPSRFSGSGSGTDFTFTISSLQPEDIATYYCQQ YDTLPITFGQGTRLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSENRGEC (SEQ ID NO: 60) |

TABLE 6

Amino acid sequences of the scFv antibodies.

| | |
|---|---|
| NH24-35 | EVQLVESGGGSVQPGGSLRLSCAASGFTFSSYGMSWIRQAPGKGLEWVSY<br>ISSSGGHTYYADSVKGRFTISRDNAKNSLYLQMNSLRAEDTAVYYCARYS<br>GAFDHWGQGILVTVSSGGRGSGGGGSGSGGSDIVMTQSPSSLSASVGDRV<br>TITCQASQDITNYLSWYQQKPGKAPKLLINDASNLETGVPSRFSGSGSGT<br>DFTFTISSLQPEDIATYYCQQYDTLPITFGQGTRLEIKR<br>(SEQ ID NO: 103) |
| NH24-47 | EVQLVESGGGSVQPGGSLRLSCAASGFTFSSYGMSWVRQAPGKGLEWISY<br>ISSSGGHTYYADSVKGRFTISRDNAKNSLYLQMNSLRAEDTAVYYCARYS<br>GAFDRWGQGTPVTVSSGGRGSGGGGSGSGGSDIVMTQSPSSLSASVGDRV<br>TITCQASQDISNYLSWYQQKPGKAPKLLISDASNLETGVPSRFSGSGSGT<br>DFTFTISSLQPEDIATYYCQQYDNLPITFGQGTRLEIKR<br>(SEQ ID NO: 104) |
| NH24-72 | EVQLVESGGGSVQPGGSLRLSCAASGFTFSSYGMNWIRQAPGKGLEWITY<br>ISSSGGHTYYADSVKGRFTISRDNAKNSLYLQMNSLRAEDTAVYYCARGQ<br>GPFEYWGQGTLVTVSSGGRGSGGGGSGSGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 105) |
| NH24-162 | EVQLVESGGGSVQPGGSLRLSCAASGFTFSSYGMSWVRQAPGKGLEWISY<br>ISSSGGHTYYADSVKGQFTISRDNAKNSLYLQMNSLRAEDTAVYYCARGS<br>GSFDYWGQGTLVTVSSGGRGSGGGGSGSGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 106) |
| NH24-35-1 | EVQLVESGGGSVQPGGSLRLSCAASGFTFSSYGMSWIRQAPGKGLEWVSY<br>ISSSGGHTYYADSVKGRFTISRDNAKNSLYLQMNSLRAEDTAVYYCARYS<br>GAFDHWGQGTLVTVSSGGGGSGGGGSGGGGSDIVMTQSPSSLSASVGDRV<br>TITCQASQDITNYLSWYQQKPGKAPKLLINDASNLETGVPSRFSGSGSGT<br>DFTFTISSLQPEDIATYYCQQYDTLPITFGQGTRLEIKR<br>(SEQ ID NO: 107) |
| NH24-47-1 | EVQLVESGGGSVQPGGSLRLSCAASGFTFSSYGMSWVRQAPGKGLEWISY<br>ISSSGGHTYYADSVKGRFTISRDNAKNSLYLQMNSLRAEDTAVYYCARYS<br>GAFDRWGQGTPVTVSSGGGGSGGGGSGGGGSDIVMTQSPSSLSASVGDRV<br>TITCQASQDISNYLSWYQQKPGKAPKLLISDASNLETGVPSRFSGSGSGT<br>DFTFTISSLQPEDIATYYCQQYDNLPITFGQGTRLEIKR<br>(SEQ ID NO: 108) |
| NH24-72-1 | EVQLVESGGGSVQPGGSLRLSCAASGFTFSSYGMNWIRQAPGKGLEWITY<br>ISSSGGHTYYADSVKGRFTISRDNAKNSLYLQMNSLRAEDTAVYYCARGQ<br>GPFEYWGQGTLVTVSSGGGGSGGGGSGGGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 109) |
| NH24-162-1 | EVQLVESGGGSVQPGGSLRLSCAASGFTFSSYGMSWVRQAPGKGLEWISY<br>ISSSGGHTYYADSVKGQFTISRDNAKNSLYLQMNSLRAEDTAVYYCARGS<br>GSFDYWGQGTLVTVSSGGGGSGGGGSGGGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 110) |
| NH24-35/47 | EVQLVESGGGSVQPGGSLRLSCAASGFTFSSYGMSWIRQAPGKGLEWVSY<br>ISSSGGHTYYADSVKGRFTISRDNAKNSLYLQMNSLRAEDTAVYYCARYS<br>GAFDHWGQGTLVTVSSGGRGSGGGGSGSGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 111) |
| NH24-35/72 | EVQLVESGGGSVQPGGSLRLSCAASGFTFSSYGMSWIRQAPGKGLEWVSY<br>ISSSGGHTYYADSVKGRFTISRDNAKNSLYLQMNSLRAEDTAVYYCARYS<br>GAFDHWGQGTLVTVSSGGRGSGGGGSGSGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 112) |
| NH24-47/35 | EVQLVESGGGSVQPGGSLRLSCAASGFTFSSYGMSWVRQAPGKGLEWISY<br>ISSSGGHTYYADSVKGRFTISRDNAKNSLYLQMNSLRAEDTAVYYCARYS<br>GAFDRWGQGTPVTVSSGGRGSGGGGSGSGGSDIVMTQSPSSLSASVGDRV<br>TITCQASQDITNYLSWYQQKPGKAPKLLINDASNLETGVPSRFSGSGSGT<br>DFTFTISSLQPEDIATYYCQQYDTLPITFGQGTRLEIKR<br>(SEQ ID NO: 113) |

TABLE 6-continued

Amino acid sequences of the scFv antibodies.

NH24-47/72      EVQLVESGGGSVQPGGSLRLSCAASGFTFSSYGMSWVRQAPGKGLEWISY
                ISSSGGHTYYADSVKGRFTISRDNAKNSLYLQMNSLRAEDTAVYYCARYS
                GAFDRWGQGTPVTVSSGGRGSGGGGSGSGGSDIVMTQSPSSLSASVGDRV
                TITCQASQDISNYLSWYQQKPGKAPKLLINDASNLETGVPSRFSGSGSGT
                DFTFTISSLQPEDIATYYCQQYDNLPITFGQGTRLEIKR
                (SEQ ID NO: 114)

NH24-72/35      EVQLVESGGGSVQPGGSLRLSCAASGFTFSSYGMNWIRQAPGKGLEWITY
                ISSSGGHTYYADSVKGRFTISRDNAKNSLYLQMNSLRAEDTAVYYCARGQ
                GPFEYWGQGTLVTVSSGGRGSGGGGSGSGGSDIVMTQSPSSLSASVGDRV
                TITCQASQDITNYLSWYQQKPGKAPKLLINDASNLETGVPSRFSGSGSGT
                DFTFTISSLQPEDIATYYCQQYDTLPITFGQGTRLEIKR
                (SEQ ID NO: 115)

NH24-72/47      EVQLVESGGGSVQPGGSLRLSCAASGFTFSSYGMNWIRQAPGKGLEWITY
                ISSSGGHTYYADSVKGRFTISRDNAKNSLYLQMNSLRAEDTAVYYCARGQ
                GPFEYWGQGTLVTVSSGGRGSGGGGSGSGGSDIVMTQSPSSLSASVGDRV
                TITCQASQDISNYLSWYQQKPGKAPKLLISDASNLETGVPSRFSGSGSGT
                DFTFTISSLQPEDIATYYCQQYDNLPITFGQGTRLEIKR
                (SEQ ID NO: 116)

NH24-162/35     EVQLVESGGGSVQPGGSLRLSCAASGFTFSSYGMSWVRQAPGKGLEWISY
                ISSSGGHTYYADSVKGQFTISRDNAKNSLYLQMNSLRAEDTAVYYCARGS
                GSFDYWGQGTLVTVSSGGRGSGGGGSGSGGSDIVMTQSPSSLSASVGDRV
                TITCQASQDITNYLSWYQQKPGKAPKLLINDASNLETGVPSRFSGSGSGT
                DFTFTISSLQPEDIATYYCQQYDTLPITFGQGTRLEIKR
                (SEQ ID NO: 117)

NH24-162/72     EVQLVESGGGSVQPGGSLRLSCAASGFTFSSYGMSWVRQAPGKGLEWISY
                ISSSGGHTYYADSVKGQFTISRDNAKNSLYLQMNSLRAEDTAVYYCARGS
                GSFDYWGQGTLVTVSSGGRGSGGGGSGSGGSDIVMTQSPSSLSASVGDRV
                TITCQASQDISNYLSWYQQKPGKAPKLLINDASNLETGVPSRFSGSGSGT
                DFTFTISSLQPEDIATYYCQQYDNLPITFGQGTRLEIKR
                (SEQ ID NO: 118)

NH24-35/47-1    EVQLVESGGGSVQPGGSLRLSCAASGFTFSSYGMSWIRQAPGKGLEWVSY
                ISSSGGHTYYADSVKGRFTISRDNAKNSLYLQMNSLRAEDTAVYYCARYS
                GAFDHWGQGTLVTVSSGGGGSGGGGSGGGGSDIVMTQSPSSLSASVGDRV
                TITCQASQDISNYLSWYQQKPGKAPKLLISDASNLETGVPSRFSGSGSGT
                DFTFTISSLQPEDIATYYCQQYDNLPITFGQGTRLEIKR
                (SEQ ID NO: 119)

NH24-35/72-1    EVQLVESGGGSVQPGGSLRLSCAASGFTFSSYGMSWIRQAPGKGLEWVSY
                ISSSGGHTYYADSVKGRFTISRDNAKNSLYLQMNSLRAEDTAVYYCARYS
                GAFDHWGQGTLVTVSSGGGGSGGGGSGGGGSDIVMTQSPSSLSASVGDRV
                TITCQASQDISNYLSWYQQKPGKAPKLLINDASNLETGVPSRFSGSGSGT
                DFTFTISSLQPEDIATYYCQQYDNLPITFGQGTRLEIKR
                (SEQ ID NO: 120)

NH24-47/35-1    EVQLVESGGGSVQPGGSLRLSCAASGFTFSSYGMSWVRQAPGKGLEWISY
                ISSSGGHTYYADSVKGRFTISRDNAKNSLYLQMNSLRAEDTAVYYCARYS
                GAFDRWGQGTPVTVSSGGGGSGGGGSGGGGSDIVMTQSPSSLSASVGDRV
                TITCQASQDITNYLSWYQQKPGKAPKLLINDASNLETGVPSRFSGSGSGT
                DFTFTISSLQPEDIATYYCQQYDILPITFGQGTRLEIKR
                (SEQ ID NO: 121)

NH24-47/72-1    EVQLVESGGGSVQPGGSLRLSCAASGFTFSSYGMSWVRQAPGKGLEWISY
                ISSSGGHTYYADSVKGRFTISRDNAKNSLYLQMNSLRAEDTAVYYCARYS
                GAFDRWGQGTPVTVSSGGGGSGGGGSGGGGSDIVMTQSPSSLSASVGDRV
                TITCQASQDISNYLSWYQQKPGKAPKLLINDASNLETGVPSRFSGSGSGT
                DFTFTISSLQPEDIATYYCQQYDNLPITFGQGTRLEIKR
                (SEQ ID NO: 122)

NH24-72/35-1    EVQLVESGGGSVQPGGSLRLSCAASGFTFSSYGMNWIRQAPGKGLEWITY
                ISSSGGHTYYADSVKGRFTISRDNAKNSLYLQMNSLRAEDTAVYYCARGQ
                GPFEYWGQGTLVTVSSGGGGGGGGSGGGGSDIVMTQSPSSLSASVGDRV
                TITCQASQDITNYLSWYQQKPGKAPKLLINDASNLETGVPSRFSGSGSGT
                DFTFTISSLQPEDIATYYCQQYDTLPITFGQGTRLEIKR
                (SEQ ID NO: 123)

NH24-72/47-1    EVQLVESGGGSVQPGGSLRLSCAASGFTFSSYGMNWIRQAPGKGLEWITY
                ISSSGGHTYYADSVKGRFTISRDNAKNSLYLQMNSLRAEDTAVYYCARGQ
                GPFEYWGQGTLVTVSSGGGGSGGGGSGGGGSDIVMTQSPSSLSASVGDRV
                TITCQASQDISNYLSWYQQKPGKAPKLLISDASNLETGVPSRFSGSGSGT
                DFTFTISSLQPEDIATYYCQQYDNLPITFGQGTRLEIKR
                (SEQ ID NO: 124)

TABLE 6-continued

Amino acid sequences of the scFv antibodies.

| | |
|---|---|
| NH24-162/35-1 | EVQLVESGGGSVQPGGSLRLSCAASGFTFSSYGMSWVRQAPGKGLEWISY<br>ISSSGGHTYYADSVKGQFTISRDNAKNSLYLQMNSLRAEDTAVYYCARGS<br>GSFDYWGQGTLVTVSSGGGGSGGGGSGGGGSDIVMTQSPSSLSASVGDRV<br>TITCQASQDITNYLSWYQQKPGKAPKLLINDASNLETGVPSRFSGSGSGT<br>DFTFTISSLQPEDIATYYCQQYDTLPITFGQGTRLEIKR<br>(SEQ ID NO: 125) |
| NH24-162/72-1 | EVQLVESGGGSVQPGGSLRLSCAASGFTFSSYGMSWVRQAPGKGLEWISY<br>ISSSGGHTYYADSVKGQFTISRDNAKNSLYLQMNSLRAEDTAVYYCARGS<br>GSFDYWGQGTLVTVSSGGGGSGGGGSGGGGSDIVMTQSPSSLSASVGDRV<br>TITCQASQDISNYLSWYQQKPGKAPKLLINDASNLETGVPSRFSGSGSGT<br>DFTFTISSLQPEDIATYYCQQYDNLPITFGQGTRLEIKR<br>(SEQ ID NO: 126) |

I. Definitions

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the inherent variation in the method being employed to determine the value, the variation that exists among the study subjects, or a value that is within 10% of a stated value.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

"Nucleic acid," "nucleic acid sequence," "oligonucleotide," "polynucleotide" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc. A polynucleotide described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. The following are non-limiting examples of polynucleotides: a gene or gene fragment, exons, introns, messenger RNA (mRNA), transfer RNA, ribosomal RNA, ribozymes, cDNA, cRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, the term polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule. Unless otherwise indicated, a particular polynucleotide sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

Other terms used in the fields of recombinant nucleic acid technology, immunology, antibody engineering, and molecular and cell biology as used herein will be generally understood by one of ordinary skill in the applicable arts.

II. Antibodies and Modifications of Antibodies

The antibodies of the present invention have several applications, including as immunotherapy in patients in need thereof. As such, in some cases, the antibodies of the present invention can be used to treat inflammatory diseases and autoimmune diseases. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv, Fd, Fd', single chain antibody (ScFv), diabody, linear antibody), mutants thereof, naturally occurring variants, fusion proteins comprising an antibody portion with an antigen recognition site of the required specificity, chimeric antibodies, and any other modified configuration of the immunoglobulin molecule that comprises an antigen recognition site of the required specificity.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular instances, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. An isolated antibody includes the antibody in situ within recombinant cells since at least one component of the antibody's natural environment will not be present. Ordinarily, however, an isolated antibody will be prepared by at least one purification step.

The basic four-chain antibody unit is a heterotetrameric glycoprotein composed of two identical light (L) chains and two identical heavy (H) chains. The term "heavy chain" as used herein refers to the larger immunoglobulin subunit which associates, through its amino terminal region, with the immunoglobulin light chain. The heavy chain comprises a variable region ($V_H$) and a constant region ($C_H$). The constant region further comprises the $C_H1$, hinge, $C_H2$, and $C_H3$ domains. In the case of IgE, IgM, and IgY, the heavy chain comprises a $C_H4$ domain but does not have a hinge domain. Those skilled in the art will appreciate that heavy chains are classified as gamma, mu, alpha, delta, or epsilon (γ, μ, α, δ, ε), with some subclasses among them (e.g., γ1-γ4, α1-α2). It is the nature of this chain that determines the "class" of the antibody as IgG, IgM, IgA IgD, or IgE, respectively. The immunoglobulin subclasses (isotypes), e.g., IgG1, IgG2, IgG3, IgG4, IgA1, etc. are well characterized and are known to confer functional specialization.

The term "light chain" as used herein refers to the smaller immunoglobulin subunit which associates with the amino terminal region of a heavy chain. As with a heavy chain, a light chain comprises a variable region ($V_L$) and a constant region ($C_L$). Light chains are classified as either kappa or lambda (κ, λ) based on the amino acid sequences of their constant domains ($C_L$). A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

An IgM antibody, for example, consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

A "variable region" of an antibody refers to the variable region of the antibody light chain or the variable region of the antibody heavy chain, either alone or in combination. The term "variable" refers to the fact that certain segments of the variable regions differ extensively in sequence among antibodies. The variable regions of both the light ($V_L$) and heavy ($V_H$) chain portions mediate antigen binding and define the specificity of a particular antibody for its particular antigen. However, the variability is not evenly distributed across the entirety of the variable regions. Instead, the variable regions consist of relatively invariant stretches called framework regions (FRs) separated by shorter regions of extreme variability called complementarity determining regions (CDRs) or hypervariable regions. The variable regions of native heavy and light chains each comprise four FRs, largely adopting a beta-sheet configuration, connected by three CDRs, which form loops connecting, and in some cases forming part of, the beta-sheet structure. The CDRs complement an antigen's shape and determine the antibody's affinity and specificity for the antigen. There are six CDRs in both $V_L$ and $V_H$. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)). As used herein, a CDR may refer to CDRs defined by any of these numbering approaches or by a combination of approaches or by other desirable approaches. In addition, a new definition of highly conserved core, boundary and hyper-variable regions can be used.

A "constant region" of an antibody refers to the constant region of the antibody light chain or the constant region of the antibody heavy chain, either alone or in combination. The constant regions of the light chain ($C_L$) and the heavy chain ($C_H1$, $C_H2$ or $C_H3$, or $C_H4$ in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody. The constant regions are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

A heavy chain variable region sequence, for example, the $V_H$ sequence of any one of SEQ ID NOs: 48, 50, 52, and 54, or any variants thereof, may be covalently linked to a variety of heavy chain constant region sequences known in the art. Similarly, it is contemplated that a light chain variable region sequence, for example, the $V_L$ of any one of SEQ ID NOs: 49, 51, 53, and 55, or any variants thereof, may be covalently linked to a variety of light chain constant region sequences known in the art.

For example, an antibody or antibody fragment may have a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. The antibody or antibody fragment may have a light chain constant region chosen from, e.g., the (e.g., human) light chain constant regions of kappa or lambda. The constant region may be altered, e.g., mutated, to modify the properties of the antibody or antibody fragment (e.g., to increase or decrease one or more of: Fc receptor binding, antibody glycosylation, the number of cysteine residues, effector cell function, and/or complement function). The antibody or antibody fragment may not recruit effector cells or fix complement. The antibody or antibody fragment may have reduced or no ability to bind an Fc receptor. For example, it is an isotype or subtype, fragment or other mutant, which does not support binding to an Fc receptor, e.g., it has a mutagenized or deleted Fc receptor binding region.

The constant region of the heavy chain of the antibody or antibody fragment may be a human IgG1 isotype, having an amino acid sequence:

(SEQ ID NO: 69)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPE[LL]G[G]PSVFLFPPKPKDTLMISRTPEVTCVVVDVS

HEDPEVKFNWYVDGVEVHNAKTKPREEQY[N]STYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The human IgG1 constant region may be modified at amino acid Asn297 (boxed in SEQ ID NO: 69 in the preceding paragraph) to prevent glycosylation of the antibody, for example Asn297Ala (N297A). The constant region of the antibody may be modified at amino acid Leu235 (boxed in SEQ ID NO: 69 in the preceding paragraph) to alter Fc receptor interactions, for example Leu235Glu (L235E) or Leu235Ala (L235A). The constant region of the antibody may be modified at amino acid Leu234 (boxed in SEQ ID NO: 69 in the preceding paragraph) to alter Fc receptor interactions, e.g., Leu234Ala (L234A). The constant region of the antibody may be altered at both amino acid 234 and 235, for example Leu234Ala and Leu235Ala (L234A/L235A). The constant region of the antibody may be modified at amino acid Gly237 (boxed in SEQ ID NO: 69 in the preceding paragraph) to alter Fc receptor interactions, for example Gly237Ala (G237A). The constant region of the antibody may be altered at amino acids 234, 234, and 237 for example, Leu234Ala, Leu235Ala, and Gly237Ala (L234A/L235A/G237A). All residue numbers are according to EU numbering (Kabat, E. A., et al. (1991) SEQUENCES OF PROTEINS OF IMMUNOLOGICAL INTEREST, FIFTH EDITION, U.S. Department of Health and Human Services, NIH Publication No. 91-3242).

The constant region of the heavy chain of the antibody may be a human IgG1 isotype, having an amino acid sequence:

(SEQ ID NO: 70)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPE[LL]G[G]PSVFLFPPKPKDTLMISRTPEVTCVVVDVS

HEDPEVKFNWYVDGVEVHNAKTKPREEQY[N]STYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The human IgG1 constant region may be modified at amino acid Asn297 (boxed in SEQ ID NO: 70 in the preceding paragraph) to prevent glycosylation of the antibody, for example Asn297Ala (N297A). The constant region of the antibody may be modified at amino acid Leu235 (boxed in SEQ ID NO: 70 in the preceding paragraph) to alter Fc receptor interactions, for example Leu235Glu (L235E) or Leu235Ala (L235A). The constant region of the antibody may be modified at amino acid Leu234 (boxed in SEQ ID NO: 70 in the preceding paragraph) to alter Fc receptor interactions, e.g., Leu234Ala (L234A). The constant region of the antibody may be altered at both amino acid 234 and 235, for example Leu234Ala and Leu235Ala (L234A/L235A). The constant region of the antibody may be modified at amino acid Gly237 (boxed in SEQ ID NO: 70 in the preceding paragraph) to alter Fc receptor interactions, for example Gly237Ala (G237A). The constant region of the antibody may be altered at amino acids 234, 234, and 237 for example, Leu234Ala, Leu235Ala, and Gly237Ala (L234A/L235A/G237A). All residue numbers are according to EU numbering (Kabat, E. A., et al., supra).

The human IgG1 constant region $C_H3$ domain may be modified to comprise either a "knob" mutation or a "hole" mutation for heterodimerization with a second constant region (residue numbers according to EU numbering (Kabat, E. A., et al., supra)). Specific knob mutations are one or more amino acid substitutions to increase the contact surface between two domains by incorporating one or more amino acids that provide for an additional protuberance of a beta-strand structure, e.g., one or more knob mutations selected from the group consisting of T366Y, T366W, T394W, and F405A (numbering according to EU index of Kabat). Knob mutations specifically provide a matching (cognate) surface to bind another antibody domain, which is modified to incorporate one or more hole mutations. The domain having the knob mutations may further comprise substitutions N208D/Q295E/N384D/Q418E/N421D.

Specific hole mutations are one or more amino acid substitutions to increase the contact surface between two domains by incorporating one or more amino acids that provide for an additional cave of a beta-strand structure, e.g., one or more hole mutations selected from the group consisting of T366S, L368A, Y407T, and Y407V (numbering according to EU index of Kabat). Hole mutations specifically provide a matching (cognate) surface to bind another antibody domain, which is modified to incorporate one or more knob mutations.

Matching knob-into-hole mutations are, e.g., T366Y on one CH3 domain and the matching Y407T on the second CH3 domain of the CH3 domain pair, herein referred to as T366Y/Y407'T. Exemplary matching mutations are T366Y/Y407'T; F405A/T394'W; T366Y:F405A/T394'W:Y407'T; T366WY407'A; and S354C:T366WY349'C:T366'S:L368'A:Y407'V.

The constant region of the heavy chain of the antibody may be a human IgG1 isotype, e.g., an allotype of the human IgG1 isotype, e.g., the IgG1 G1m3 allotype. Exemplary human IgG1 allotypes are described in Magdelaine-Beuzelin et al. (2009) PHARMACOGENET. GENOMICS 19(5):383-7.

The constant region of the heavy chain of the antibody may be a human IgG2 isotype, having an amino acid sequence:

(SEQ ID NO: 71)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDISVEWESNGQPENNYKTTPPMLDSDGSFFLYSKLTVDKSRWQQGN

VFSCSVMHEALHNHYTQKSLSLSPGK.

The human IgG2 constant region may be modified at amino acid Asn297 (boxed in SEQ ID NO: 71 in the preceding paragraph) to prevent to glycosylation of the antibody, e.g., Asn297Ala (N297A), where the residue numbers are according to EU numbering (Kabat, E. A., et al., supra).

The constant region of the heavy chain of the antibody may be a human IgG3 isotype, having an amino acid sequence:

(SEQ ID NO: 72)
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK.

The human IgG3 constant region may be modified at amino acid Asn297 (boxed in SEQ ID NO: 72 in the preceding paragraph) to prevent to glycosylation of the antibody, e.g., Asn297Ala (N297A). The human IgG3 constant region may be modified at amino acid Arg435 (boxed in SEQ ID NO: 72 in the preceding paragraph) to extend the half-life, e.g., Arg435H (R435H). All residue numbers are according to EU numbering (Kabat, E. A., et al., supra).

The constant region of the heavy chain of the antibody may be a human IgG4 isotype, having an amino acid sequence:

(SEQ ID NO: 73)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVICVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

The human IgG4 constant region may be modified within the hinge region to prevent or reduce strand exchange, e.g., the human IgG4 constant region is modified at Ser228 (boxed in SEQ ID NO: 73 in the preceding paragraph), e.g., Ser228Pro (S228P). The human IgG4 constant region may be modified at amino acid Leu235 (boxed in SEQ ID NO: 73 in the preceding paragraph) to alter Fc receptor interactions, e.g., Leu235Glu (L235E). The human IgG4 constant region may be modified at both Ser228 and Leu335, e.g., Ser228Pro and Leu235Glu (S228P/L235E). The human IgG4 constant region may be modified at amino acid Asn297 (boxed in SEQ ID NO: 73 in the preceding paragraph) to prevent to glycosylation of the antibody, e.g., Asn297Ala (N297A). All residue numbers are according to EU numbering (Kabat, E. A., et al., supra).

The human IgG constant region may be modified to enhance FcRn binding. Examples of Fc mutations that enhance binding to FcRn are Met252Tyr, Ser254Thr, Thr256Glu (M252Y, S254T, T256E, respectively) (Dall'Acqua et al. (2006) J. BIOL. CHEM. 281(33): 23514-

23524), or Met428Leu and Asn434Ser (M428L, N434S) (Zalevsky et al. (2010) NATURE BIOTECH. 28(2): 157-159). All residue numbers are according to EU numbering (Kabat, E. A., et al., supra).

The constant region of the light chain of the antibody may be a human kappa constant region, e.g., a human kappa constant region having the amino acid sequence:

(SEQ ID NO: 74)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

The constant region of the light chain of the antibody may be a human kappa constant region, e.g., a human kappa constant region having the amino acid sequence:

(SEQ ID NO: 75)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSENRGEC.

The constant region of the light chain of the antibody may be a human lambda constant region, e.g., a human lambda constant region having the amino acid sequence:

(SEQ ID NO: 76)
GQPKANPTVTLFPPSSEELQANKATLVCLISDFYPGAVTVAWKADGSPV

KAGVETTKPSKQSNNKYAASSYLSLTPEQWKSHRSYSCQVTHEGSTVEK

TVAPTEC,

The antibody may be an antibody fragment. "Antibody fragments" comprise only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_{H1}$ domains; (ii) the Fab' fragment, which is a Fab fragment having one or more cysteine residues at the C-terminus of the $C_{H1}$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single antibody; (vi) the dAb fragment which consists of a $V_H$ domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain ($V_H$) connected to a light chain variable domain ($V_L$) in the same polypeptide chain; (xi) "linear antibodies" comprising a pair of tandem Fd segments ($V_H$—$C_H$1-$V_H$-$C_H$1) which, together with complementary light chain polypeptides, form a pair of antigen binding regions.

The antibody may be a chimeric antibody. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another.

A. Monoclonal Antibodies

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The monoclonal antibodies may also be isolated from phage antibody libraries using the techniques described in Clackson et al., Nature, 352: 624-628 (1991) and Marks et al., J. Mol. Biol., 222:581-597 (1991), for example.

Methods for producing monoclonal antibodies of various types, including chimeric and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817, 837; 3,850,752; 3,939,350; 3,996,345; 4,196,265; 4,275, 149; 4,277,437; 4,366,241; 4,469,797; 4,472,509; 4,606, 855; 4,703,003; 4,742,159; 4,767,720; 4,816,567; 4,867, 973; 4,938,948; 4,946,778; 5,021,236; 5,164,296; 5,196, 066; 5,223,409; 5,403,484; 5,420,253; 5,565,332; 5,571, 698; 5,627,052; 5,656,434; 5,770,376; 5,789,208; 5,821, 337; 5,844,091; 5,858,657; 5,861,155; 5,871,907; 5,969, 108; 6,054,297; 6,165,464; 6,365,157; 6,406,867; 6,709, 659; 6,709,873; 6,753,407; 6,814,965; 6,849,259; 6,861, 572; 6,875,434; and 6,891,024, each incorporated herein by reference.

B. Single Chain Antibodies

A single chain variable fragment (scFv) is a fusion of the variable regions of the heavy and light chains of immunoglobulins, linked together with a short linker. This chimeric molecule retains the specificity of the original immunoglobulin, despite removal of the constant regions and the introduction of a linker peptide. This modification usually leaves the specificity unaltered. scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. For example, the linker may have a proline residue two residues after the $V_H$ C terminus and an abundance of arginines and prolines at other positions. As another example, the linker may have the sequence of GGRGSGGGGSGSGGS (SEQ ID NO: 101) or GGGGSGGGGSGGGGS (SEQ ID NO: 102).

A single-chain antibody may also be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a stepwise manner, hetero-bifunctional cross-linkers can be used that eliminate unwanted homopolymer formation.

An exemplary hetero-bifunctional cross-linker contains two reactive groups: one reacting with a primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide bond-containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

For example, SMPT is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane. The use of such cross-linkers is well understood in the art. Flexible linkers may also be used.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

C. Bispecific and Multispecific Antibodies

Antibodies may be bispecific or multispecific. "Bispecific antibodies" are antibodies that have binding specificities for at least two different epitopes. Such antibodies combine a first binding site for a first epitope with a second binding site for a second epitope. The first epitope and the second epitope may be two different epitopes of a single antigen. Such antibodies may be called biparatopic. Alternatively, the first epitope and the second epitope may be on two different antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities. Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low.

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

The bispecific antibodies may be composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998)). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment am forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

A bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400). Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters*. 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science*, 358(6359):85-90, 2017). The antibodies may also involve sequences or moieties that permit dimerization or multimerization of the receptors. Such sequences include those derived from IgA, which permit formation of multimers in conjunction with the J-chain. Another multimerization domain is the Gal4 dimerization domain.

A multivalent antibody may be internalized (and/or catabolized) faster than a bivalent antibody by a cell expressing an antigen to which the antibody binds. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. Multivalent antibodies may comprise (or consist of) three to about eight, for example four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: $V_H$-$C_H$1-flexible linker-$V_H$-$C_H$1-Fc region chain; or $V_H$-$C_H$1-$V_H$-$C_H$1-Fc region chain. The multivalent antibody herein may further comprise at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a $V_H/V_L$ exchange in one (or more, in case of molecules comprising more than two antigen-binding Fab molecules) of their binding arms (see also PCT publication no. WO 2015/150447, particularly the examples therein, incorporated herein by reference in its entirety).

D. Antibody Conjugates

Antibodies of the present disclosure may be linked to at least one agent to form an antibody conjugate. The conjugate can be, for example, an antibody conjugated to another proteinaceous, carbohydrate, lipid, or mixed moiety molecule(s). Such antibody conjugates include, but are not limited to, modifications that include linking the antibody to one or more polymers. For example, an antibody may be linked to one or more water-soluble polymers. Linkage to a water-soluble polymer reduces the likelihood that the antibody will precipitate in an aqueous environment, such as a physiological environment. One skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, an enzyme (e.g., that catalyzes a colorimetric or fluorometric reaction), a substrate, a solid matrix, such as biotin. An antibody may comprise one, two, or more of any of these labels.

Antibody conjugates are also used as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

The paramagnetic ions contemplated for use as conjugates include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and bismuth (III).

The radioactive isotopes contemplated for use as conjugated include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred. Technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

The fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

Another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light. In particular, 2- and 8-azido analogues of purine nucleotides have been used as site-directed photoprobes to identify nucleotide binding proteins in crude cell extracts. The 2- and 8-azido nucleotides have also been used to map nucleotide binding domains of purified proteins and may be used as antibody binding agents.

Derivatization of immunoglobulins by selectively introducing sulfhydryl groups in the Fc region of an immunoglobulin, using reaction conditions that do not alter the antibody combining site are also contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature. This approach has been reported to produce diagnostically and therapeutically promising antibodies which are currently in clinical evaluation.

E. Production and Purification of Antibodies

The methods for generating monoclonal antibodies generally begin along the same lines as those for preparing polyclonal antibodies. The first step for both of these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59, and combinations of immunostimulatory molecules ("Adjuvant Systems", such as AS01 or AS03). Additional experimental forms of inoculation to induce antigen-specific B cells are possible, including nanoparticle vaccines, or gene-encoded antigens delivered as DNA or RNA genes in a physical delivery system (such as lipid nanoparticle or on a gold biolistic bead), and delivered with needle, gene gun, or transcutaneous electroporation device. The antigen gene also can be carried as encoded by a replication competent or defective viral vector such as adenovirus, adeno-associated virus, poxvirus, herpesvirus, or alphavirus replicon, or alternatively a virus-like particle.

Methods for generating hybrids of antibody-producing spleen or lymph node cells and myeloma cells usually comprise mixing somatic cells with myeloma cells in a 2:1 proportion, though the proportion may vary from about 20:1 to about 1:1, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus or polyethylene glycol (PEG) are also known. The use of electrically induced fusion methods is also appropriate. Fusion procedures usually produce viable hybrids at low frequencies, about $1\times10^{-6}$ to $1\times10^{-8}$, but with optimized procedures one can achieve fusion efficiencies close to 1 in 200. However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide monoclonal antibodies. The cell lines may be exploited for monoclonal antibody production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as $E.\ coli$, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

Alternatively, a molecular cloning approach may be used to generate monoclonal antibodies. Single B cells labeled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

Monoclonal antibodies produced by any means may be purified, if desired, using filtration, centrifugation, and various chromatographic methods, such as FPLC or affinity chromatography. Fragments of the monoclonal antibodies of the disclosure can be obtained from the purified monoclonal antibodies by methods that include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

The antibodies of the present disclosure may be purified. The term "purified," as used herein, is intended to refer to a composition, isolatable from other components, wherein the protein is purified to any degree relative to its naturally obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

F. Modification of Antibodies

The sequences of antibodies may be modified for a variety of reasons, such as improved expression, improved cross-reactivity, or diminished off-target binding. Modified antibodies may be made by any technique known to those of skill in the art, including expression through standard molecular biological techniques, or the chemical synthesis of polypeptides.

For example, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

The substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, non-aromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

An amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain)

and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

An isolated monoclonal antibody, or antigen binding fragment thereof, may contain a substantially homogeneous glycan without sialic acid, galactose, or fucose. The aforementioned substantially homogeneous glycan may be covalently attached to the heavy chain constant region.

A monoclonal antibody may have a novel Fc glycosylation pattern. Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

The isolated monoclonal antibody, or antigen binding fragment thereof, may be present in a substantially homogenous composition represented by the GNGN or G1/G2 glycoform, which exhibits increased binding affinity for Fc gamma RI and Fc gamma RIII compared to the same antibody without the substantially homogeneous GNGN glycoform and with G0, G1F, G2F, GNF, GNGNF or GNG-NFX containing glycoforms. Fc glycosylation plays a significant role in anti-viral and anti-cancer properties of therapeutic mAbs. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, may be expressed in cells that express beta (1,4)-N-acetylglucosaminyltransferase III (GnT III), such that GnT III adds GlcNAc to the antibody. Methods for producing antibodies in such a fashion are provided in WO/9954342 and WO/03011878. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express monoclonal antibodies.

It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene comprising the cDNA encoding the antibodies.

Antibodies can be engineered to enhance solubility. For example, some hydrophilic residues such as aspartic acid, glutamic acid, and serine contribute significantly more favorably to protein solubility than other hydrophilic residues, such as asparagine, glutamine, threonine, lysine, and arginine.

B cell repertoire deep sequencing of human B cells from blood donors has been performed on a wide scale. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

G. Characterization of Antibodies

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody binds may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce monoclonal antibodies having the desired characteristics. MAP may be used to sort the antibodies of the disclosure into groups of antibodies binding different epitopes.

The present disclosure includes antibodies that may bind to the same epitope, or a portion of the same epitope. One can easily determine whether an antibody binds to the same epitope as, or competes for binding with, a reference antibody by using routine methods known in the art. For example, to determine if a test antibody binds to the same epitope as a reference antibody, the reference antibody is allowed to bind to the target molecule under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if a test antibody competes for binding with a disclosed antibody, the above-described binding methodology is performed in two orientations: In a first orientation, the disclosed antibody is allowed to bind to TNFRSF25 under saturating conditions followed by assessment of binding of the test antibody to TNFRSF25. In a second orientation, the test antibody is allowed to bind to TNFRSF25 under saturating conditions followed by assessment of binding of the disclosed antibody to TNFRSF25. If, in both orientations, only the first (saturating) antibody is capable of binding to TNFRSF25, then it is concluded that the test antibody and the disclosed antibody compete for binding to TNFRSF25. As will be appreciated by a person of ordinary skill in the art, a test antibody that competes for binding with a disclosed antibody may not necessarily bind to the identical epitope as the disclosed antibody, but may sterically block binding of the disclosed antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90%, or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In another aspect, the antibodies may be defined by their variable sequence, which include additional "framework" regions. These are provided in Table 3 that represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions. Each of the foregoing applies to the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the antibodies provided herein and their antigen-binding fragments. A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered $C_H1$, hinge, $C_H2$, $C_H3$ or $C_H4$ regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art.

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

One can determine the biophysical properties of antibodies. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

III. Pharmaceutical Formulations

The present disclosure provides pharmaceutical compositions comprising antibodies that bind to human TNFRSF25. Such compositions comprise a prophylactically or therapeutically effective amount of an antibody or a fragment thereof and a pharmaceutically acceptable carrier.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. Water is a particular carrier when the pharmaceutical composition is administered intravenously. Saline solutions and aqueous dextrose and glycerol solutions can also be employed as liquid carriers, particularly for injectable solutions. The pH and exact concentration of the various components in a pharmaceutical composition are adjusted according to well-known parameters.

The active ingredients can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in Remington's Pharmaceutical Sciences. Such compositions will contain a prophylactically or therapeutically effective amount of the antibody or fragment thereof, preferably in purified form, together with a suitable amount of carrier so as to provide the form for proper administration to the patient.

Passive transfer of antibodies generally will involve the use of intravenous or intramuscular injections. The forms of antibody can be as monoclonal antibodies. The antibodies will be formulated in a carrier suitable for injection, i.e., sterile and syringeable.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

IV. Methods of Treatment

The antibodies or the antibody compositions provided herein can be used to treat, ameliorate, or prevent diseases, disorders, or symptoms described herein. The antibodies or the antibody compositions provided herein can be used to treat, ameliorate, or prevent diseases, disorders, or symptoms associated with inflammation and/or autoimmunity. In certain embodiments, the compositions and methods provided herein involve administering an antibody or an antibody composition provided herein, optionally in combination with a second or additional therapy.

The antibodies or the antibody compositions provided herein may be used to treat inflammatory diseases, such as inflammatory bowel disease (e.g., Crohn's disease and/or ulcerative colitis), allergy, acute or chronic reactive airway disease, allergic rhinitis, allergic dermatitis, atopic diseases, atopic asthma, atopic dermatitis, bronchial asthma, eosinophil invasive asthma, chronic obstructive pulmonary diseases, arthritis, rheumatoid arthritis, psoriatic arthritis, ankylosing spondylitis, primary biliary cirrhosis, systemic lupus erhythematosus, psoriasis, atherosclerosis, osteoporosis, and/or multiple sclerosis.

The antibodies or the antibody compositions provided herein may be used to treat autoimmune diseases, such as multiple sclerosis, rheumatoid arthritis, autoimmune hemolytic anemia, autoimmune neonatal thrombocytopenia, idiopathic thrombocytopenia purpura (ITP), autoimmunocytopenia, hemolytic anemia, antiphospholipid syndrome, dermatitis, allergic encephalomyelitis, myocarditis, relapsing polychondritis, rheumatic heart disease, neuritis, uveitis ophthalmia, Polyendocrinopathies, purpura (e.g., Henloch-Scoenlein purpura), Reiter's Disease, Stiff-Man Syndrome, autoimmune pulmonary inflammation, Autism, Guillain-Barre Syndrome, insulin dependent diabetes mellitus, and autoimmune inflammatory eye disorders, autoimmune thyroiditis, hypothyroidism (i.e., Hashimoto's thyroiditis), systemic lupus erhythematosus, Goodpasture's syndrome, Pemphigus, receptor autoimmunities (e.g., Graves' Disease, Myasthenia Gravis, and insulin resistance), autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, chronic renal failure, glomerulonephritis, nephrosis, IgA nephropathy, bullous pemphigoid, Sjogren's syndrome, adrenergic drug resistance (asthma or cystic fibrosis), chronic active hepatitis, primary biliary cirrhosis, other endocrine gland failure, vitiligo, vasculitis, post-MI, cardiotomy syndrome, urticaria, atopic dermatitis, inflammatory myopathies, and other inflammatory, granulamatous, degenerative, and atrophic diseases.

In some aspects, provided herein are methods of treating an inflammatory bowel disease (IBD) in a subject by administering an anti-TNFRSF25 antibody provided herein to the subject. The IBD may be Crohn's Disease (CD) or ulcerative colitis (UC). The IBD may be a severe form of IBD, which may be characterized by a subclinical phenotype. The IBD may be a moderate to severe form of IBD. The IBD may be a moderate form of IBD.

Subclinical phenotypes of IBD may include, but are not limited to, non-stricturing, stricturing, stricturing and penetrating, and isolated internal penetrating, disease, and perianal CD (pCD). Stricturing is the progressive narrowing of the intestine. Internal penetrating disease creates abnormal passageways (fistulae) between the bowel and other structures. pCD is a form of Crohn's disease that causes inflammation around the anus.

The IBD may be refractory. The term "refractory," as used herein, refers to the failure of a standard treatment to induce remission of a disease. Non-limiting examples of standard treatment include glucocorticosteriods, anti-TNF therapy, anti-a4-b7 therapy (vedolizumab), anti-IL12p40 therapy (ustekinumab), Thalidomide, and Cytoxin.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of at least one antibody that targets TNFRSF25, either alone or in combination with other therapies.

The term "subject" as used herein refers to any individual or patient to which the subject methods are performed. Generally, the subject is human, although as will be appreciated by those in the art, the subject may be an animal. Thus, other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of Crohn's disease may involve, for example, a reduction in Crohn's Disease Activity Index (CDAI) score. Treatment of ulcerative colitis may refer to an improvement in Mayo score, Mayo stool frequency subscore and/or Mayo endoscopy subscore and/or histologic-endoscopic mucosal improvement and/or endoscopic normalization and/or ulcerative colitis disease activity index and/or ulcerative colitis endoscopic index of severity.

The term "Crohn's Disease Activity Index" or "CDAI" includes a research tool used to quantify the symptoms of patients with Crohn's disease. The CDAI is generally used to define response or remission of CD. The CDAI consists of eight factors, each summed after adjustment with a weighting factor. The components of the CDAI and weighting factors are the following:

| Clinical or laboratory variable | Weighting factor |
|---|---|
| Number of liquid or soft stools each day for seven days | ×2 |
| Abdominal pain (graded from 0-3 on severity) each day for seven days | ×5 |
| General wellbeing, subjectively assessed from 0 (well) to 4 (terrible) each day for seven days | ×7 |
| Presence of complications* | ×20 |
| Taking Lomitil or opiates for diarrhea | ×30 |
| Presence of an abdominal mass (0 as none, 2 as questionable, 5 as definite) | ×10 |
| Hematocrit of <0.47 in men and <0.42 in women | ×6 |
| Percentage deviation from standard weight | ×1 |

*One point each is added for each set of complications: the presence of joint pains (arthralgia) or frank arthritis; inflammation of the iris or uveitis; presence of erythema nodosum, pyoderma gangrenosum, or aphthous ulcers; anal fissures, fistulae or abscesses; other fistulae; and/or fever during the previous week.

Remission of Crohn's disease is typically defined as a fall in the CDAI of less than 150 points. Severe disease is typically defined as a value of greater than 450 points. In certain aspects, response to a particular medication in a Crohn's disease patient is defined as a fall of the CDAI of greater than 70 points.

As used herein, "Mayo score" refers to an index system for assessing the severity of a ulcerative colitis disease condition. See Schoeder et al., N Engl J Med 1987; 317: 1625-9. The Mayo score ranges from 0-12, with sub-scores of 0-3, where the higher scores indicate more severe disease. In some aspects, sub-scores may be rated for stool frequency, rectal bleeding, mucosal appearance at endoscopy, and physician's global assessment (PGA).

As used herein, "ulcerative colitis endoscopic index of severity" or "UCEIS" refers to an index for assessing endoscopic disease activity. The index assesses three criteria, including vascular pattern, bleeding, and erosions and ulcers. See Travis et al., Gut., 61(4):535-42 (2012). A higher score reflects increased disease severity.

As used herein, "ulcerative colitis disease activity index" or "UCDAI" refers to an index system for assessing the symptomatic severity or response of an ulcerative colitis patient. The index assesses four variables, which include stool frequency, severity of bleeding, colonic mucosal appearance, and the physician's overall assessment of disease activity. See Sutherland et al., Gastroenterology. 1987; 92:1894-8. Each variable is scored from 0-3 so that the total index score ranges from 0-12; 0-2: remission; 3-6: mild; 7-10: moderate; >10: severe ulcerative colitis.

In addition to being used as a monotherapy, the antibodies of the present invention may also find use in combination therapies. Effective combination therapy may be achieved with a single composition or pharmacological formulation that includes both agents, or with two distinct compositions or formulations, administered at the same time, wherein one composition includes at least one antibody of this invention, and the other includes the second agent(s). Alternatively, the antibody therapy may precede or follow the other agent treatment by intervals ranging from minutes to months.

Various combinations may be employed, such as when an antibody of the present invention is "A" and "B" represents a secondary agent, non-limiting examples of which are described below:

A/B/A B/A/B B/B/A A/A/B A/B/B B/A/A A/B/B/B B/A/ B/B B/B/B/A B/B/A/B A/A/B/B A/B/A/B A/B/B/A B/B/A/A B/A/B/A B/A/A/B A/A/A/B B/A/A/A A/B/ A/A A/A/B/A

In various aspects, the anti-TNFRSF25 antibody is administered to the subject in a series of treatments. The anti-TNFRSF25 antibody and a second treatment may be administered in any order or concurrently. The anti-TNFRSF25 antibody may be administered to patients that have previously undergone treatment with the second treatment. The anti-TNFRSF25 antibody and the second treatment may be administered substantially simultaneously or concurrently. For example, a subject may be given the anti-TNFRSF25 antibody while undergoing a course of treatment with the second treatment. The anti-TNFRSF25 antibody may be administered within 1 year of the treatment with the second treatment. The anti-TNFRSF25 antibody may be administered within 10, 8, 6, 4, or 2 months of any treatment with the second treatment. The anti-TNFRSF25 antibody may be administered within 4, 3, 2, or 1 week of any treatment with the second treatment. The anti-TNFRSF25 antibody may be administered within 5, 4, 3, 2, or 1 days of any treatment with the second treatment. The two treatments may be administered to the subject within a matter of hours or minutes (i.e., simultaneously).

Other treatments include, but are not limited to 1) anti-inflammatory drugs (e.g., Aminosalicylates such as, but not limited to sulfasalazine Azulfidine, 5-aminosalicylates, Mesalamine, Asacol, Lialda, Rowasa, Canasa, balsalazide Colazal and olsalazine, Dipentum); 2) corticosteroids (e.g., prednisone and hydrocortisone); 3) immune system suppressors (e.g., Azathioprine, Azasan, Imuran, mercaptopurine, Purinethol, Purixan, Cyclosporine, Gengraf, Neoral and Sandimmune, Infliximab, Remicade, adalimumab, Humira, golimumab, and Simponi, tumor necrosis factor (TNF)-alpha inhibitors (e.g., Infliximab), Methotrexate, Rheumatrex, Natalizumab, Tysabri, vedolizumab, Entyvio, Ustekinumab and Stelara; 4) Antibiotics (e.g., Metronidazole, Flagyl, Ciprofloxacin, Cipro); 5) Anti-diarrheal medications (e.g., fiber supplements—Metamucil or Citrucel) or loperamide; 6) Pain relievers (e.g., Tylenol, ibuprofen, naproxen sodium and diclofenac sodium); and 7) Surgery (e.g., removal of the colon, partial digestive tract removal, colectomy, proctocolectomy and/or strictureplasty). In some embodiments, these treatments may be administered in combination with the anti-TNFRSF25 antibody. Treatment with an antibody can occur prior to, concurrently with, or subsequent to administration of another treatment. Combined administration can include co-administration, either in a single pharmaceutical formulation or using separate formulations, or consecutive administration in either order but generally within a time period such that all active agents can exert their biological activities simultaneously. Any dosing schedules for such treatments can also be used as determined by the skilled practitioner.

In some embodiments, the second treatment comprises another antibody. Thus, treatment can involve the combined administration of antibodies provided herein with other antibodies against additional antigens, such as, but not limited to tumor necrosis factor (TNF)-alpha. Combined administration can include co-administration, either in a single pharmaceutical formulation or using separate formulations, or consecutive administration in either order but generally within a time period such that all active agents can exert their biological activities simultaneously.

V. Methods of Detection

The present disclosure also concerns immunodetection methods for detecting human TNFRSF25. A wide variety of assay formats are contemplated for detecting protein products, including immunohistochemistry, enzyme linked immunosorbent assay (ELISA), radioimmunoassay (RIA), immunoradiometric assay, fluoroimmunoassay, chemiluminescent assay, bioluminescent assay, dot blotting, FACS analyses, and Western blot to mention a few. The steps of various useful immunodetection methods have been described in the scientific literature. In general, the immunobinding methods include obtaining a sample, and contacting the sample with an antibody specific for the protein to be detected, as the case may be, under conditions effective to allow the formation of immunocomplexes. In general, the detection of immunocomplex formation is well known in the art and may be achieved through the application of numerous approaches. These methods are generally based upon the detection of a label or marker, such as any of those radioactive, fluorescent, biological and enzymatic tags. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

As used herein, the term "sample" refers to any sample suitable for the detection methods provided by the present invention. The sample may be any sample that includes material suitable for detection or isolation. Sources of samples include blood, pleural fluid, peritoneal fluid, urine, saliva, malignant ascites, broncho-alveolar lavage fluid, synovial fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer. In some aspects, the biological sample comprises a plurality of cells. In certain aspects, the biological sample comprises fresh or frozen tissue. In specific aspects, the biological sample comprises formalin fixed, paraffin embedded tissue. In some aspects, the biological sample is a tissue biopsy, fine needle aspirate, blood, serum, plasma, cerebral spinal fluid, urine, stool, saliva, circulating tumor cells, exosomes, or aspirates and bodily secretions, such as sweat. In some aspects, the biological sample contains cell-free DNA.

VI. Kits

Also provided herein are kits containing therapeutic agents and/or other therapeutic and delivery agents. In some embodiments, a kit is provided for preparing and/or administering a therapy of the embodiments. The kit may comprise one or more sealed vials containing any of the pharmaceutical compositions of the present embodiments. The kit may include, for example, at least one anti-TNFRSF25 antibody, as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

Also provided are immunodetection kits for use with the immunodetection methods described above. As the antibodies may be used to detect TNFRSF25, the antibodies may be included in the kit. The immunodetection kits will thus comprise, in suitable container means, a first antibody that binds to TNFRSF25, and optionally an immunodetection reagent.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
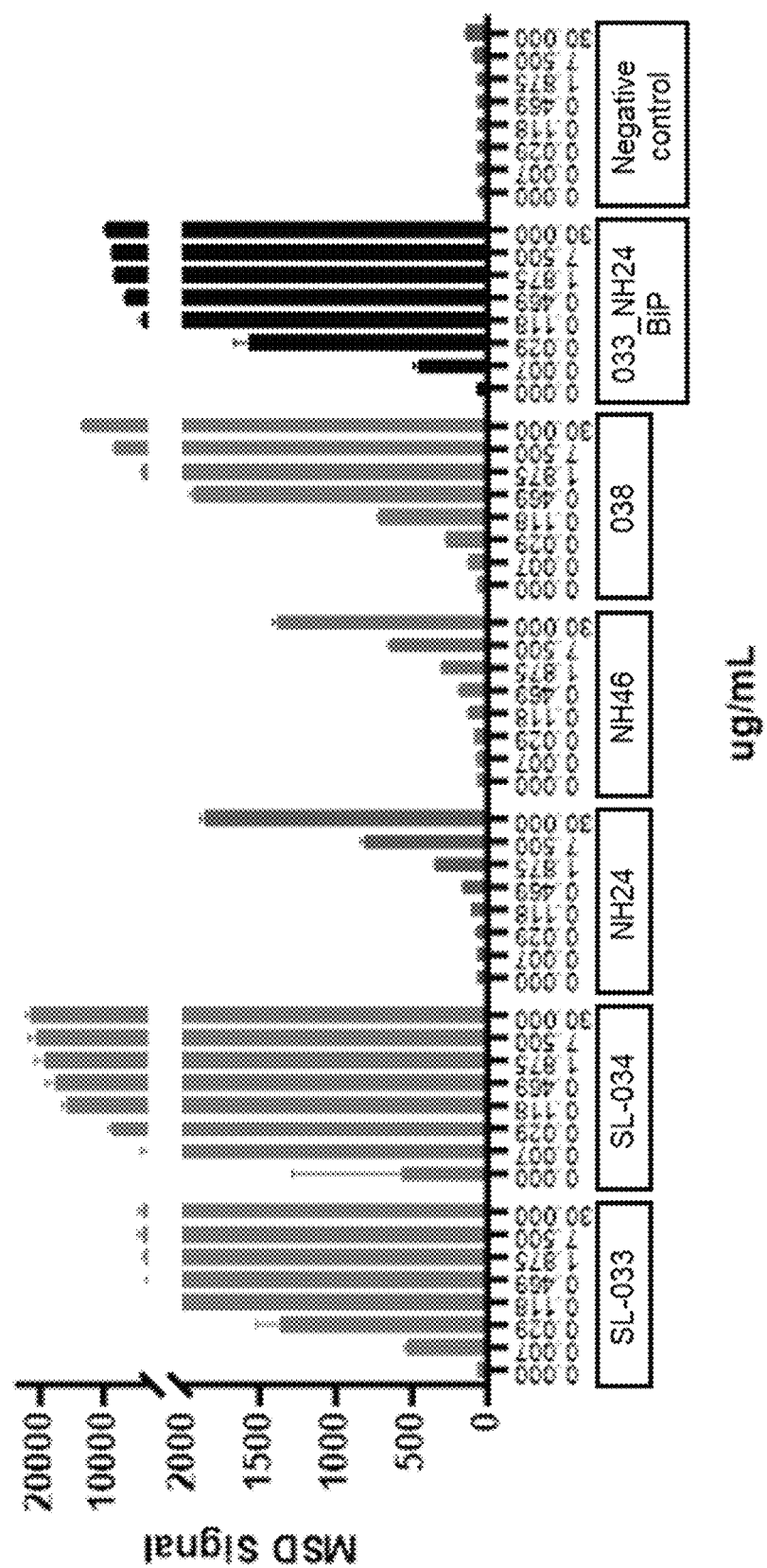
FIG. 1. MSD plate analysis of antibody binding to recombinant biotin-conjugated human TNFRSF25 protein. Recombinant biotin-conjugated human TNFRSF25 protein was immobilized onto a streptavidin-coated MSD plate and allowed to bind the anti-TNFRSF25 mAbs in solution. Following a washing step, the bound antibodies were detected using a sulfo-tagged anti-human Fc antibody.

Provided herein are monoclonal and biparatopic antibodies that specifically target human TNFRSF25. The monoclonal antibodies were produced in an engineered CHOK1 cell-line by transfecting the cells with vectors genetically encoding the Heavy and Light chain antibody sequences followed by a single-step affinity-capture chromatography using FcXL resins. The final monoclonal antibody preparation was buffer exchanged into PBS, pH 7.4. Production of biparatopic antibodies followed a two-step process. In the first step of the process, the so called Knob-half (or Hole-half) antibody was produced by transfecting an engineered CHOK1 cell-line with vectors genetically encoding the Knob (or the Hole) Heavy chain and the corresponding Light chain sequences. The CHOK1-cell-harvest from the Knob-half antibody and Hole half-antibody was then purified by Protein A column-based chromatography. In the second step of the process, the two half-antibodies were reassembled into the desired biparatopic format by the use of a mild reduction step followed by quenching the reaction with buffer exchange into PBS, pH 7.4. To detect binding of the antibodies to human TNFRSF25, recombinant biotin-conjugated human TNFRSF25 protein was immobilized onto a streptavidin-coated MSD (Meso Scale Discovery) plate and allowed to bind the anti-TNFRSF25 mAbs in solution. Following a washing step, the bound antibodies were detected using a sulfo-tagged anti-human Fc antibody. The results of these MSD assays are shown in arbitrary units (au) on the y-axis of FIG. 1. To determine the binding affinity of the antibodies to recombinant human TNFRSF25 protein, recombinant biotin-conjugated human TNFRSF25 protein was immobilized onto a streptavidin-coated BLI sensor and allowed to bind the anti-TNFRSF25 mAbs in solution phase. The binding affinity ($K_D$) was calculated using the on-rates (Ka) and off-rates (Kd) of mAb binding to the target using a 1:1 Langmuir binding model in the ForteBio data analysis software. The results of these BLI/Octet assays are shown in Table 7.

TABLE 7

| Binding Affinity of Anti-TNFRSF25 Abs to Recombinant Human TNFRSF25 Protein Determined by BLI/Octet to SPR as indicated [units in nM] | | | | | | | |
|---|---|---|---|---|---|---|---|
| | 033 | 034 | 061 [SPR] | NH24 | NH46 | 038 | 033_NH24 |
| KD (nM) | <1 | <1 | 0.00136 | 0.59 | 0.185 | 3.6 | 0.14 |

Figure 2A:
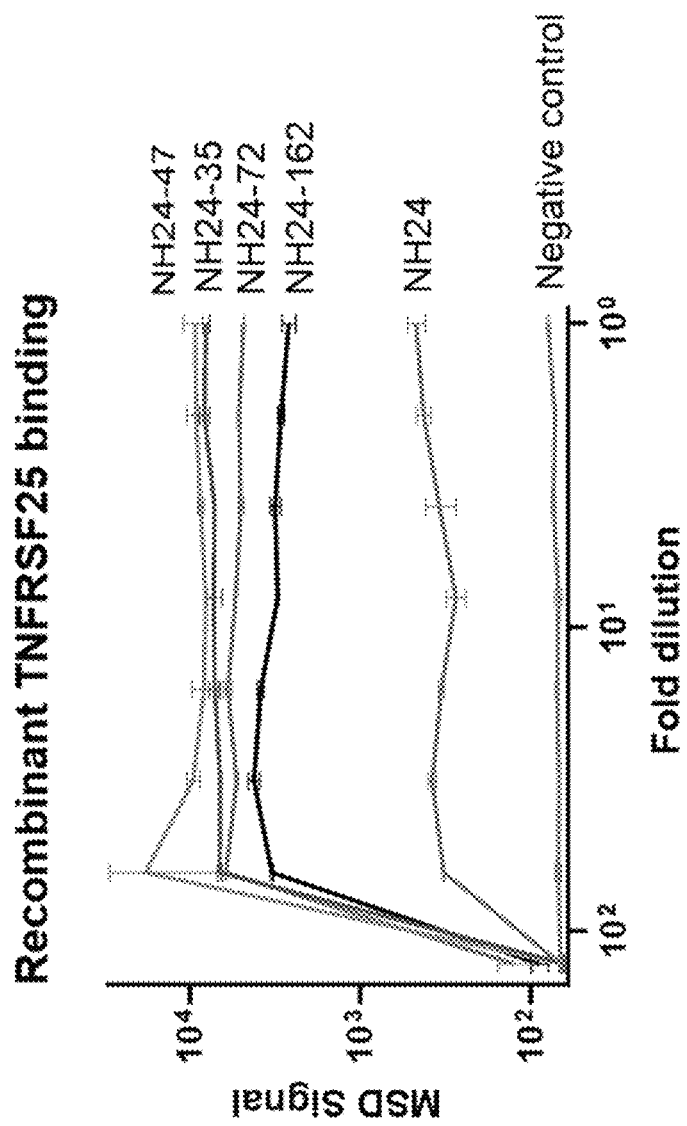
FIGS. 2A-2B. Recombinant TNFRSF25 binding and TL1A blocking by NH24 scFv variants.
Figure 2B:
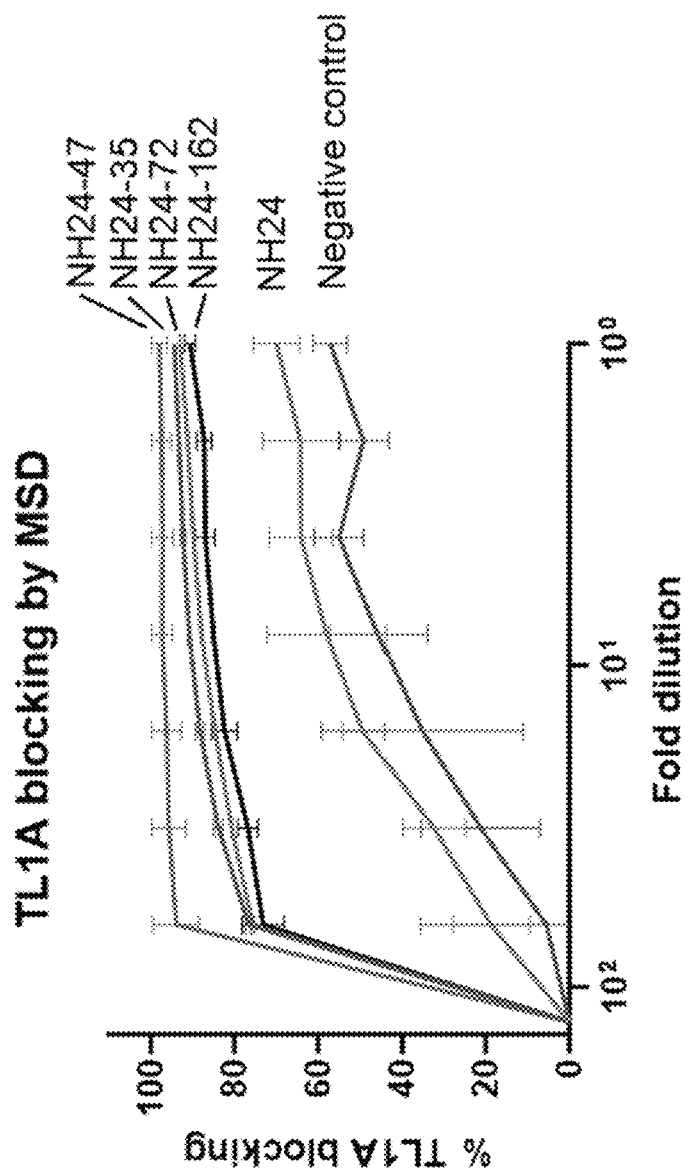

Affinity-matured NH24 variants were expressed in *E. coli* periplasm in their scFv format and expression was induced overnight. Supernatants from the overnight *E. coli* culture were collected as the unpurified scFv, which was used to test binding to recombinant human TNFRSF25 and the ability to block recombinant human TL1A binding to TNFRSF25. Compared to the original NH24 clone, all four variants tested exhibited much higher level of binding to TNFRS25 (FIG. 2A). Significantly higher blocking by affinity-matured scFv's were observed compared to the original NH24 clone (FIG. 2B).

Figure 3A:
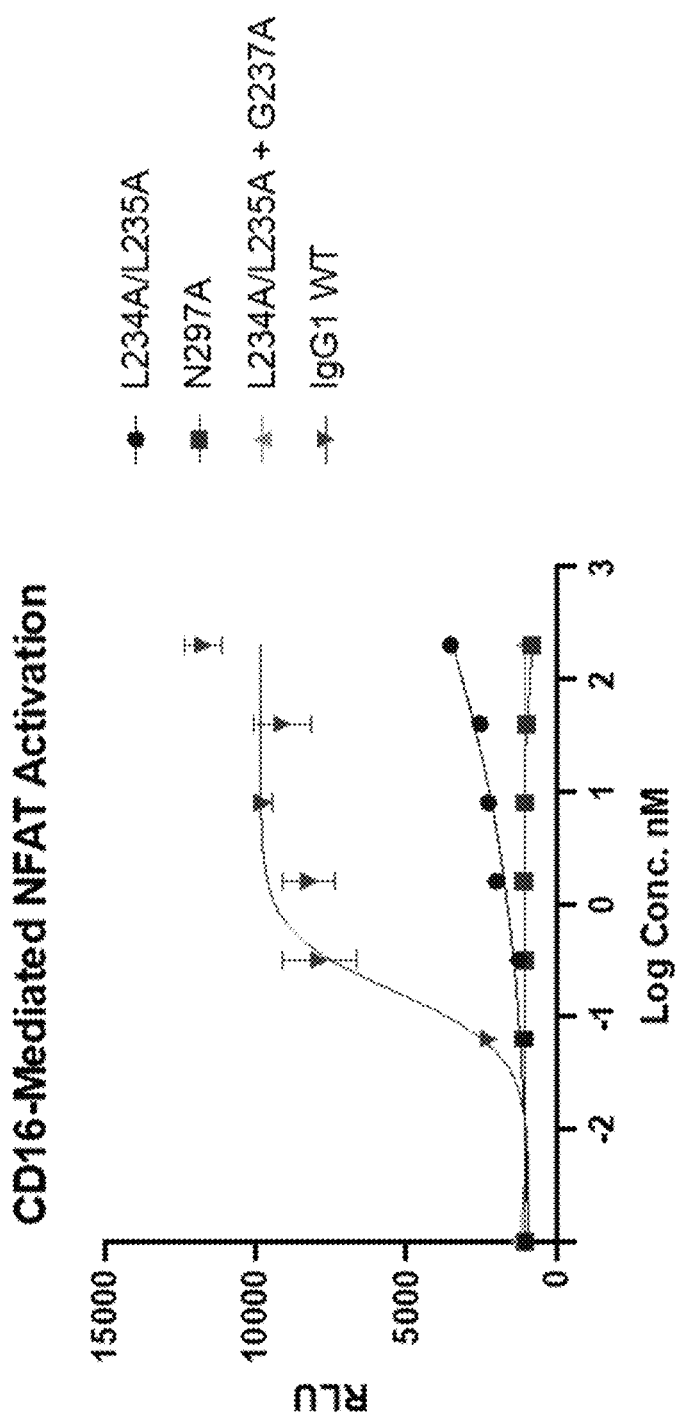
FIGS. 3A-3C. Evaluation of anti-TNFRSF25 antibodies containing various IgG1 Fc-silencing mutations.
Figure 3B:
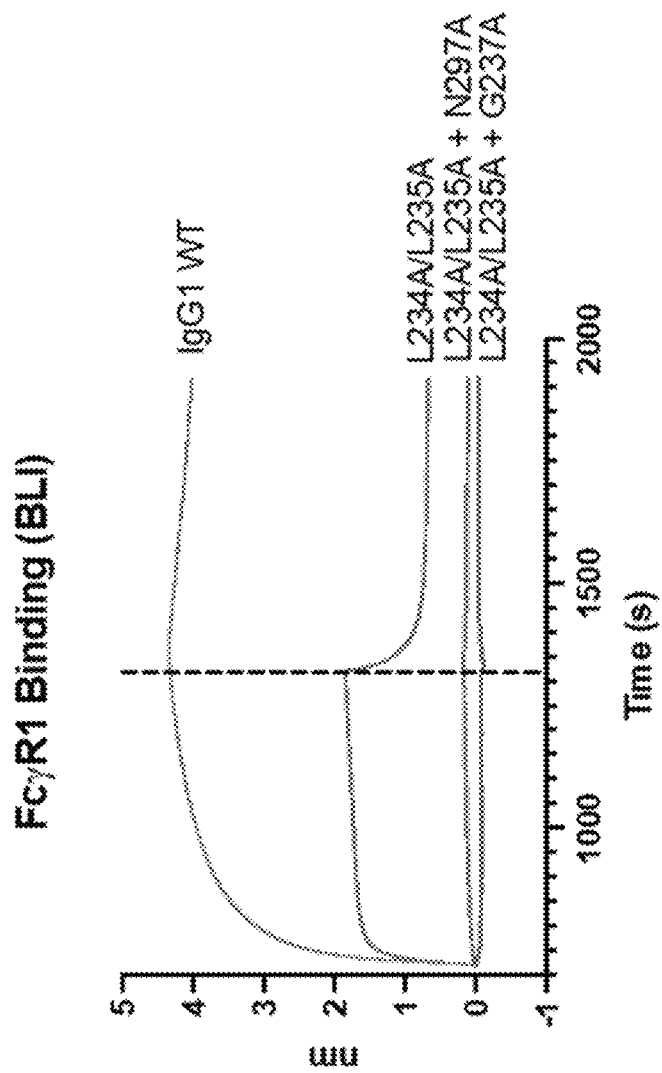
Figure 3C:
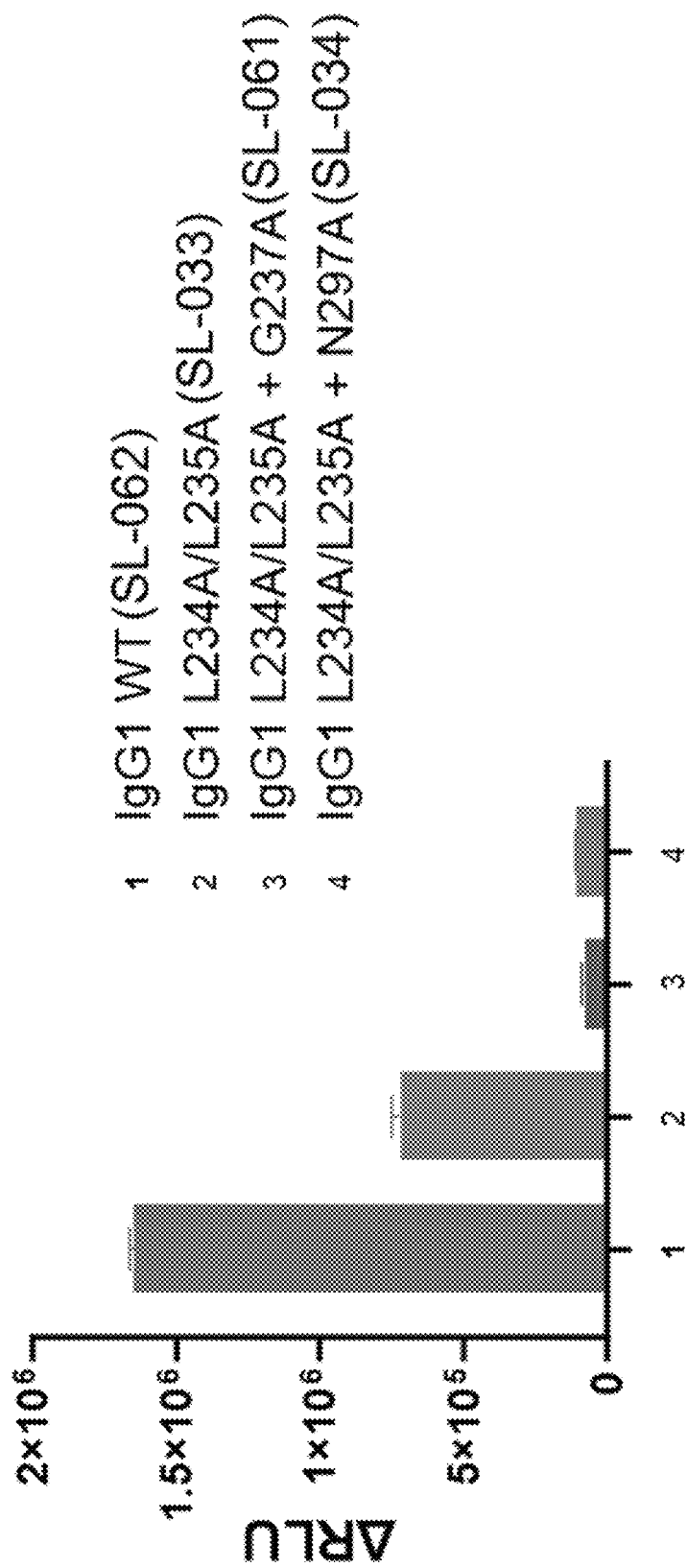

The effects of various IgG1 Fc-silencing mutations were evaluated in the anti-TNFRSF25 antibodies. For this, anti-TNFRSF25 antibodies containing various Fc-silencing mutations (L234A/L235A [clone 033], L234A/L245A+N297A [clone 034], L234A/L235A+G237A [clone 061]) in the IgG1-Fc domain were generated. To evaluate Fc-mediated antibody-dependent cellular cytotoxicity (ADCC) activity by the anti-TNFRSF25 variants, antibodies were first incubated with CHOK1 cells expressing TNFRSF25 for 1 hr. Antibody-opsonized CHOK1 cells were further incubated with Jurkat cells expressing cell surface Fc receptor FcγRIIIa (CD16A) and NFAT-Luciferase reporter gene at 1:4 ratio. Luciferase activity resulting from CD16-mediated NFAT activation was measured after 6 hours using a luminometer. Fc-mediated ADCC activity was significantly reduced or silenced in anti-TNFRSF25 variants compared to mAb containing wild-type sequence of IgG1-Fc domain [clone 062] (FIG. 3A). In addition, lack of FcγR1 (CD64) binding of anti-TNFSF25 antibodies containing Fc-silencing mutations were confirmed by BLI (FIG. 3B) to minimize/eliminate the risk of anti-TNFRSF25 crosslinking that could occur via Fcγ receptor binding following engagement of the DR3 receptor on cells. FIG. 3C demonstrates that an Fc-competent (IgG1 WT) anti-TNFRSF25 antibody (SL-062) is capable of activating the NFkB pathway through the concomitant binding of DR3 (on Jurkat reporter cells) and the FcγR1(CD64) receptor (on engineered HEK293 cells). SL-033, that maintains residual FcγR1 binding (FIG. 3B), was capable of activating the NFkB pathway albeit to a lesser extent than SL-062, while the fully Fc-silent anti-TNFRSF25 antibodies (SL-034 and SL-061) did not activate the DR3-driven NFkB pathway.

Figure 4:
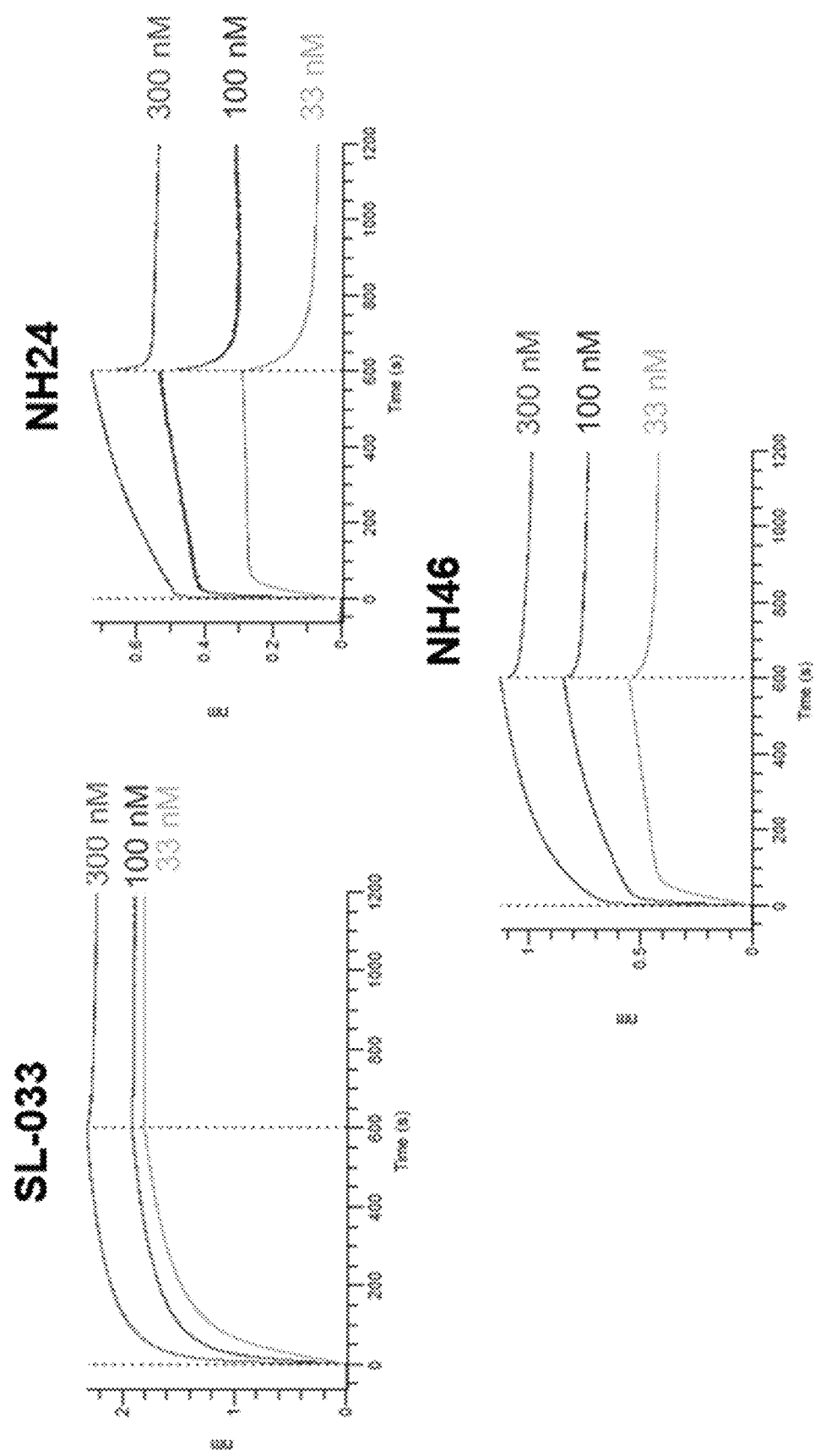
FIG. 4. TNFRSF25 binding affinity of anti-TNFRSF25 antibodies. BLI assay was performed using the Octet Red 96e instrument. Streptavidin biosensors were loaded with biotinylated recombinant human TNFRSF25-His tagged (Acro #TN5-H52H3) as the ligand. During the association phase, biosensors were incubated with anti-TNFRSF25 antibodies at various concentrations for 600 seconds, followed by a 600-second dissociation phase.

To detect binding of certain whole antibodies to human TNFRSF25, streptavidin biosensors were loaded with biotinylated recombinant human TNFRSF25-His tagged (Acro #TN5-H52H3) as the ligand. During the association phase, biosensors were incubated with anti-TNFRSF25 antibodies at various concentrations for 600 seconds, followed by a 600 second dissociation phase. The TNFRSF25 binding affinities of whole antibody SL-033 [clone 033], NH24, and NH46 (each having L234A/L235A G1 constant region substitutions) are provided in FIG. 4 and Table 8.

TABLE 8

Binding Affinity of Anti-TNFRSF25
Whole Antibodies to Recombinant Human
TNFRSF25 Protein Determined by BLI/Octet

|  | SL-033 | NH24 | NH46 |
|---|---|---|---|
| Response (RU) | 2.19 | 0.73 | 1.06 |
| Kon ($M^{-1}s^{-1}$) | 2.43E+05 | 1.26E+06 | 4.52E+05 |
| Koff ($s^{-1}$) | <1.0E−07 | 7.42E−04 | 8.54E−05 |

Figure 5A:
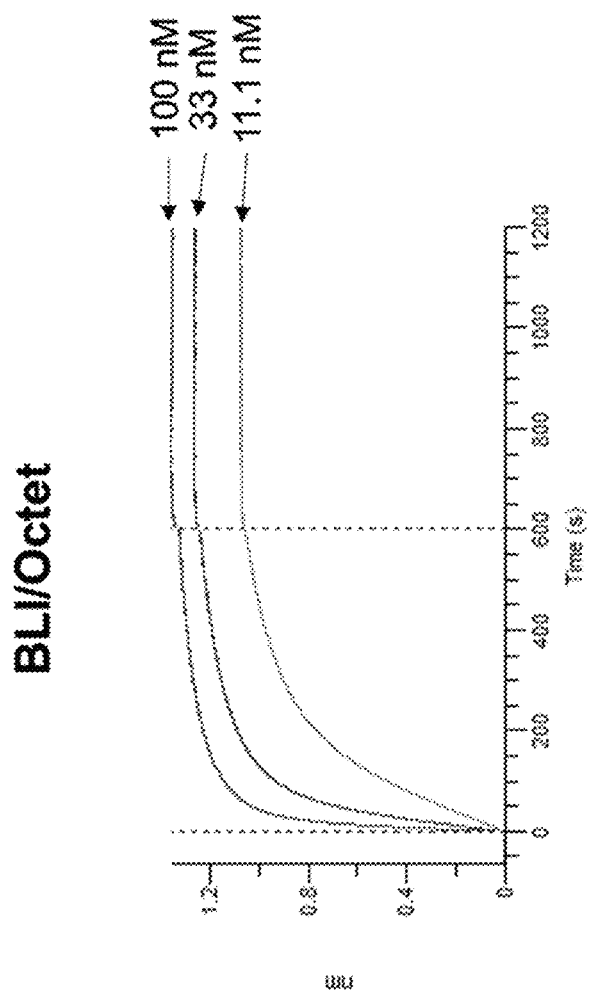
FIGS. 5A-5C. TNFRSF25 binding affinity of SL-061 (L234A/L235A+G237A) by BLI/Octet and SPR.
Figure 5B:
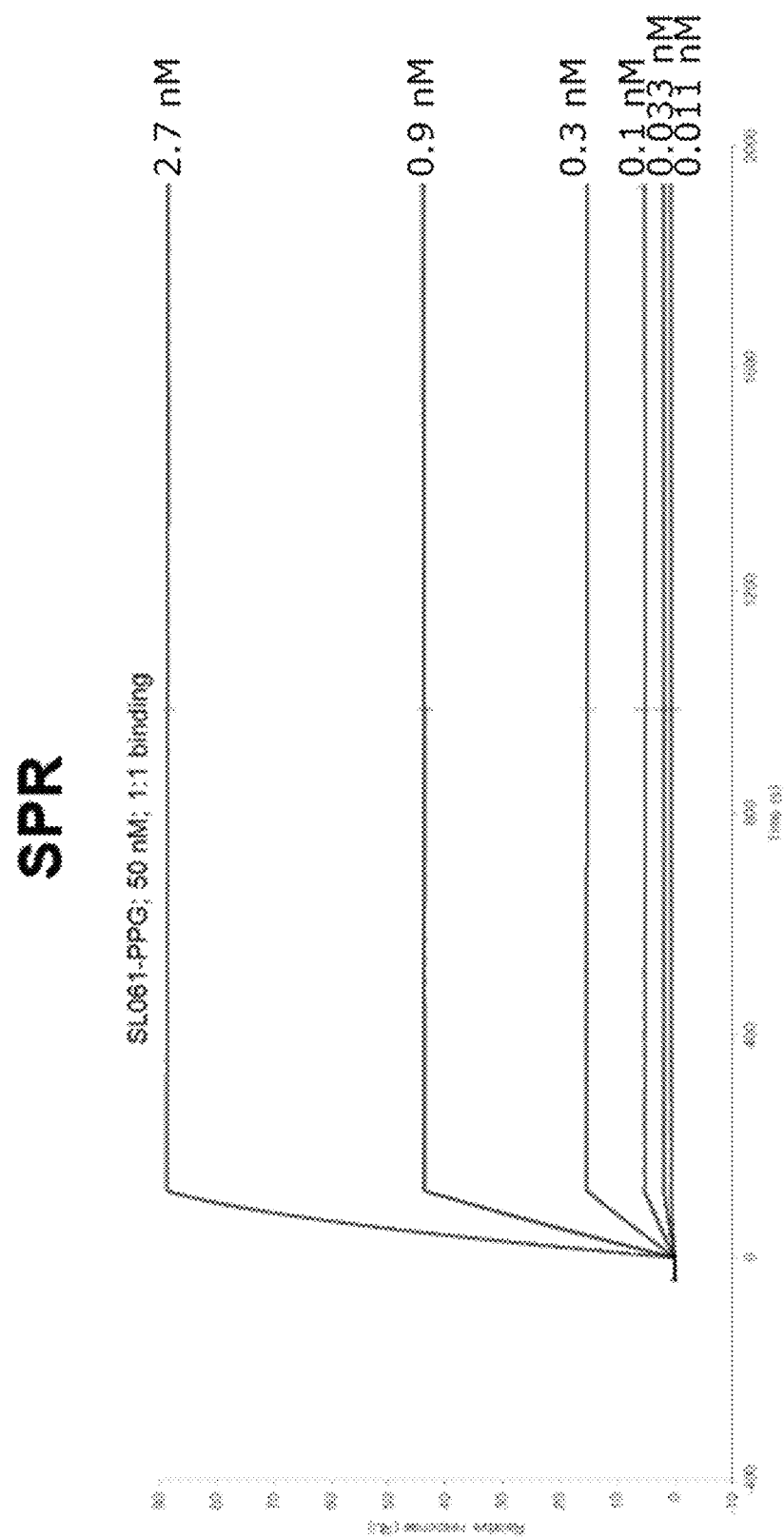
Figure 5C:
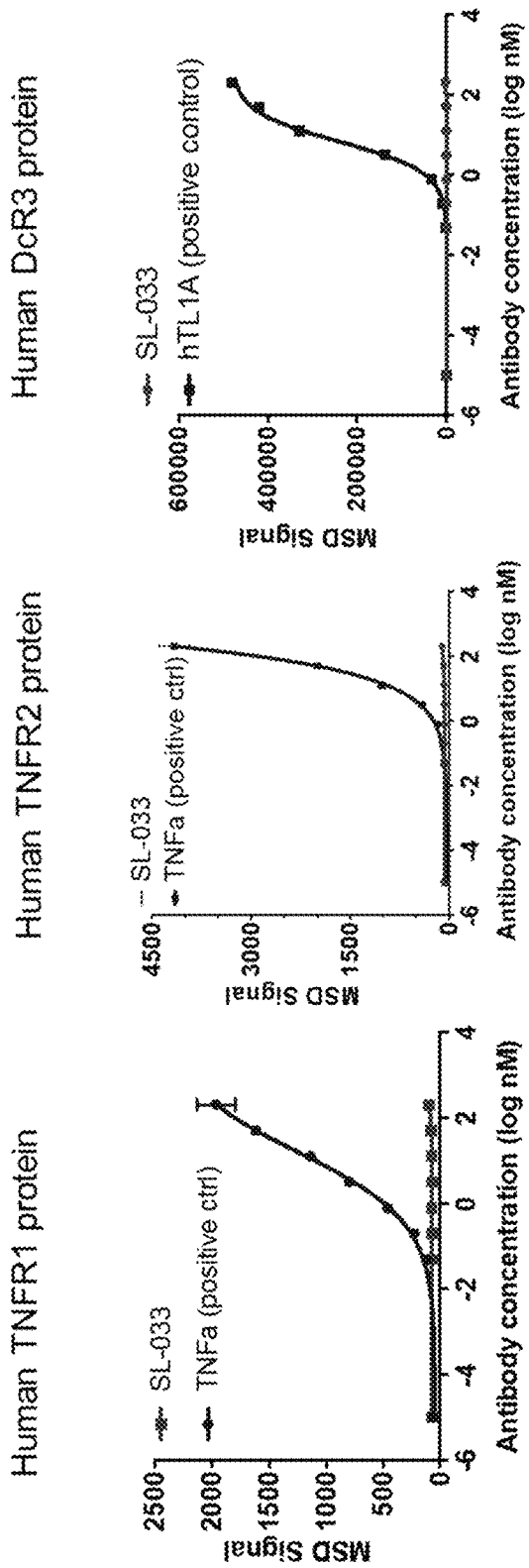

To detect binding of L234A/L235A+G237A [clone 061] antibodies to human TNFRSF25, streptavidin biosensors were loaded with biotinylated recombinant human TNFRSF25-His tagged (Acro #TN5-H52H3) as the ligand. During the association phase, biosensors were incubated with L234A/L235A+G237A [clone 061] antibodies at the concentrations indicated in FIG. 5A for 600 seconds, followed by a 600-second dissociation phase. Complete kinetic parameters were indeterminable by BLI. SPR was performed using biotinylated recombinant human TNFRSF25-His tagged (Acro #TN5-H52H3) loaded on a streptavidin sensor chip SA (Cytiva) at 50 nM, followed by flowing L234A/L235A+G237A [clone 061] antibodies at the concentrations indicated in FIG. 5B for an association phase of 2 min and then for a dissociation phase of 30 min. $K_d$ was estimated to be 1.36 pM ($k_{on}$=2.85E6 l/Ms and $k_{off}$=3.89E-6 l/s) as analyzed by Biacore Insight Evaluation software for a 1:1 binding stoichiometry. As shown in FIG. 5C, no binding to DcR3, TNFR1 or TNFR2 was observed by MSD for SL-033. SL-061 also does not bind to DcR3, TNFR1 or TNFR2.

Figure 5D:
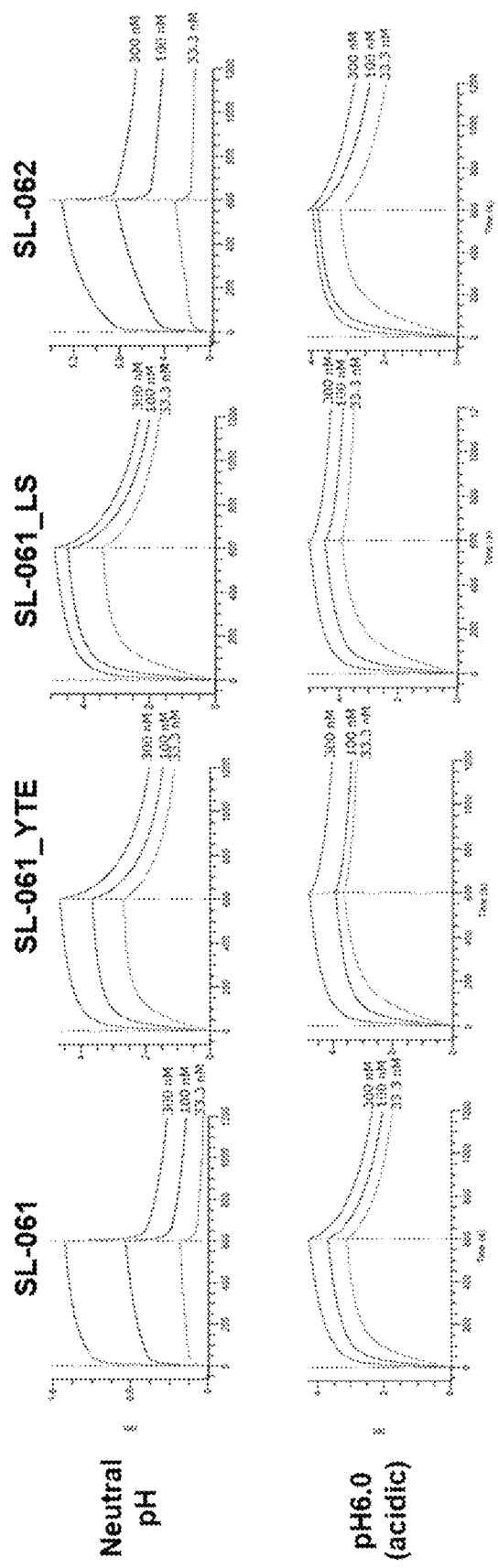
FIG. 5D. FcRn binding kinetics by anti-TNFRSF25 antibodies. BLI assay was performed using the Octet Red 96e instrument. Streptavidin biosensors were loaded with biotinylated recombinant human(h) FcRn-His tagged protein (Acro #FCM-H82W7) as the ligand. During the association phase, biosensors were incubated with anti-DR3 candidate antibodies at various concentrations for 600 seconds, followed by a 600-second dissociation phase. Both SL061_YTE and SL061_LS have approximately 10-fold improvement in binding affinities to hFcRn at pH 6.0 (acidic) compared to pH 7.4 (neutral) which is arising primarily from their slower dissociation rate at pH 6.0.

To detect binding of certain whole antibodies to the neonatal Fc receptor (FcRn) at neutral and acidic pH conditions, streptavidin biosensors were loaded with biotinylated recombinant human FcRn-His tagged protein (Acro #FCM-H82W7) as the ligand. During the association phase, biosensors were incubated with anti-TNFRSF25 antibodies at various concentrations for 600 seconds, followed by a 600 second dissociation phase. The FcRn binding properties of whole antibody SL-061, SL-061_YTE, SL-061_LS, and SL-062 at neutral pH and acidic pH (pH 6.0) conditions are provided in FIG. 5D and Table 9. Both SL061_YTE and SL061_LS have approximately 10-fold improvement in binding affinities to FcRn at pH 6.0 (acidic) compared to pH 7.4 (neutral), which is arising primarily from their slower dissociation rate at pH 6.0.

TABLE 9

Binding Affinity of Anti-TNFRSF25
Whole Antibodies to Recombinant Human
FcRn Protein Determined by BLI/Octet

| mAb | $K_D$(M) | $K_{on}$(1/M · sec) | $K_{off}$(1/sec) |
|---|---|---|---|
| FcRn Binding at neutral pH 7.4 ||||
| SL-061 | 7.41E−9 | 4.41E5 | 3.27E−3 |
| SL-061_YTE | 8.08E−9 | 2.22E5 | 1.79E−3 |
| SL-061_LS | 6.78E−9 | 2.13E5 | 1.44E−3 |
| SL-062 | 6.54E−9 | 1.9E5 | 1.24−3 |
| FcRn Binding at acidic pH 6.0 ||||
| SL-061 | 4.41E−9 | 2.35E5 | 1.04E−3 |
| SL-061_YTE | 9.66E−10 | 2.00E5 | 1.93E−4 |
| SL-061_LS | 8.79E−10 | 2.06E5 | 1.81E−4 |
| SL-062 | 3.93E−9 | 1.82E5 | 7.15E−4 |

Figure 6:
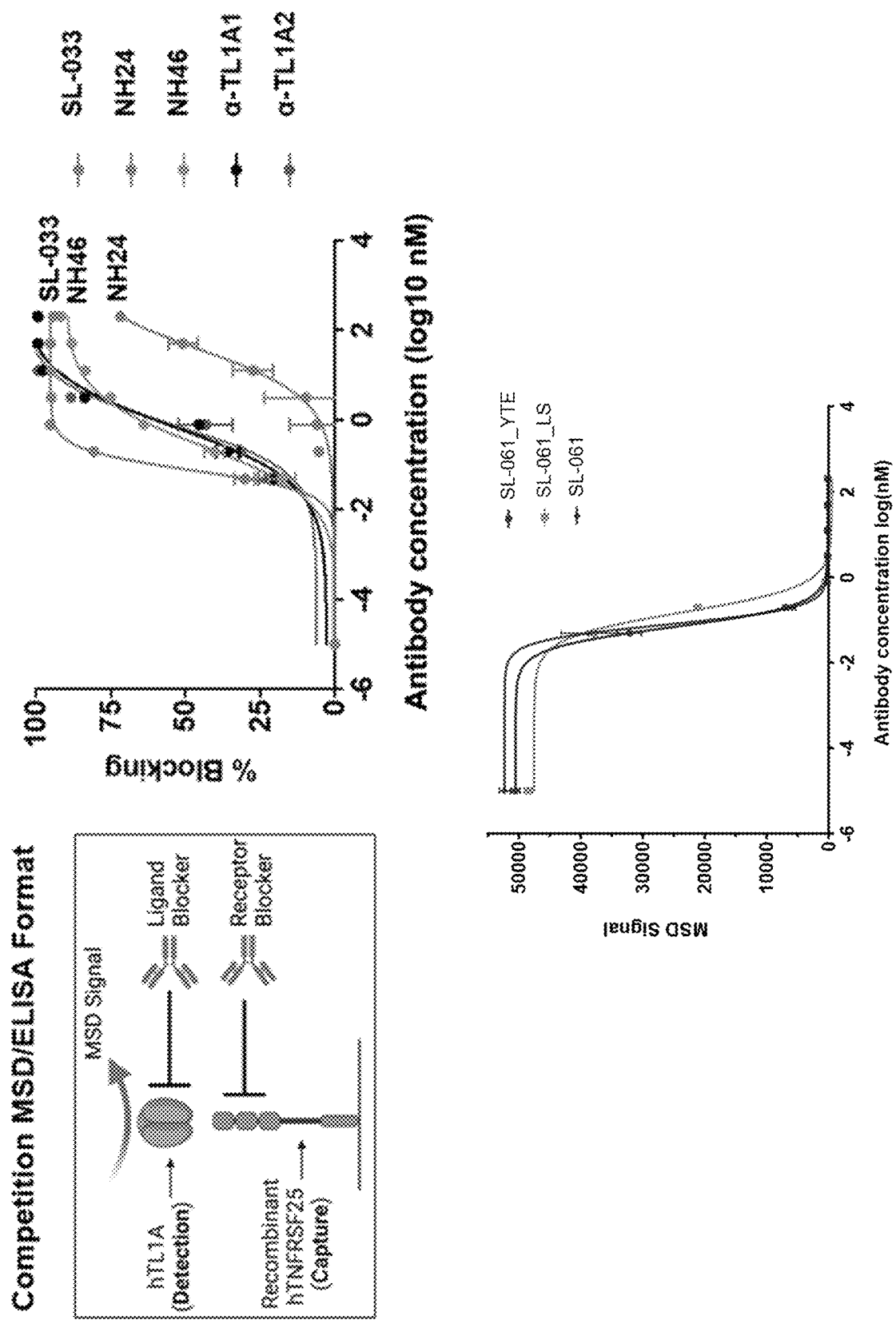
FIG. 6. TL1A blocking activity of anti-TNFRSF25 antibodies. Human TNFRSF25 was precoated on MSD assay plates followed by incubating with various concentrations of anti-TNFRSF25 antibodies. Plates were washed and incubated with a fixed concentration of TL1A-rabbit (r) Fc protein (0.4 μg/ml). For analysis of anti-TL1A benchmark antibody controls, anti-TL1A antibodies (labeled as α-TL1A1 and α-TL1A2) were first incubated with a fixed amount (0.4 μg/ml) of TL1A-rFc in a separate 96-well plate before adding to TNFRSF25-coated MSD plates. TNFRSF25:TL1A protein complexes were detected using a sulfo-tagged anti-rabbit secondary antibody. Raw MSD signals were normalized to no anti-DR3 (0 nM) wells to determine the % TL1A blocking (top right panel) or plotted as a function of anti-TNFRSF $\log_{10}$(nM) concentration (bottom panel).

To determine the TL1A blocking activity of certain whole antibodies to human TNFRSF25, recombinant biotin-conjugated human TNFRSF25 protein was immobilized onto a streptavidin-coated MSD (Meso Scale Discovery) plate and allowed to bind the anti-TNFRSF25 mAbs in solution. Following a washing step, the plates were incubated with a fixed concentration of TL1A-rabbit (r) Fc protein (0.4 μg/ml). For analysis of anti-TL1A benchmark antibody controls, anti-TL1A were first incubated with a fixed amount (0.4 μg/ml) of TL1A-rFc in a separate 96-well plate before adding to TNFRSF25-coated MSD plates. DR3:TL1A protein complexes were detected using a sulfo-tagged anti-rabbit secondary antibody. Raw MSD signals were normalized to no anti-TNFRSF25 (0 nM) wells to determine the % TL1A blocking. SL-033 was found to outperform anti-TL1As in blocking TL1A binding to DR3 (FIG. 6 and Table 10). SL-061 blocked recombinant TL1A binding to TNFRSF25 with an $IC_{50}$ of 0.056 nM by MSD. In addition, SL-061_YTE and SL-061_LS variants blocked TL1A binding to recombinant TNFRSF25 with similar potency as SL-061.

TABLE 10

TL1A Blocking Activity of
Anti-TNFRSF25 Whole Antibodies

|  | TL1A/TNFRSF25 Blocking $IC_{50}$ [nM] |  |
|---|---|---|
| SL-033 | 0.07 | Anti-DR3 |
| NH24 | 39.4 |  |
| NH46 | 0.26 |  |
| α-TL1A1 | 0.70 | Anti-TL1A |
| α-TL1A2 | 0.81 |  |

Figure 7A:
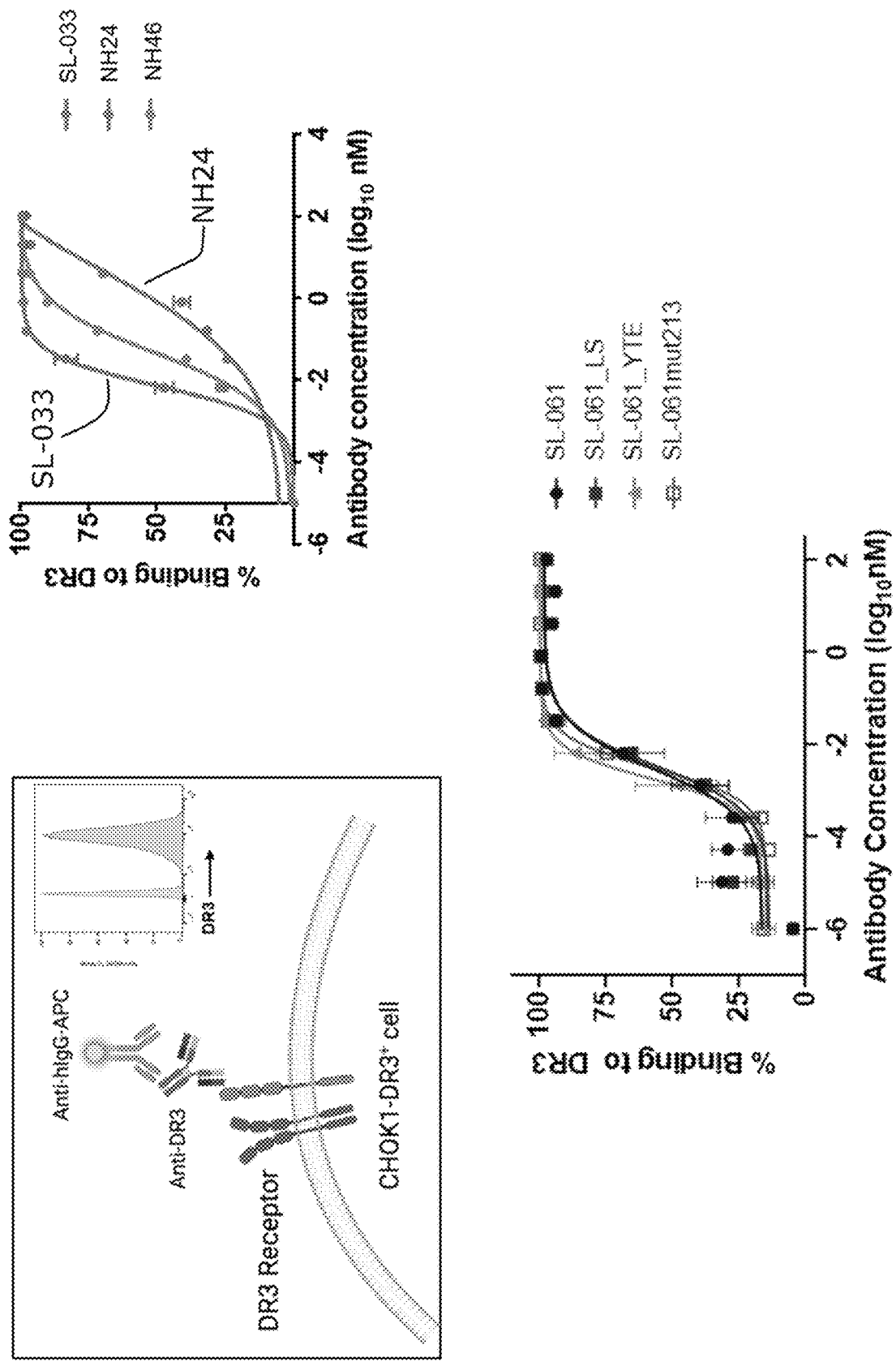
FIG. 7A. Native TNFRSF25 binding by anti-TNFRSF25 antibodies on CHOK1-TNFRSF25$^+$ cells by flow cytometry. Native TNFRSF25 binding was evaluated using a CHOK1 cell line engineered to over-express the human TNFRSF25 protein via stable transfection of a mammalian expression vector (pcDNA) encoding the human TNFRSF25 cDNA sequence (NP_683866). CHOK1-TNFRSF25$^+$ cells were incubated with various concentrations of anti-TNFRSF25 antibodies for 1 h at 4° C. Cells were washed and further incubated with APC-conjugated anti-human Fc antibody to detect antibody drug bound cells by flow cytometry.

Native TNFRSF25 binding was evaluated using a CHOK1 cell line engineered to over-express the human TNFRSF25 protein via stable transfection of a mammalian expression vector (pcDNA) encoding the human TNFRSF25 cDNA sequence (NP_683866). CHOK1-TNFRSF25+ cells were incubated with various concentrations of anti-TNFRSF25 antibodies for 1 h at 4° C. Cells were washed and further incubated with APC-conjugated anti-human Fc antibody to detect antibody drug bound cells by flow cytometry (FIG. 7A). SL-033 was found to bind more tightly to native TNFRSF25 than NH46 and NH24 (FIG. 7A and Table 11).

TABLE 11

Native TNFRSF25 Binding by Anti-TNFRSF25 Antibodies on CHOK1-TNFRSF25+ Cells by Flow Cytometry

| Binding to DR3 | SL-033 | NH46 | NH24 |
|---|---|---|---|
| EC50 nM | 0.007 | 0.05 | 4.6 |

Figure 7B:
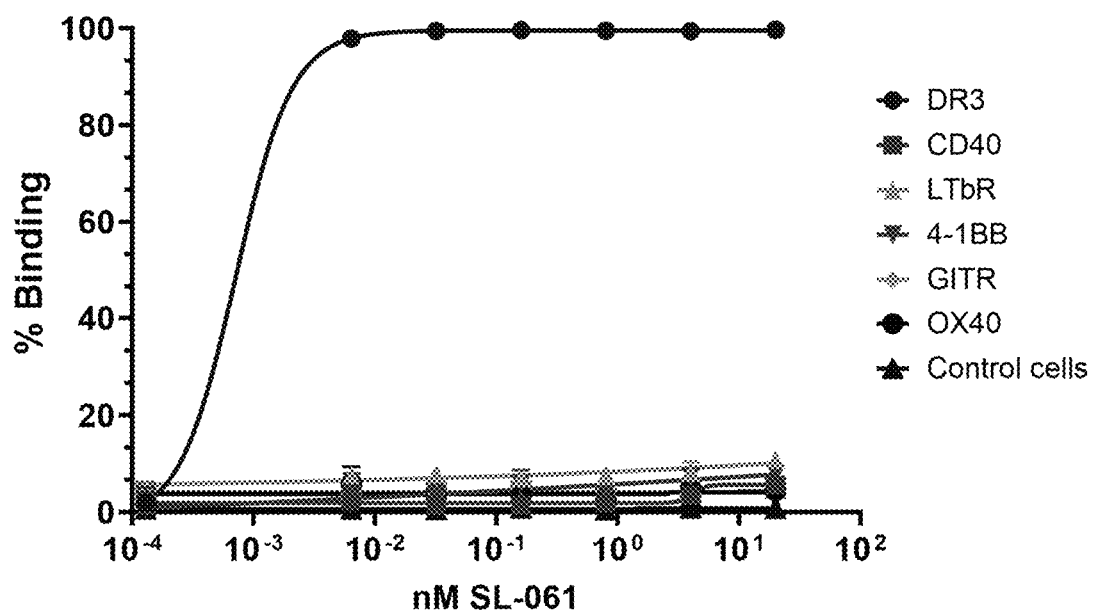
FIG. 7B. SL-061 is specific for binding native TNFRSF25. Several TNFRSF receptors overexpressed in engineered mammalian cells were incubated with various concentrations of SL-061. Cells were washed and further incubated with APC-conjugated anti-human Fc antibody to detect antibody-drug bound cells by flow cytometry.

To demonstrate that SL-061 is specific for binding native TNFRSF25, several TNFRSF receptors overexpressed in engineered mammalian cells were incubated with various concentrations of SL-061. Cells were washed and further incubated with APC-conjugated anti-human Fc antibody to detect antibody-drug bound cells by flow cytometry. SL-061 showed no detectable binding to the other TNFRSF receptors tested and was specific to TNFRSF25 only (FIG. 7B).

Figure 7C:
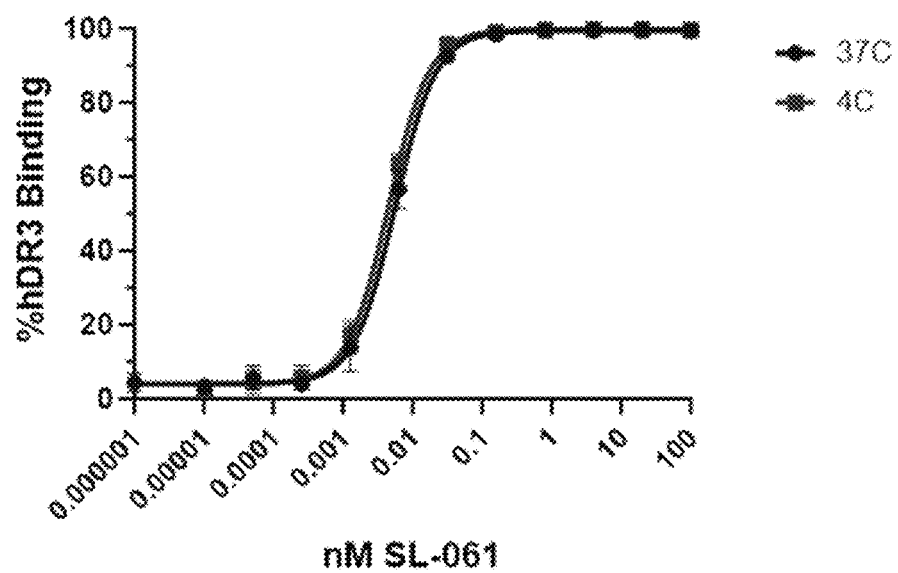
FIG. 7C. SL-061 does not induce internalization of TNFRSF25 receptor in engineered mammalian cells. Engineered CHOK1 cells overexpressing TNFRSF25 (cDNA sequence NP_683866) were incubated with various concentrations of SL-061 for 30 min at 4° C. or 37° C. Cells were washed and further incubated with APC-conjugated anti-human Fc antibody to detect antibody-drug bound cells by flow cytometry.

To demonstrate that SL-061 does not induce internalization of TNFRSF25, engineered CHOK1 cells overexpressing TNFRSF25 (cDNA sequence NP_683866) were incubated with various concentrations of SL-061 for 30 min at 4° C. or 37° C. Cells were washed and further incubated with APC-conjugated anti-human Fc antibody to detect antibody-drug bound cells by flow cytometry. TNFRSF25 binding by SL-061 is unaltered at 4° C. or 37° C. (FIG. 7C), suggesting no internalization of the TNFRSF25 receptor at 37° C.

Figure 7D:
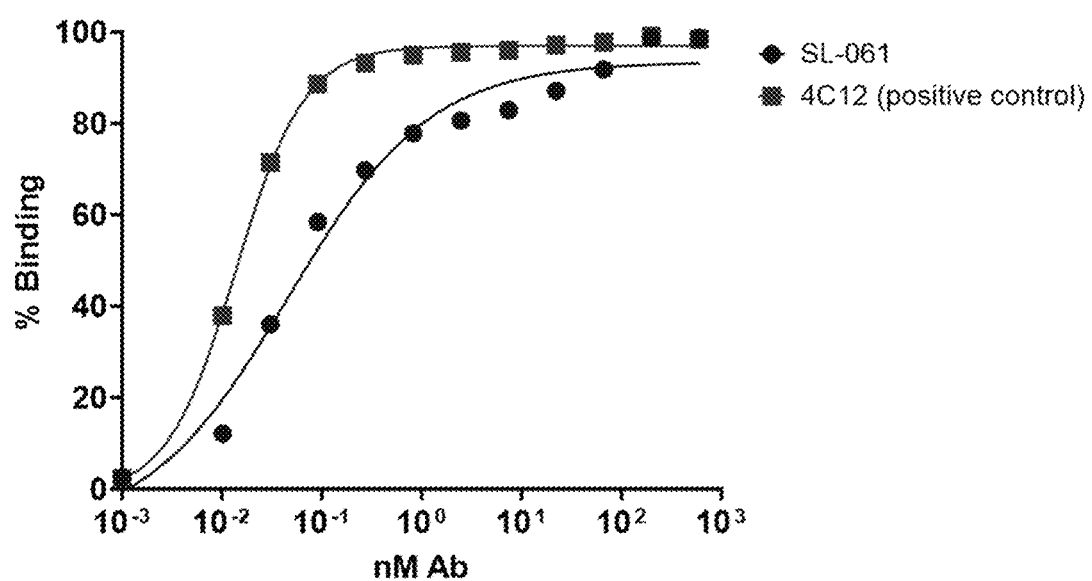
FIG. 7D. SL-061 exhibits binding to native Cynomolgus TNFRSF25. The Cynomolgus TNFRSF25 sequence (REFSEQ accession no: XM_015443331.1) was cloned into the pCDNA vector for cell-surface expression as a bicistronic gene to co-express cleavable, cytoplasmic GFP. The vector was transiently transfected in HEK293 cells. 24-hr post-transfection, cells were incubated at various concentrations of SL-061 or 4C12 (positive control). Next, cells were washed and further incubated with APC-conjugated anti-human Fc antibody to detect antibody-drug bound cells by flow cytometry.

To demonstrate that SL-061 binds to native Cynomolgus TNFRSF25, the Cynomolgus TNFRSF25 sequence (REFSEQ accession no: XM_015443331.1) was cloned into the pCDNA vector for cell-surface expression as a bicistronic gene to co-express cleavable, cytoplasmic GFP. The vector was transiently transfected in HEK293 cells. 24-hr post-transfection, cells were incubated at various concentrations of SL-061 or 4C12 (positive control). Next, cells were washed and further incubated with APC-conjugated anti-human Fc antibody to detect antibody-drug bound cells by flow cytometry (FIG. 7D).

Figure 8A:
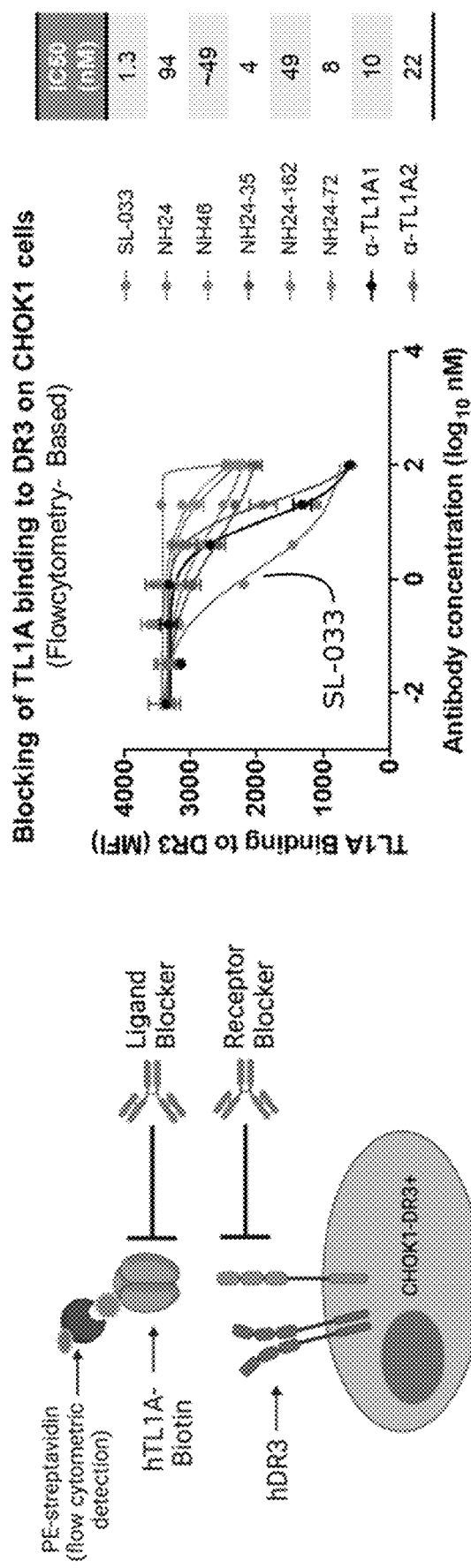
FIG. 8A. Anti-TNFRSF25 antibodies competitively block TL1A binding to native TNFRSF25 on CHOK1 cells. To assess the ability of the TNFRSF25 antagonist antibodies to bind TNFRSF25 and block TL1A binding, CHOK1-TNFRSF25$^+$ cells were first incubated with various concentrations of anti-TNFRSF25 antibodies at 4° C. for 30 minutes. Anti-TL1A benchmark antibodies (α-TL1A1 and α-TL1A2) were used as comparator controls in this assay. A fixed concentration of biotinylated human TL1A-Fc protein (156 nM) was subsequently added to cells and further incubated at 4° C. for 1 hour. After washing to remove excess antibodies and TL1A, cells were further incubated with PE-conjugated streptavidin for detection of cells bound to TL1A by flow cytometry. The mean fluorescence intensity of TL1A (PE) is shown.
Figure 8A:
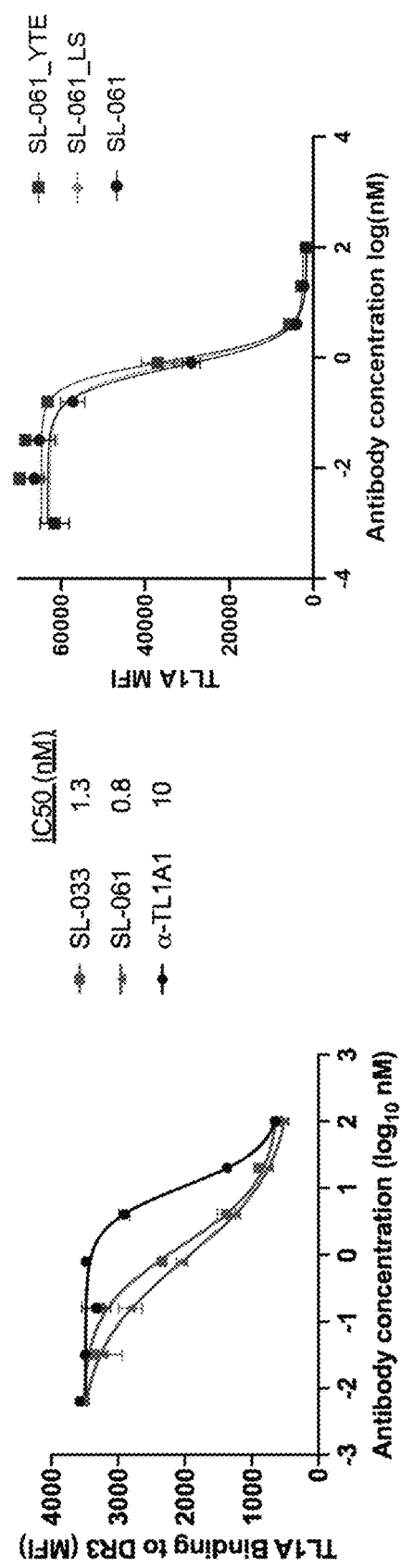

To assess the ability of the TNFRSF25 antagonist antibodies to bind TNFRSF25 and block TL1A binding, CHOK1-TNFRSF25+ cells were first incubated with various concentrations of anti-TNFRSF25 antibodies at 4° C. for 30 minutes. A fixed concentration of biotinylated human TL1A-Fc protein (156 nM) was subsequently added to the cells and further incubated at 4° C. for 1 hour. After washing to remove excess antibodies and TL1A, cells were further incubated with PE-conjugated streptavidin to provide for detection of cells bound to TL1A by flow cytometry. The mean fluorescence intensity of TL1A (PE) is shown (FIG. 8A). SL-033 and SL-061 competitively blocked TL1A binding to native TNFRSF25 on CHOK1 cells and outperformed anti-TL1A antibodies in blocking TL1A binding to TNFRSF25 on cells. SL-061 was found to have an approximately 13-fold lower $IC_{50}$ than the benchmark anti-TL1A antibody in blocking TL1A binding to TNFRSF25 on cells.

In addition, SL-061_YTE and SL-061_LS variants block TL1A binding to native TNFRSF25 with similar potency as SL-061.

Figure 8B:
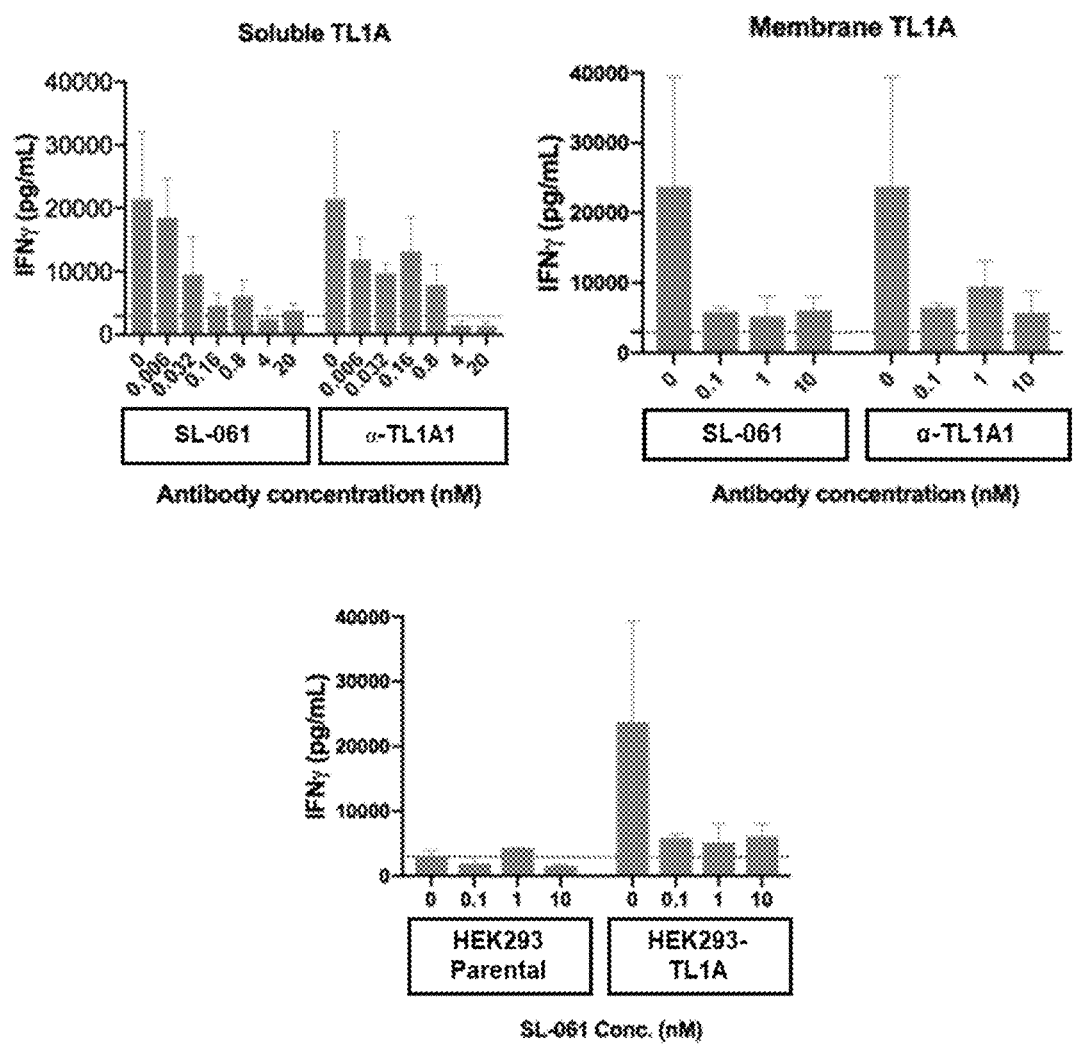
FIG. 8B. Anti-TNFRSF25 antibody SL-061 efficiently blocked soluble, and membrane bound forms of TL1A-induced IFNγ secretion from human PBMCs. Human PBMCs were stimulated with anti-CD3/CD28 and were treated with either soluble TL1A (100 ng/mL) or co-cultured with 1×10$^4$ each of either HEK293-TL1A or HEK293 parental cells that do not express TL1A on the surface. Supernatant was harvested after 72 hours for analysis of IFNγ level by MSD. Dotted line represents IFNγ level produced by PBMCs in the absence of TL1A. An anti-TL1A benchmark antibody (α-TL1A1) was used as a comparator control in this assay. The bottom graph shows that IFNγ secretion was indeed induced by the membrane-expressed TL1A since the HEK293 parental cells did not induce IFNγ secretion even in the absence of SL-061 antibody.

Anti-TNFRSF25 antibody SL-061 was tested for the ability to efficiently block soluble, and membrane bound forms of TL1A-induced IFNγ secretion from human PBMCs following anti-CD3/CD28 stimulation, in comparison to a benchmark anti-TL1A antibody. Human PBMCs were stimulated with anti-CD3/CD28 and were treated with either soluble TL1A (100 ng/mL) or co-cultured either HEK293-TL1A cells or HEK293 parental cells that do not express TL1A on the surface. Supernatant was harvested after 72 hours for analysis of IFNγ level by MSD (FIG. 8B). The bottom graph in FIG. 8B shows that IFNγ secretion was indeed induced by the membrane-expressed TL1A since the HEK293 parental cells did not induce IFNγ secretion even in the absence of SL-061 antibody.

Human PBMCs were stimulated with either IL12+IL18 or anti-CD3/CD28 for 24 hours to assess binding of anti-TNFRSF25 to lymphocyte subsets. Cells were harvested and incubated with SL-033 or SL-061 (5 µg/mL), followed by incubation with APC-anti-human Fc (for detection of SL-033 or SL-061) and lineage specific antibodies for T and NK cells for analysis by flow cytometry. Histogram SL-033 intensity (FIG. 9) and mean fluorescent intensity (MFI) of SL-061 binding (FIG. 10) is shown for each cell type.

Figure 9:
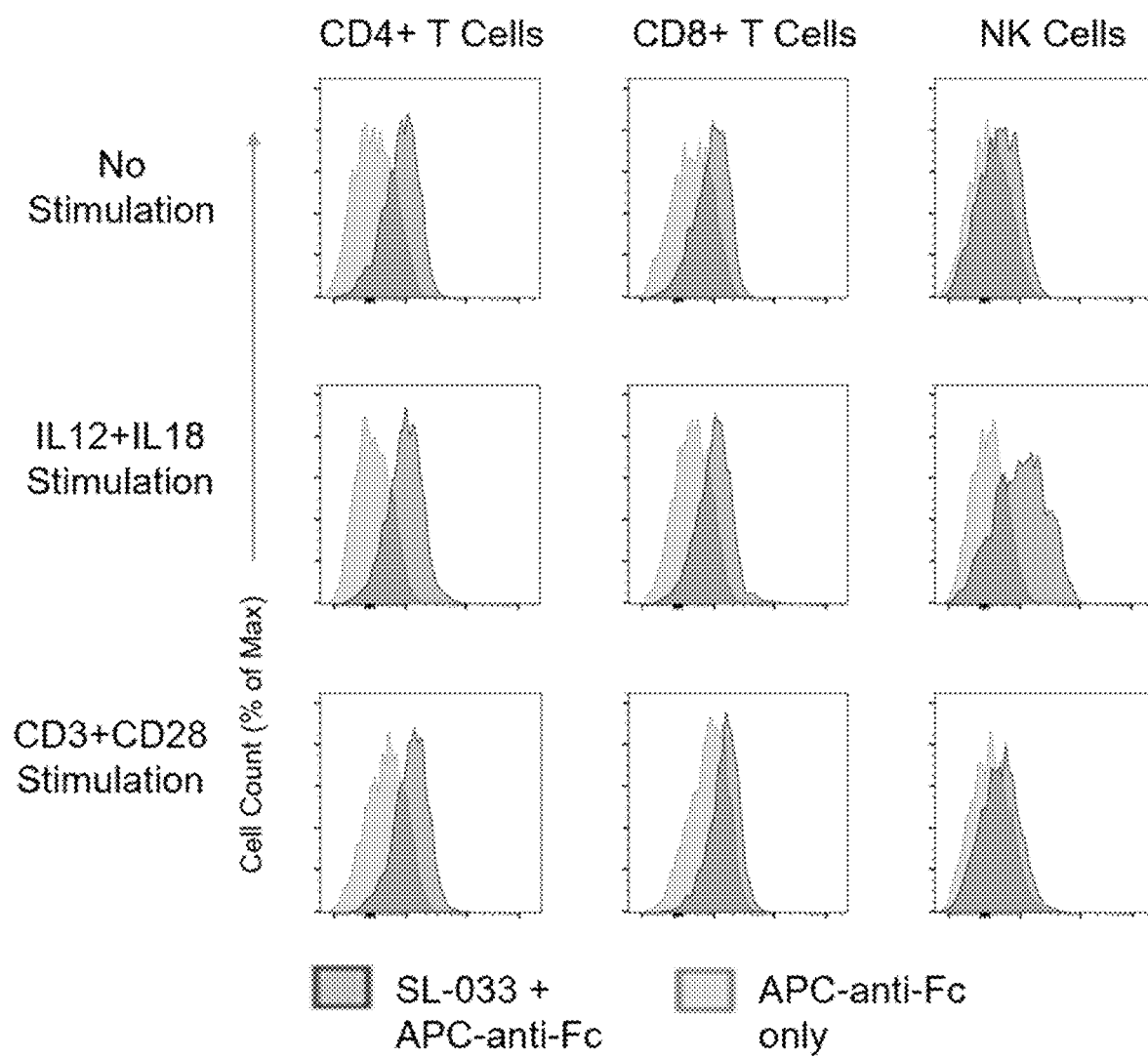
FIG. 9. Binding of SL-033 to TNFRSF25 on lymphocytes in human PBMCs. Human PBMCs were left unstimulated or stimulated with either IL12+IL18 or anti-CD3/CD28 (used at a sub-optimal dose) for 24 hours to assess binding of anti-TNFRSF25 (SL-033) on lymphocyte subsets. Cells were harvested and incubated with a fixed concentration of SL-033 (5 μg/mL), followed by incubation with APC-anti-human Fc (detection of SL-033) and lineage specific antibodies for T and NK cells for analysis by flow cytometry. Histogram SL-033 intensity is shown for each cell type.
Figure 10:
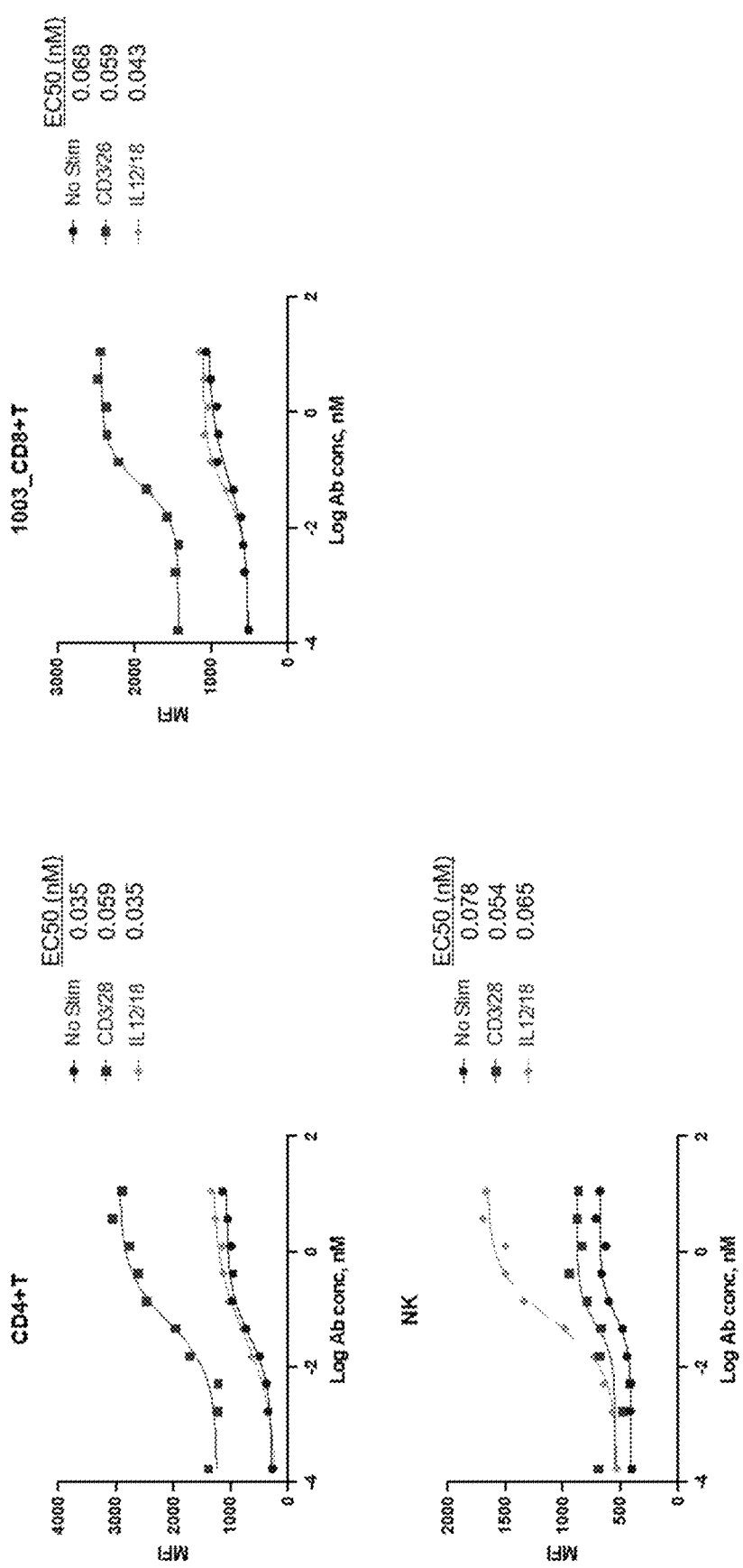
FIG. 10. Dose-dependent binding of SL-061 to TNFRSF25 on lymphocytes in human PBMCs. Human PBMCs were stimulated with either IL12+IL18 or anti-CD3/CD28 for 24 hours to assess binding of anti-TNFRSF25 (SL-061) on lymphocyte subsets. Cells were harvested and incubated with SL-061 at various concentrations, followed by incubation with APC-anti-human Fc (detection of SL-061) and lineage specific antibodies for T and NK cells for analysis by flow cytometry. Mean fluorescent intensity (MFI) of SL-061 binding is shown for each cell type.

SL-033 similarly bound to CD4+ and CD8+ T cells in stimulated and unstimulated conditions, consistent with constitutive expression of TNFRSF25 on T cells. NK cells minimally express TNFRSF25 in the resting state, but binding of SL-033 increased in NK cells upon IL12 and IL18 stimulation (FIG. 9).

Figure 11:
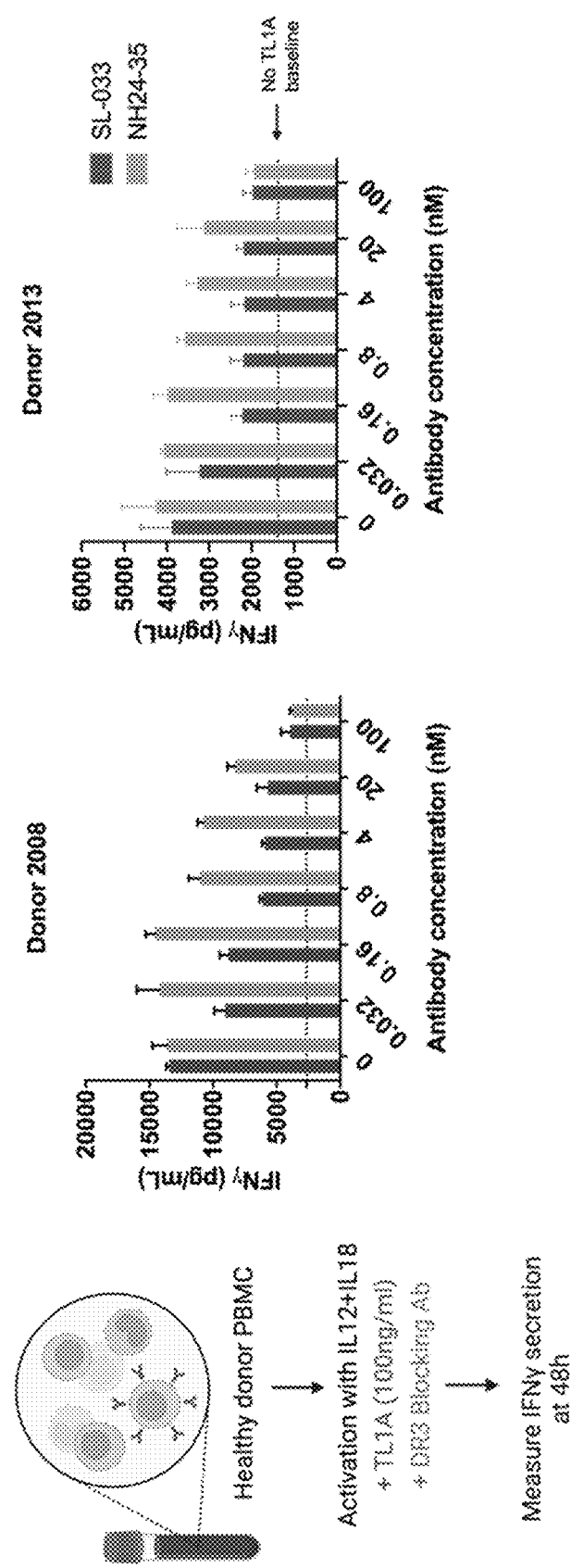
FIG. 11. Anti-TNFRSF25 antibodies efficiently block TL1A-induced IFNγ secretion from human PBMCs (IL12+

Anti-TNFRSF25 antibodies were tested for the ability to efficiently block TL1A-induced IFNγ secretion from human PBMCs following IL-12+IL-18 stimulation. Human PBMCs were stimulated with IL-12 and IL-18 for 24 hours to upregulate TNFRSF25 expression. After 24 hours, cells were treated with various concentrations of anti-TNFRSF25 antibodies with or without TL1A (100 ng/mL). Supernatant was harvested after 48 hours for analysis of IFNγ levels by MSD. SL-033 blocked TL1A-induced IFNγ secretion more efficiently than NH24-35 (FIG. 11). Moreover enhanced blockade of IFNγ secretion was seen for SL-033 with Fc-silencing mutations (FIG. 12).

Anti-TNFRSF25 antibodies were tested for the ability to efficiently block TL1A-induced IFNγ secretion from human PBMCs following stimulation with CD3/CD28 complexes with or without TL1A (100 ng/mL) for 72 hours. Supernatant was harvested after 72 hours for analysis of IFNγ levels by MSD. SL-033 (L234A/L235A) and SL-061 (L234A/L235A+G237A) comparably blocked IFNγ secretion (FIG. 13). In the same assay, supernatant was harvested after 72 hours for analysis of additional cytokines by MSD. SL-033 (L234A/L235A) blocked TL1A-induced secretion of TNFα, IL-6, and GM-CSF with no evidence of residual agonism (FIG. 14).

Human PBMCs from three healthy donors were stimulated with anti-CD3/CD28 complexes with or without TL1A (100 ng/mL) and treated with various concentrations of anti-TNFRSF25 antibodies. Supernatant was harvested after 72 hours for analysis of IFNγ levels by MSD. SL-061 (L234A/L235A+G237A) blocked TL1A-induced IFNγ secretion from lymphocytes stimulated with CD3/CD28 (FIG. 15).

Human PBMCs derived from donors with ulcerative colitis (UC) or Crohn's Disease (CD) were stimulated with CD3/CD28 complexes with or without TL1A (100 ng/mL)

and treated with various concentrations of anti-TNFRSF25 antibodies. Supernatant was harvested after 72 hours for analysis of cytokine levels by MSD. SL-061 (L234A/L235A+G237A) blocked TL1A-induced IFNγ secretion from IBD patient derived PBMCs (FIG. 16).

Anti-TNFRSF25 antibodies were tested for toxicity on the intestinal epithelial barrier in an ex vivo inflammation model. The RepliGut® intestinal culture system was employed to assess the toxicity of an anti-DR3 antibody under inflammatory conditions. Human intestinal stem cells were seeded in a transwell system featuring a semi-permeable membrane coated with a biomimetic scaffold composed of a collagen hydrogel, which promotes the differentiation of stem cells into a monolayer of intestinal epithelial cells, closely mimicking the in vivo intestinal epithelium. The cells were cultured according to the RepliGut® protocol, allowing for the formation of a fully differentiated, polarized epithelial monolayer. The resulting epithelial monolayer possessed a population of polarized and differentiated cells, representing a physiologically relevant model system for toxicity evaluation. Once the monolayer was established (6-7 days), the cultured cells were exposed to SL-061 at a fixed concentration of 5 µg/mL in the presence of varying concentrations of pro-inflammatory cytokines, TNFα and IFNγ. These cytokines were added to mimic an inflammatory environment, with their concentrations varied to assess dose-dependent effects. Barrier function was evaluated by measuring transepithelial electrical resistance (TEER) daily throughout the experiment. TEER measurements provide a quantitative assessment of the integrity of the tight junctions between epithelial cells, serving as an indicator of the overall barrier function of the intestinal monolayer. The combination of TNFα and IFNγ induced epithelial barrier disruption, as indicated by the decrease in TEER 48 hours after treatment (FIG. 17A). Moreover, addition of SL-061 did not exacerbate the epithelial barrier disruption induced by TNFα and IFNγ (FIG. 17A).

The effects of SL-061 on intestinal barrier function were also evaluated using a co-culture system of pre-activated peripheral blood mononuclear cells (PBMCs) and the RepliGut® intestinal epithelial model. PBMCs derived from a healthy donor were pre-activated with anti-CD3/CD28 complexes and recombinant TL1A to stimulate the production of inflammatory cytokines. After 24 hours, pre-activated PBMCs were added to the basal compartment of the RepliGut® intestinal culture system while SL-061 (5 µg/mL) was applied to both the apical and basal compartments. Intestinal barrier integrity was assessed by daily TEER measurements. TEER values were normalized to the maximum value in each well to account for well-to-well variability. Addition of TL1A to pre-activated PBMCs resulted in significant decrease in TEER five days post-treatment, indicating loss of epithelial barrier function (FIG. 17B, left panel). In contrast, addition of SL-61 did not result in a decrease in TEER at the same time point, confirming a protective effect of anti-TNFRSF25 against TL1A-mediated intestinal damage (FIG. 17B, left panel). The presence of inflammatory cytokines was evaluated by MSD in culture supernatant six days post-treatment. Addition of TL1A resulted in increased concentration of TNFα, which was attenuated by SL-061 treatment in the co-culture system (FIG. 17B, right panel).

Receptor occupancy (RO) and immunophenotypic analysis of SL-061 was evaluated in a non-human primate (NHP) toxicology study over a 4-week period to evaluate the safety and pharmacokinetic profile of the mAb. Cynomolgus macaques received three doses of intravenous administration of SL-061 at 1, 10, or 100 mg/kg every two weeks (i.e., at Days 1, 15, and 29). Flow cytometric analysis was performed on whole blood samples collected at various time points pre- and post-treatment. Plasma was collected at different time points to assess the pharmacokinetic parameters.

For analysis, red blood cells were lysed, and samples were stained with fluorescently labeled antibodies targeting cell surface markers (CD3, CD4, CD8, CD25, CD127, TNRFSF25 [clone 4C12]) and intracellular markers (FoxP3, Ki-67). T-cell subsets were identified using the following marker combinations:

CD4+ T cells: $CD3^+CD4^+CD8^-$ lymphocytes
CD8+ T cells: $CD3^+CD4^-CD8^+$ lymphocytes
Regulatory T cells (Tregs): $CD3^+CD4^+$ $CD8^-CD25^+$ $FoxP3^+$ lymphocytes
Proliferating CD4+ T cells: $CD3^+CD4^+$ $CD8^-Ki67^+$ lymphocytes RO was assessed by measuring SL-061-mediated inhibition of anti-TNFRSF25 (clone 4C12) binding to Tregs and proliferating $CD4^+$ T cells, which express the highest levels of TNFRSF25. The percentage of $TNFRSF25^+$ cells was determined relative to isotype antibody control staining. Complete RO was observed across all dose levels and maintained for at least two weeks post-dose (FIG. 18A) and even four week after the final dose (FIG. 19A). The absence of dose-dependent inhibition of anti-TNFRSF25 (clone 4C12) binding suggests full RO is achieved at or below 1 mg/kg (FIGS. 18A and 19A). These data suggest persistent target engagement even four weeks after the final dose (FIG. 19B).

No changes were observed in the proportion of Tregs and proliferating $CD4^+$ T cells (FIGS. 18B, 20A, and 20B), proliferating $CD8^+$ T cells (FIG. 20C), or absolute counts of T cell subsets (FIG. 18C), indicating a lack of agonist activity following SL-061 engagement on T cells. Moreover, compared to vehicle control, the frequency of $CD25^+$ cells among $CD4^+$ T cells and $CD8^+$ T cells was not significantly altered by SL-061 treatment (FIG. 21A). Similarly, the percentage of $Ki67^+$ cells remained largely unchanged following SL-061 administration across all dose groups (FIG. 21B). Notably, despite high receptor occupancy of SL-061 on Tregs, there were no observable changes in either the proportion of Tregs within the $CD4^+$ T cell population or the percentage of proliferating $Ki67^+$ Tregs (FIG. 21C). Overall, despite demonstrated target engagement as evidenced by receptor occupancy data, SL-061 treatment did not lead to substantial changes in T-cell counts, activation status, or proliferation at any of the dose levels tested.

Toxicokinetic analysis of SL-061 showed that the antibody was eliminated over time with no observable clinical or toxicologic effect on the test subjects. In-life and recovery study data collected showed no abnormality in white blood cells, red blood cells, platelets, or neutrophil counts after injecting SL-061. Toxicological evaluation showed no discernable toxic effects from treating the non-human primates at even the highest dose level of 100 mg/kg.

Example 2

All Fc silent antibodies tested herein have been successfully produced at small scale (<5 mg) via transient production runs in CHOK1-derived cells followed by Protein A capture chromatography. However, in larger scale production, the SL-034 L234A/L235A+N297A) antibody precipitated following affinity chromatography capture whereas the SL-061 (L234A/L235A+G237A) antibody did not.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A monoclonal antibody or antibody fragment that binds to tumor necrosis factor receptor super-family 25 (TNFRSF25), wherein the antibody or antibody fragment comprises clone-paired heavy chain and light chain sequences of: (a) SEQ ID NO: 134 and SEQ ID NO: 57; (b) SEQ ID NO: 56 and SEQ ID NO: 57; (c) SEQ ID NO: 58 and SEQ ID NO: 57; (d) SEQ ID NO: 150 and SEQ ID NO: 57; (e) SEQ ID NO: 153 and SEQ ID NO: 57; (f) SEQ ID NO: 151 and SEQ ID NO: 152; or (g) SEQ ID NO: 135 and ID NO: 57.

2. The monoclonal antibody or antibody fragment of claim 1, wherein the antibody or antibody fragment comprises clone-paired heavy chain and light chain sequences of: (a) SEQ ID NO: 134 and SEQ ID NO: 57.

3. The monoclonal antibody or antibody fragment of claim 1, wherein the antibody is a chimeric antibody, a biparatopic antibody, or a bispecific antibody.

4. The monoclonal antibody or antibody fragment of claim 1, wherein the antibody is an IgG antibody or a recombinant IgG antibody or antibody fragment.

5. The monoclonal antibody or antibody fragment of claim 1, wherein the antibody or antibody fragment blocks TL1A binding to cell-surface TNFRSF25.

6. The monoclonal antibody or antibody fragment of claim 1, wherein the antibody or antibody fragment blocks TL1A-induced secretion of TNFalpha, IL-6, GM-CSF, and IFNgamma.

7. The monoclonal antibody or antibody fragment of claim 1, wherein the antibody or antibody fragment does not agonize cell-surface TNFRSF25.

8. The monoclonal antibody or antibody fragment of claim 1, wherein the antibody or antibody fragment does not induce internalization of cell-surface TNFRSF25.

9. An isolated nucleic acid encoding the antibody heavy and/or light chain region of the antibody or antibody fragment of claim 1.

10. An expression vector comprising the nucleic acid of claim 9.

11. A hybridoma or engineered cell comprising a nucleic acid encoding the antibody or antibody fragment of claim 1.

12. A hybridoma or engineered cell comprising the nucleic acid of claim 9.

13. A method of making the monoclonal antibody or antibody fragment of claim 1, the method comprising culturing a hybridoma or engineered cell comprising a nucleic acid encoding the antibody or antibody fragment under conditions that allow expression of the antibody or antibody fragment and optionally isolating the antibody or antibody fragment from the culture.

14. A pharmaceutical formulation comprising one or more antibody or antibody fragment of claim 1.

15. A method of treating a patient having a disease or disorder associated with inflammation and/or autoimmunity, the method comprising administering to the patient the pharmaceutical formulation of claim 14.

16. The method of claim 15, wherein the disease or disorder is ulcerative colitis, Crohn's disease, rheumatoid arthritis, psoriasis, atherosclerosis, asthma, multiple sclerosis, primary biliary cirrhosis, systemic lupus erythematosus, or ankylosing spondylitis.

17. The method of claim 15, wherein the administering preserves epithelial barrier integrity.

\* \* \* \* \*

```
                            SEQUENCE LISTING

Sequence total quantity: 153
SEQ ID NO: 1              moltype = AA  length = 7
FEATURE                   Location/Qualifiers
source                    1..7
                          mol_type = protein
                          organism = Synthetic construct
SEQUENCE: 1
GYSAAWN                                                                    7

SEQ ID NO: 2              moltype = AA  length = 18
FEATURE                   Location/Qualifiers
source                    1..18
                          mol_type = protein
                          organism = Synthetic construct
SEQUENCE: 2
RTYYRSKWYN DYAVSVKS                                                       18

SEQ ID NO: 3              moltype = AA  length = 20
FEATURE                   Location/Qualifiers
source                    1..20
                          mol_type = protein
                          organism = Synthetic construct
SEQUENCE: 3
DYYGSESYYN RGYYYYGMDV                                                     20

SEQ ID NO: 4              moltype = AA  length = 11
FEATURE                   Location/Qualifiers
source                    1..11
                          mol_type = protein
                          organism = Synthetic construct
SEQUENCE: 4
RASPGISSAL A                                                              11

SEQ ID NO: 5              moltype = AA  length = 7
FEATURE                   Location/Qualifiers
source                    1..7
                          mol_type = protein
                          organism = Synthetic construct
SEQUENCE: 5
DESSQES                                                                    7

SEQ ID NO: 6              moltype = AA  length = 9
FEATURE                   Location/Qualifiers
source                    1..9
                          mol_type = protein
                          organism = Synthetic construct
SEQUENCE: 6
QQFNDYPLT                                                                  9

SEQ ID NO: 7              moltype = AA  length = 5
FEATURE                   Location/Qualifiers
source                    1..5
                          mol_type = protein
                          organism = Synthetic construct
SEQUENCE: 7
SYGMS                                                                      5

SEQ ID NO: 8              moltype = AA  length = 17
FEATURE                   Location/Qualifiers
source                    1..17
                          mol_type = protein
                          organism = Synthetic construct
SEQUENCE: 8
YISSSGGHTY YADSVKG                                                        17

SEQ ID NO: 9              moltype = AA  length = 7
FEATURE                   Location/Qualifiers
```

```
source                  1..7
                        mol_type = protein
                        organism = Synthetic construct
SEQUENCE: 9
GSGSFDY                                                              7

SEQ ID NO: 10           moltype = AA  length = 11
FEATURE                 Location/Qualifiers
source                  1..11
                        mol_type = protein
                        organism = Synthetic construct
SEQUENCE: 10
QASQDITNYL S                                                         11

SEQ ID NO: 11           moltype = AA  length = 7
FEATURE                 Location/Qualifiers
source                  1..7
                        mol_type = protein
                        organism = Synthetic construct
SEQUENCE: 11
DASNLET                                                              7

SEQ ID NO: 12           moltype = AA  length = 9
FEATURE                 Location/Qualifiers
source                  1..9
                        mol_type = protein
                        organism = Synthetic construct
SEQUENCE: 12
QQYDTLPIT                                                            9

SEQ ID NO: 13           moltype = AA  length = 5
FEATURE                 Location/Qualifiers
source                  1..5
                        mol_type = protein
                        organism = Synthetic construct
SEQUENCE: 13
ELSMH                                                                5

SEQ ID NO: 14           moltype = AA  length = 17
FEATURE                 Location/Qualifiers
source                  1..17
                        mol_type = protein
                        organism = Synthetic construct
SEQUENCE: 14
GYDPEDGESI FAQKFQG                                                   17

SEQ ID NO: 15           moltype = AA  length = 10
FEATURE                 Location/Qualifiers
source                  1..10
                        mol_type = protein
                        organism = Synthetic construct
SEQUENCE: 15
DLNWEDAFDV                                                           10

SEQ ID NO: 16           moltype = AA  length = 13
FEATURE                 Location/Qualifiers
source                  1..13
                        mol_type = protein
                        organism = Synthetic construct
SEQUENCE: 16
SGSGSNIGNY YVA                                                       13

SEQ ID NO: 17           moltype = AA  length = 7
FEATURE                 Location/Qualifiers
source                  1..7
                        mol_type = protein
                        organism = Synthetic construct
SEQUENCE: 17
DNNKRPS                                                              7

SEQ ID NO: 18           moltype = AA  length = 14
FEATURE                 Location/Qualifiers
source                  1..14
                        mol_type = protein
                        organism = Synthetic construct
SEQUENCE: 18
GTWDTSLTAG DIYV                                                      14

SEQ ID NO: 19           moltype = AA  length = 5
```

-continued

```
FEATURE                 Location/Qualifiers
source                  1..5
                        mol_type = protein
                        organism = Synthetic construct
SEQUENCE: 19
NHDMN                                                                   5

SEQ ID NO: 20           moltype = AA  length = 17
FEATURE                 Location/Qualifiers
source                  1..17
                        mol_type = protein
                        organism = Synthetic construct
SEQUENCE: 20
YISSASGLIS YADSVRG                                                     17

SEQ ID NO: 21           moltype = AA  length = 12
FEATURE                 Location/Qualifiers
source                  1..12
                        mol_type = protein
                        organism = Synthetic construct
SEQUENCE: 21
DPAYSGNYAL DF                                                          12

SEQ ID NO: 22           moltype = AA  length = 12
FEATURE                 Location/Qualifiers
source                  1..12
                        mol_type = protein
                        organism = Synthetic construct
SEQUENCE: 22
TLSSELSSYT IV                                                          12

SEQ ID NO: 23           moltype = AA  length = 11
FEATURE                 Location/Qualifiers
source                  1..11
                        mol_type = protein
                        organism = Synthetic construct
SEQUENCE: 23
LKSDGSHGKG D                                                           11

SEQ ID NO: 24           moltype = AA  length = 13
FEATURE                 Location/Qualifiers
source                  1..13
                        mol_type = protein
                        organism = Synthetic construct
SEQUENCE: 24
GAGYTLAGQY GWV                                                         13

SEQ ID NO: 25           moltype = AA  length = 10
FEATURE                 Location/Qualifiers
source                  1..10
                        mol_type = protein
                        organism = Synthetic construct
SEQUENCE: 25
GDSVSGYSAA                                                             10

SEQ ID NO: 26           moltype = AA  length = 9
FEATURE                 Location/Qualifiers
source                  1..9
                        mol_type = protein
                        organism = Synthetic construct
SEQUENCE: 26
TYYRSKWYN                                                               9

SEQ ID NO: 27           moltype = AA  length = 22
FEATURE                 Location/Qualifiers
source                  1..22
                        mol_type = protein
                        organism = Synthetic construct
SEQUENCE: 27
ARDYYGSESY YNRGYYYYGM DV                                               22

SEQ ID NO: 28           moltype = AA  length = 6
FEATURE                 Location/Qualifiers
source                  1..6
                        mol_type = protein
                        organism = Synthetic construct
SEQUENCE: 28
PGISSA                                                                  6
```

```
SEQ ID NO: 29          moltype =    length =
SEQUENCE: 29
000

SEQ ID NO: 30          moltype = AA   length = 8
FEATURE                Location/Qualifiers
source                 1..8
                       mol_type = protein
                       organism = Synthetic construct
SEQUENCE: 30
GFTFSSYG                                                                   8

SEQ ID NO: 31          moltype = AA   length = 8
FEATURE                Location/Qualifiers
source                 1..8
                       mol_type = protein
                       organism = Synthetic construct
SEQUENCE: 31
ISSSGGHT                                                                   8

SEQ ID NO: 32          moltype = AA   length = 9
FEATURE                Location/Qualifiers
source                 1..9
                       mol_type = protein
                       organism = Synthetic construct
SEQUENCE: 32
ARGSGSFDY                                                                  9

SEQ ID NO: 33          moltype = AA   length = 6
FEATURE                Location/Qualifiers
source                 1..6
                       mol_type = protein
                       organism = Synthetic construct
SEQUENCE: 33
QDITNY                                                                     6

SEQ ID NO: 34          moltype =    length =
SEQUENCE: 34
000

SEQ ID NO: 35          moltype = AA   length = 9
FEATURE                Location/Qualifiers
source                 1..9
                       mol_type = protein
                       organism = Synthetic construct
SEQUENCE: 35
QQYDTLPIT                                                                  9

SEQ ID NO: 36          moltype = AA   length = 8
FEATURE                Location/Qualifiers
source                 1..8
                       mol_type = protein
                       organism = Synthetic construct
SEQUENCE: 36
GSTVKELS                                                                   8

SEQ ID NO: 37          moltype = AA   length = 8
FEATURE                Location/Qualifiers
source                 1..8
                       mol_type = protein
                       organism = Synthetic construct
SEQUENCE: 37
YDPEDGES                                                                   8

SEQ ID NO: 38          moltype = AA   length = 12
FEATURE                Location/Qualifiers
source                 1..12
                       mol_type = protein
                       organism = Synthetic construct
SEQUENCE: 38
ATDLNWEDAF DV                                                             12

SEQ ID NO: 39          moltype = AA   length = 8
FEATURE                Location/Qualifiers
source                 1..8
                       mol_type = protein
                       organism = Synthetic construct
SEQUENCE: 39
GSNIGNYY                                                                   8
```

```
SEQ ID NO: 40          moltype =    length =
SEQUENCE: 40
000

SEQ ID NO: 41          moltype = AA   length = 14
FEATURE                Location/Qualifiers
source                 1..14
                       mol_type = protein
                       organism = Synthetic construct
SEQUENCE: 41
GTWDTSLTAG DIYV                                                           14

SEQ ID NO: 42          moltype = AA   length = 8
FEATURE                Location/Qualifiers
source                 1..8
                       mol_type = protein
                       organism = Synthetic construct
SEQUENCE: 42
GFTFSNHD                                                                  8

SEQ ID NO: 43          moltype = AA   length = 8
FEATURE                Location/Qualifiers
source                 1..8
                       mol_type = protein
                       organism = Synthetic construct
SEQUENCE: 43
ISSASGLI                                                                  8

SEQ ID NO: 44          moltype = AA   length = 14
FEATURE                Location/Qualifiers
source                 1..14
                       mol_type = protein
                       organism = Synthetic construct
SEQUENCE: 44
ARDPAYSGNY ALDF                                                           14

SEQ ID NO: 45          moltype = AA   length = 7
FEATURE                Location/Qualifiers
source                 1..7
                       mol_type = protein
                       organism = Synthetic construct
SEQUENCE: 45
SELSSYT                                                                   7

SEQ ID NO: 46          moltype = AA   length = 7
FEATURE                Location/Qualifiers
source                 1..7
                       mol_type = protein
                       organism = Synthetic construct
SEQUENCE: 46
LKSDGSH                                                                   7

SEQ ID NO: 47          moltype = AA   length = 13
FEATURE                Location/Qualifiers
source                 1..13
                       mol_type = protein
                       organism = Synthetic construct
SEQUENCE: 47
GAGYTLAGQY GWV                                                            13

SEQ ID NO: 48          moltype = AA   length = 132
FEATURE                Location/Qualifiers
source                 1..132
                       mol_type = protein
                       organism = Synthetic construct
SEQUENCE: 48
QVQLQQSGPG LVKPSQTLSL TCAISGDSVS GYSAAWNWIR QSPSRGLEWL GRTYYRSKWY          60
NDYAVSVKSR ITINPDTSKN QFSLQLNSVT PEDTAVYYCA RDYYGSESYY NRGYYYYGMD         120
VWGQGTTVTV SS                                                            132

SEQ ID NO: 49          moltype = AA   length = 107
FEATURE                Location/Qualifiers
source                 1..107
                       mol_type = protein
                       organism = Synthetic construct
SEQUENCE: 49
AIQLTQSPSS LSASVGDRVT ITCRASPGIS SALAWYQQKP GKAPKLLMYD ESSQESGVPS          60
RFSGSGSGTD FTLTISSLQP EDFATYYCQQ FNDYPLTFGG GTKVEIK                       107
```

```
SEQ ID NO: 50          moltype = AA  length = 116
FEATURE                Location/Qualifiers
source                 1..116
                       mol_type = protein
                       organism = Synthetic construct
SEQUENCE: 50
EVQLVESGGG SVQPGGSLRL SCAASGFTFS SYGMSWIRQA PGKGLEWISY ISSSGGHTYY    60
ADSVKGRFTI SRDNAKNSLY LQMNSLRAED TAVYYCARGS GSFDYWGQGT LVTVSS       116

SEQ ID NO: 51          moltype = AA  length = 107
FEATURE                Location/Qualifiers
source                 1..107
                       mol_type = protein
                       organism = Synthetic construct
SEQUENCE: 51
DIVMTQSPSS LSASVGDRVT ITCQASQDIT NYLSWYQQKP GKAPKLLISD ASNLETGIPS    60
RFSGSGSGTD FTFTISSLQP EDIATYYCQQ YDTLPITFGQ GTRLEIK                 107

SEQ ID NO: 52          moltype = AA  length = 119
FEATURE                Location/Qualifiers
source                 1..119
                       mol_type = protein
                       organism = Synthetic construct
SEQUENCE: 52
QVQLVQSGSE VKKPGASVRV SCKVSGSTVK ELSMHWVRQA PGKGLEWMGG YDPEDGESIF    60
AQKFQGRVNM TEDRSTDTAY MELSSLRSED TAVYYCATDL NWEDAFDVWG QGTMVTVSS    119

SEQ ID NO: 53          moltype = AA  length = 113
FEATURE                Location/Qualifiers
source                 1..113
                       mol_type = protein
                       organism = Synthetic construct
SEQUENCE: 53
QSVLTQPPSV SAAPGQKVTI SCSGSGSNIG NYYVAWYQQF PGTAPKLLIY DNNKRPSGIP    60
DRFSGSKSGT SATLGITGLQ TGDEADYYCG TWDTSLTAGD IYVFGTGTKV TVL          113

SEQ ID NO: 54          moltype = AA  length = 121
FEATURE                Location/Qualifiers
source                 1..121
                       mol_type = protein
                       organism = Synthetic construct
SEQUENCE: 54
EVQLVESGGG LSQPGNSLQL SCEASGFTFS NHDMNWVRQA PGKGLEWVAY ISSASGLISY    60
ADSVRGRFTI SRDNAKNSLF LQMNNLKSED TAMYYCARDP AYSGNYALDF WGQGTQVTVS   120
S                                                                   121

SEQ ID NO: 55          moltype = AA  length = 115
FEATURE                Location/Qualifiers
source                 1..115
                       mol_type = protein
                       organism = Synthetic construct
SEQUENCE: 55
QPVLTQSPSA SASLSGSVKL TCTLSSELSS YTIVWYQQQP DKAPKYVMYL KSDGSHGKGD    60
GIPDRFSGSS SGAHRYLSVS NVQSEDDATY FCGAGYTLAG QYGWVFGSGT KVTVL        115

SEQ ID NO: 56          moltype = AA  length = 462
FEATURE                Location/Qualifiers
source                 1..462
                       mol_type = protein
                       organism = Synthetic construct
SEQUENCE: 56
QVQLQQSGPG LVKPSQTLSL TCAISGDSVS GYSAAWNWIR QSPSRGLEWL GRTYYRSKWY    60
NDYAVSVKSR ITINPDTSKN QFSLQLNSVT PEDTAVYYCA RDYYGSESYY NRGYYYYGMD   120
VWGQGTTVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKKV EPKSCDKTHT   240
CPPCPAPEAA GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR EEMTKNQVSL TCLVKGFYPS DIAVEWESNG QPENNYKTTP PVLDSDGSFF   420
LYSKLTVDKS RWQQGNVFSC SVMHEALHNH YTQKSLSLSP GK                     462

SEQ ID NO: 57          moltype = AA  length = 214
FEATURE                Location/Qualifiers
source                 1..214
                       mol_type = protein
                       organism = Synthetic construct
SEQUENCE: 57
AIQLTQSPSS LSASVGDRVT ITCRASPGIS SALAWYQQKP GKAPKLLMYD ESSQESGVPS    60
RFSGSGSGTD FTLTISSLQP EDFATYYCQQ FNDYPLTFGG GTKVEIKRTV AAPSVFIFPP   120
```

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 58           moltype = AA  length = 462
FEATURE                 Location/Qualifiers
source                  1..462
                        mol_type = protein
                        organism = Synthetic construct
SEQUENCE: 58
QVQLQQSGPG LVKPSQTLSL TCAISGDSVS GYSAAWNWIR QSPSRGLEWL GRTYYRSKWY    60
NDYAVSVKSR ITINPDTSKN QFSLQLNSVT PEDTAVYYCA RDYYGSESYY NRGYYYYGMD    120
VWGQGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKKV EPKSCDKTHT    240
CPPCPAPEAA GGPSVFLFPP KPKDTLMISR TPEVTCVVVD VSHEDPEVKF NWYVDGVEVH    300
NAKTKPREEQ YASTYRVVSV LTVLHQDWLN GKEYKCKVSN KALPAPIEKT ISKAKGQPRE    360
PQVYTLPPSR EEMTKNQVSL TCLVKGFYPS DIAVEWESNG QPENNYKTTP PVLDSDGSFF    420
LYSKLTVDKS RWQQGNVFSC SVMHEALHNH YTQKSLSLSP GK                       462

SEQ ID NO: 59           moltype = AA  length = 446
FEATURE                 Location/Qualifiers
source                  1..446
                        mol_type = protein
                        organism = Synthetic construct
SEQUENCE: 59
EVQLVESGGG SVQPGGSLRL SCAASGFTFS SYGMSWIRQA PGKGLEWISY ISSSGGHTYY    60
ADSVKGRFTI SRDNAKNSLY LQMNSLRAED TAVYYCARGS GSFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PEAAGAPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 60           moltype = AA  length = 214
FEATURE                 Location/Qualifiers
source                  1..214
                        mol_type = protein
                        organism = Synthetic construct
SEQUENCE: 60
DIVMTQSPSS LSASVGDRVT ITCQASQDIT NYLSWYQQKP GKAPKLLISD ASNLETGIPS    60
RFSGSGSGTD FTFTISSLQP EDIATYYCQQ YDTLPITFGQ GTRLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 61           moltype = AA  length = 449
FEATURE                 Location/Qualifiers
source                  1..449
                        mol_type = protein
                        organism = Synthetic construct
SEQUENCE: 61
QVQLVQSGSE VKKPGASVRV SCKVSGSTVK ELSMHWVRQA PGKGLEWMGG YDPEDGESIF    60
AQKFQGRVNM TEDRSTDTAY MELSSLRSED TAVYYCATDL NWEDAFDVWG QGTMVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPEAAGAP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 62           moltype = AA  length = 220
FEATURE                 Location/Qualifiers
source                  1..220
                        mol_type = protein
                        organism = Synthetic construct
SEQUENCE: 62
QSVLTQPPSV SAAPGQKVTI SCSGSGSNIG NYYVAWYQQF PGTAPKLLIY DNNKRPSGIP    60
DRFSGSKSGT SATLGITGLQ TGDEADYYCG TWDTSLTAGD IYVFGTGTKV TVLRTVAAPS    120
VFIFPPSDEQ LKSGTASVVC LLNNFYPREA KVQWKVDNAL QSGNSQESVT EQDSKDSTYS    180
LSSTLTLSKA DYEKHKVYAC EVTHQGLSSP VTKSFNRGEC                          220

SEQ ID NO: 63           moltype = AA  length = 451
FEATURE                 Location/Qualifiers
source                  1..451
                        mol_type = protein
                        organism = Synthetic construct
SEQUENCE: 63
EVQLVESGGG LSQPGNSLQL SCEASGFTFS NHDMNWVRQA PGKGLEWVAY ISSASGLISY    60
ADSVRGRFTI SRDNAKNSLF LQMNNLKSED TAMYYCARDP AYSGNYALDF WGQGTQVTVS    120
SASTKGPSVF PLAPSSKSTS GGTAALGCLV KDYFPEPVTV SWNSGALTSG VHTFPAVLQS    180
```

```
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 64           moltype = AA   length = 222
FEATURE                 Location/Qualifiers
source                  1..222
                        mol_type = protein
                        organism = Synthetic construct
SEQUENCE: 64
QPVLTQSPSA SASLSGSVKL TCTLSSELSS YTIVWYQQQP DKAPKYVMYL KSDGSHGKGD     60
GIPDRFSGSS SGAHRYLSVS NVQSEDDATY FCGAGYTLAG QYGWVFGSGT KVTVLRTVAA    120
PSVFIFPPSD EQLKSGTASV VCLLNNFYPR EAKVQWKVDN ALQSGNSQES VTEQDSKDST    180
YSLSSTLTLS KADYEKHKVY ACEVTHQGLS SPVTKSFNRG EC                       222

SEQ ID NO: 65           moltype = AA   length = 462
FEATURE                 Location/Qualifiers
source                  1..462
                        mol_type = protein
                        organism = Synthetic construct
SEQUENCE: 65
QVQLQQSGPG LVKPSQTLSL TCAISGDSVS GYSAAWNWIR QSPSRGLEWL GRTYYRSKWY     60
NDYAVSVKSR ITINPDTSKN QFSLQLNSVT PEDTAVYYCA RDYYGSESYY NRGYYYYGMD    120
VWGQGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKKV EPKSCDKTHT    240
CPPCPAPEAA GGPSVFLFPP KPKDTLMISR TPEVTCVVVD VSHEDPEVKF NWYVDGVEVH    300
NAKTKPREEQ YNSTYRVVSV LTVLHQDWLN GKEYKCKVSN KALPAPIEKT ISKAKGQPRE    360
PQVYTLPPCR EEMTKNQVSL WCLVKGFYPS DIAVEWESNG QPENNYKTTP PVLDSDGSFF    420
LYSKLTVDKS RWQQGNVFSC SVMHEALHNH YTQKSLSLSP GK                       462

SEQ ID NO: 66           moltype = AA   length = 446
FEATURE                 Location/Qualifiers
source                  1..446
                        mol_type = protein
                        organism = Synthetic construct
SEQUENCE: 66
EVQLVESGGG SVQPGGSLRL SCAASGFTFS SYGMSWIRQA PGKGLEWISY ISSSGGHTYY     60
ADSVKGRFTI SRDNAKNSLY LQMNSLRAED TAVYYCARGS GSFDYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVCTL PPSREEMTKN    360
QVSLSCAVKG FYPSDIAVEW ESNGQPENNY KTTPPVLDSD GSFFLVSKLT VDKSRWQQGN    420
VFSCSVMHEA LHNHYTQKSL SLSPGK                                         446

SEQ ID NO: 67           moltype = AA   length = 449
FEATURE                 Location/Qualifiers
source                  1..449
                        mol_type = protein
                        organism = Synthetic construct
SEQUENCE: 67
QVQLVQSGSE VKKPGASVRV SCKVSGSTVK ELSMHWVRQA PGKGLEWMGG YDPEDGESIF     60
AQKFQGRVNM TEDRSTDTAY MELSSLRSED TAVYYCATDL NWEDAFDVWG QGTMVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPEAAGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV CTLPPSREEM    360
TKNQVSLSCA VKGFYPSDIA VEWESNGQPE NNYKTTPPVL DSDGSFFLVS KLTVDKSRWQ    420
QGNVFSCSVM HEALHNHYTQ KSLSLSPGK                                      449

SEQ ID NO: 68           moltype = AA   length = 451
FEATURE                 Location/Qualifiers
source                  1..451
                        mol_type = protein
                        organism = Synthetic construct
SEQUENCE: 68
EVQLVESGGG LSQPGNSLQL SCEASGFTFS NHDMNWVRQA PGKGLEWVAY ISSASGLISY     60
ADSVRGRFTI SRDNAKNSLF LQMNNLKSED TAMYYCARDP AYSGNYALDF WGQGTQVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVCTLPPSRE    360
EMTKNQVSLS CAVKGFYPSD IAVEWESNGQ PENNYKTTPP VLDSDGSFFL VSKLTVDKSR    420
WQQGNVFSCS VMHEALHNHY TQKSLSLSPG K                                   451

SEQ ID NO: 69           moltype = AA   length = 330
FEATURE                 Location/Qualifiers
```

```
source                       1..330
                             mol_type = protein
                             organism = Homo sapiens
SEQUENCE: 69
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 70                moltype = AA  length = 330
FEATURE                      Location/Qualifiers
source                       1..330
                             mol_type = protein
                             organism = Homo sapiens
SEQUENCE: 70
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 71                moltype = AA  length = 326
FEATURE                      Location/Qualifiers
source                       1..326
                             mol_type = protein
                             organism = Homo sapiens
SEQUENCE: 71
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPGK                                        326

SEQ ID NO: 72                moltype = AA  length = 377
FEATURE                      Location/Qualifiers
source                       1..377
                             mol_type = protein
                             organism = Homo sapiens
SEQUENCE: 72
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC   120
DTPPPCPRCP EPKSCDTPPP CPRCPEPKSC DTPPPCPRCP APELLGGPSV FLFPPKPKDT   180
LMISRTPEVT CVVVDVSHED PEVQFKWYVD GVEVHNAKTK PREEQYNSTF RVVSVLTVLH   240
QDWLNGKEYK CKVSNKALPA PIEKTISKTK GQPREPQVYT LPPSREEMTK NQVSLTCLVK   300
GFYPSDIAVE WESSGQPENN YNTTPPMLDS DGSFFLYSKL TVDKSRWQQG NIFSCSVMHE   360
ALHNRFTQKS LSLSPGK                                                  377

SEQ ID NO: 73                moltype = AA  length = 327
FEATURE                      Location/Qualifiers
source                       1..327
                             mol_type = protein
                             organism = Homo sapiens
SEQUENCE: 73
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 74                moltype = AA  length = 106
FEATURE                      Location/Qualifiers
source                       1..106
                             mol_type = protein
                             organism = Homo sapiens
SEQUENCE: 74
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                  106

SEQ ID NO: 75                moltype = AA  length = 107
FEATURE                      Location/Qualifiers
source                       1..107
                             mol_type = protein
                             organism = Homo sapiens
SEQUENCE: 75
```

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 76          moltype = AA   length = 105
FEATURE                Location/Qualifiers
source                 1..105
                       mol_type = protein
                       organism = Homo sapiens
SEQUENCE: 76
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTEC                  105

SEQ ID NO: 77          moltype = AA   length = 7
FEATURE                Location/Qualifiers
source                 1..7
                       mol_type = protein
                       organism = Synthetic construct
SEQUENCE: 77
YSGAFDH                                                              7

SEQ ID NO: 78          moltype = AA   length = 7
FEATURE                Location/Qualifiers
source                 1..7
                       mol_type = protein
                       organism = Synthetic construct
SEQUENCE: 78
YSGAFDR                                                              7

SEQ ID NO: 79          moltype = AA   length = 11
FEATURE                Location/Qualifiers
source                 1..11
                       mol_type = protein
                       organism = Synthetic construct
SEQUENCE: 79
QASQDISNYL S                                                        11

SEQ ID NO: 80          moltype = AA   length = 9
FEATURE                Location/Qualifiers
source                 1..9
                       mol_type = protein
                       organism = Synthetic construct
SEQUENCE: 80
QQYDNLPIT                                                            9

SEQ ID NO: 81          moltype = AA   length = 5
FEATURE                Location/Qualifiers
source                 1..5
                       mol_type = protein
                       organism = Synthetic construct
SEQUENCE: 81
SYGMN                                                                5

SEQ ID NO: 82          moltype = AA   length = 9
FEATURE                Location/Qualifiers
source                 1..9
                       mol_type = protein
                       organism = Synthetic construct
SEQUENCE: 82
ARGQGPFEY                                                            9

SEQ ID NO: 83          moltype = AA   length = 11
FEATURE                Location/Qualifiers
source                 1..11
                       mol_type = protein
                       organism = Synthetic construct
SEQUENCE: 83
QASQDISNYL S                                                        11

SEQ ID NO: 84          moltype = AA   length = 9
FEATURE                Location/Qualifiers
source                 1..9
                       mol_type = protein
                       organism = Synthetic construct
SEQUENCE: 84
QQYDNLPIT                                                            9

SEQ ID NO: 85          moltype = AA   length = 9
FEATURE                Location/Qualifiers
source                 1..9
```

```
                            mol_type = protein
                            organism = Synthetic construct
SEQUENCE: 85
ARGSGSFDY                                                                9

SEQ ID NO: 86               moltype = AA    length = 11
FEATURE                     Location/Qualifiers
source                      1..11
                            mol_type = protein
                            organism = Synthetic construct
SEQUENCE: 86
QASQDISNYL S                                                            11

SEQ ID NO: 87               moltype = AA    length = 9
FEATURE                     Location/Qualifiers
source                      1..9
                            mol_type = protein
                            organism = Synthetic construct
SEQUENCE: 87
QQYDNLPIT                                                                9

SEQ ID NO: 88               moltype = AA    length = 9
FEATURE                     Location/Qualifiers
source                      1..9
                            mol_type = protein
                            organism = Synthetic construct
SEQUENCE: 88
ARYSGAFDH                                                                9

SEQ ID NO: 89               moltype = AA    length = 9
FEATURE                     Location/Qualifiers
source                      1..9
                            mol_type = protein
                            organism = Synthetic construct
SEQUENCE: 89
ARYSGAFDR                                                                9

SEQ ID NO: 90               moltype = AA    length = 6
FEATURE                     Location/Qualifiers
source                      1..6
                            mol_type = protein
                            organism = Synthetic construct
SEQUENCE: 90
QDISNY                                                                   6

SEQ ID NO: 91               moltype = AA    length = 9
FEATURE                     Location/Qualifiers
source                      1..9
                            mol_type = protein
                            organism = Synthetic construct
SEQUENCE: 91
ARGQGPFEY                                                                9

SEQ ID NO: 92               moltype = AA    length = 132
FEATURE                     Location/Qualifiers
source                      1..132
                            mol_type = protein
                            organism = Synthetic construct
SEQUENCE: 92
QVQLQQSGPG LVKPSQTLSL TCAISGDSVS SYSAAWNWIR QSPSRGLEWL GRTYYRSKWF        60
NDYAVSVKSR ITINPDTSKN QFSLQLNSVT PEDTAVYYCA RDYYGSESYY NRGYYYYGLD       120
VWGQGTTVTV SS                                                           132

SEQ ID NO: 93               moltype = AA    length = 108
FEATURE                     Location/Qualifiers
source                      1..108
                            mol_type = protein
                            organism = Synthetic construct
SEQUENCE: 93
AIQLTQSPSS LSASVGDRVT ITCRASPSIS SALAWYQQKP GKAPKLLMYD ESSQEGSVPS        60
RFSGSGSGTD FTLTISSLQP EDFATYYCQQ FNEYPLTFGG GTKVEIKR                    108

SEQ ID NO: 94               moltype = AA    length = 116
FEATURE                     Location/Qualifiers
source                      1..116
                            mol_type = protein
                            organism = Synthetic construct
SEQUENCE: 94
EVQLVESGGG SVQPGGSLRL SCAASGFTFS SYGMSWIRQA PGKGLEWVSY ISSSGGHTYY        60
```

```
ADSVKGRFTI SRDNAKNSLY LQMNSLRAED TAVYYCARYS GAFDHWGQGT LVTVSS         116

SEQ ID NO: 95           moltype = AA   length = 108
FEATURE                 Location/Qualifiers
source                  1..108
                        mol_type = protein
                        organism = Synthetic construct
SEQUENCE: 95
DIVMTQSPSS LSASVGDRVT ITCQASQDIT NYLSWYQQKP GKAPKLLIND ASNLETGVPS      60
RFSGSGSGTD FTFTISSLQP EDIATYYCQQ YDTLPITFGQ GTRLEIKR                  108

SEQ ID NO: 96           moltype = AA   length = 116
FEATURE                 Location/Qualifiers
source                  1..116
                        mol_type = protein
                        organism = Synthetic construct
SEQUENCE: 96
EVQLVESGGG SVQPGGSLRL SCAASGFTFS SYGMSWVRQA PGKGLEWISY ISSSGGHTYY      60
ADSVKGRFTI SRDNAKNSLY LQMNSLRAED TAVYYCARYS GAFDRWGQGT PVTVSS         116

SEQ ID NO: 97           moltype = AA   length = 108
FEATURE                 Location/Qualifiers
source                  1..108
                        mol_type = protein
                        organism = Synthetic construct
SEQUENCE: 97
DIVMTQSPSS LSASVGDRVT ITCQASQDIS NYLSWYQQKP GKAPKLLISD ASNLETGVPS      60
RFSGSGSGTD FTFTISSLQP EDIATYYCQQ YDNLPITFGQ GTRLEIKR                  108

SEQ ID NO: 98           moltype = AA   length = 116
FEATURE                 Location/Qualifiers
source                  1..116
                        mol_type = protein
                        organism = Synthetic construct
SEQUENCE: 98
EVQLVESGGG SVQPGGSLRL SCAASGFTFS SYGMNWIRQA PGKGLEWITY ISSSGGHTYY      60
ADSVKGRFTI SRDNAKNSLY LQMNSLRAED TAVYYCARGQ GPFEYWGQGT LVTVSS         116

SEQ ID NO: 99           moltype = AA   length = 108
FEATURE                 Location/Qualifiers
source                  1..108
                        mol_type = protein
                        organism = Synthetic construct
SEQUENCE: 99
DIVMTQSPSS LSASVGDRVT ITCQASQDIS NYLSWYQQKP GKAPKLLIND ASNLETGVPS      60
RFSGSGSGTD FTFTISSLQP EDIATYYCQQ YDNLPITFGQ GTRLEIKR                  108

SEQ ID NO: 100          moltype = AA   length = 116
FEATURE                 Location/Qualifiers
source                  1..116
                        mol_type = protein
                        organism = Synthetic construct
SEQUENCE: 100
EVQLVESGGG SVQPGGSLRL SCAASGFTFS SYGMSWVRQA PGKGLEWISY ISSSGGHTYY      60
ADSVKGQFTI SRDNAKNSLY LQMNSLRAED TAVYYCARGS GSFDYWGQGT LVTVSS         116

SEQ ID NO: 101          moltype = AA   length = 15
FEATURE                 Location/Qualifiers
source                  1..15
                        mol_type = protein
                        organism = Synthetic construct
SEQUENCE: 101
GGRGSGGGGS GSGGS                                                       15

SEQ ID NO: 102          moltype = AA   length = 15
FEATURE                 Location/Qualifiers
source                  1..15
                        mol_type = protein
                        organism = Synthetic construct
SEQUENCE: 102
GGGGSGGGGS GGGGS                                                       15

SEQ ID NO: 103          moltype = AA   length = 239
FEATURE                 Location/Qualifiers
source                  1..239
                        mol_type = protein
                        organism = Synthetic construct
SEQUENCE: 103
EVQLVESGGG SVQPGGSLRL SCAASGFTFS SYGMSWIRQA PGKGLEWVSY ISSSGGHTYY      60
```

```
ADSVKGRFTI SRDNAKNSLY LQMNSLRAED TAVYYCARYS GAFDHWGQGT LVTVSSGGRG   120
SGGGGSGSGG SDIVMTQSPS SLSASVGDRV TITCQASQDI TNYLSWYQQK PGKAPKLLIN   180
DASNLETGVP SRFSGSGSGT DFTFTISSLQ PEDIATYYCQ QYDTLPITFG QGTRLEIKR    239

SEQ ID NO: 104          moltype = AA   length = 239
FEATURE                 Location/Qualifiers
source                  1..239
                        mol_type = protein
                        organism = Synthetic construct
SEQUENCE: 104
EVQLVESGGG SVQPGGSLRL SCAASGFTFS SYGMSWVRQA PGKGLEWISY ISSSGGHTYY   60
ADSVKGRFTI SRDNAKNSLY LQMNSLRAED TAVYYCARYS GAFDRWGQGT PVTVSSGGRG   120
SGGGGSGSGG SDIVMTQSPS SLSASVGDRV TITCQASQDI SNYLSWYQQK PGKAPKLLIS   180
DASNLETGVP SRFSGSGSGT DFTFTISSLQ PEDIATYYCQ QYDNLPITFG QGTRLEIKR    239

SEQ ID NO: 105          moltype = AA   length = 239
FEATURE                 Location/Qualifiers
source                  1..239
                        mol_type = protein
                        organism = Synthetic construct
SEQUENCE: 105
EVQLVESGGG SVQPGGSLRL SCAASGFTFS SYGMNWIRQA PGKGLEWITY ISSSGGHTYY   60
ADSVKGRFTI SRDNAKNSLY LQMNSLRAED TAVYYCARGQ GPFEYWGQGT LVTVSSGGRG   120
SGGGGSGSGG SDIVMTQSPS SLSASVGDRV TITCQASQDI SNYLSWYQQK PGKAPKLLIN   180
DASNLETGVP SRFSGSGSGT DFTFTISSLQ PEDIATYYCQ QYDNLPITFG QGTRLEIKR    239

SEQ ID NO: 106          moltype = AA   length = 239
FEATURE                 Location/Qualifiers
source                  1..239
                        mol_type = protein
                        organism = Synthetic construct
SEQUENCE: 106
EVQLVESGGG SVQPGGSLRL SCAASGFTFS SYGMSWVRQA PGKGLEWISY ISSSGGHTYY   60
ADSVKGRFTI SRDNAKNSLY LQMNSLRAED TAVYYCARGS GSPDYWGQGT LVTVSSGGRG   120
SGGGGSGSGG SDIVMTQSPS SLSASVGDRV TITCQASQDI SNYLSWYQQK PGKAPKLLIS   180
DASNLETGVP SRFSGSGSGT DFTFTISSLQ PEDIATYYCQ QYDNLPITFG QGTRLEIKR    239

SEQ ID NO: 107          moltype = AA   length = 239
FEATURE                 Location/Qualifiers
source                  1..239
                        mol_type = protein
                        organism = Synthetic construct
SEQUENCE: 107
EVQLVESGGG SVQPGGSLRL SCAASGFTFS SYGMSWIRQA PGKGLEWVSY ISSSGGHTYY   60
ADSVKGRFTI SRDNAKNSLY LQMNSLRAED TAVYYCARYS GAFDHWGQGT LVTVSSGGGG   120
SGGGGSGGGG SDIVMTQSPS SLSASVGDRV TITCQASQDI TNYLSWYQQK PGKAPKLLIN   180
DASNLETGVP SRFSGSGSGT DFTFTISSLQ PEDIATYYCQ QYDTLPITFG QGTRLEIKR    239

SEQ ID NO: 108          moltype = AA   length = 239
FEATURE                 Location/Qualifiers
source                  1..239
                        mol_type = protein
                        organism = Synthetic construct
SEQUENCE: 108
EVQLVESGGG SVQPGGSLRL SCAASGFTFS SYGMSWVRQA PGKGLEWISY ISSSGGHTYY   60
ADSVKGRFTI SRDNAKNSLY LQMNSLRAED TAVYYCARYS GAFDRWGQGT PVTVSSGGGG   120
SGGGGSGGGG SDIVMTQSPS SLSASVGDRV TITCQASQDI SNYLSWYQQK PGKAPKLLIS   180
DASNLETGVP SRFSGSGSGT DFTFTISSLQ PEDIATYYCQ QYDNLPITFG QGTRLEIKR    239

SEQ ID NO: 109          moltype = AA   length = 239
FEATURE                 Location/Qualifiers
source                  1..239
                        mol_type = protein
                        organism = Synthetic construct
SEQUENCE: 109
EVQLVESGGG SVQPGGSLRL SCAASGFTFS SYGMNWIRQA PGKGLEWITY ISSSGGHTYY   60
ADSVKGRFTI SRDNAKNSLY LQMNSLRAED TAVYYCARGQ GPFEYWGQGT LVTVSSGGGG   120
SGGGGSGGGG SDIVMTQSPS SLSASVGDRV TITCQASQDI SNYLSWYQQK PGKAPKLLIN   180
DASNLETGVP SRFSGSGSGT DFTFTISSLQ PEDIATYYCQ QYDNLPITFG QGTRLEIKR    239

SEQ ID NO: 110          moltype = AA   length = 239
FEATURE                 Location/Qualifiers
source                  1..239
                        mol_type = protein
                        organism = Synthetic construct
SEQUENCE: 110
EVQLVESGGG SVQPGGSLRL SCAASGFTFS SYGMSWVRQA PGKGLEWISY ISSSGGHTYY   60
ADSVKGQFTI SRDNAKNSLY LQMNSLRAED TAVYYCARGS GSFDYWGQGT LVTVSSGGGG   120
SGGGGSGGGG SDIVMTQSPS SLSASVGDRV TITCQASQDI SNYLSWYQQK PGKAPKLLIS   180
```

DASNLETGVP SRFSGSGSGT DFTFTISSLQ PEDIATYYCQ QYDNLPITFG QGTRLEIKR    239

```
SEQ ID NO: 111           moltype = AA   length = 239
FEATURE                  Location/Qualifiers
source                   1..239
                         mol_type = protein
                         organism = Synthetic construct
SEQUENCE: 111
```
EVQLVESGGG SVQPGGSLRL SCAASGFTFS SYGMSWIRQA PGKGLEWVSY ISSSGGHTYY    60
ADSVKGRFTI SRDNAKNSLY LQMNSLRAED TAVYYCARYS GAFDHWGQGT LVTVSSGGRG    120
SGGGGSGSGG SDIVMTQSPS SLSASVGDRV TITCQASQDI SNYLSWYQQK PGKAPKLLIS    180
DASNLETGVP SRFSGSGSGT DFTFTISSLQ PEDIATYYCQ QYDNLPITFG QGTRLEIKR     239

```
SEQ ID NO: 112           moltype = AA   length = 239
FEATURE                  Location/Qualifiers
source                   1..239
                         mol_type = protein
                         organism = Synthetic construct
SEQUENCE: 112
```
EVQLVESGGG SVQPGGSLRL SCAASGFTFS SYGMSWIRQA PGKGLEWVSY ISSSGGHTYY    60
ADSVKGRFTI SRDNAKNSLY LQMNSLRAED TAVYYCARYS GAFDHWGQGT LVTVSSGGRG    120
SGGGGSGSGG SDIVMTQSPS SLSASVGDRV TITCQASQDI SNYLSWYQQK PGKAPKLLIN    180
DASNLETGVP SRFSGSGSGT DFTFTISSLQ PEDIATYYCQ QYDNLPITFG QGTRLEIKR     239

```
SEQ ID NO: 113           moltype = AA   length = 239
FEATURE                  Location/Qualifiers
source                   1..239
                         mol_type = protein
                         organism = Synthetic construct
SEQUENCE: 113
```
EVQLVESGGG SVQPGGSLRL SCAASGFTFS SYGMSWVRQA PGKGLEWISY ISSSGGHTYY    60
ADSVKGRFTI SRDNAKNSLY LQMNSLRAED TAVYYCARYS GAFDRWGQGT PVTVSSGGRG    120
SGGGGSGSGG SDIVMTQSPS SLSASVGDRV TITCQASQDI TNYLSWYQQK PGKAPKLLIN    180
DASNLETGVP SRFSGSGSGT DFTFTISSLQ PEDIATYYCQ QYDTLPITFG QGTRLEIKR     239

```
SEQ ID NO: 114           moltype = AA   length = 239
FEATURE                  Location/Qualifiers
source                   1..239
                         mol_type = protein
                         organism = Synthetic construct
SEQUENCE: 114
```
EVQLVESGGG SVQPGGSLRL SCAASGFTFS SYGMSWVRQA PGKGLEWISY ISSSGGHTYY    60
ADSVKGRFTI SRDNAKNSLY LQMNSLRAED TAVYYCARYS GAFDRWGQGT PVTVSSGGRG    120
SGGGGSGSGG SDIVMTQSPS SLSASVGDRV TITCQASQDI SNYLSWYQQK PGKAPKLLIN    180
DASNLETGVP SRFSGSGSGT DFTFTISSLQ PEDIATYYCQ QYDNLPITFG QGTRLEIKR     239

```
SEQ ID NO: 115           moltype = AA   length = 239
FEATURE                  Location/Qualifiers
source                   1..239
                         mol_type = protein
                         organism = Synthetic construct
SEQUENCE: 115
```
EVQLVESGGG SVQPGGSLRL SCAASGFTFS SYGMNWIRQA PGKGLEWITY ISSSGGHTYY    60
ADSVKGRFTI SRDNAKNSLY LQMNSLRAED TAVYYCARGQ GPFEYWGQGT LVTVSSGGRG    120
SGGGGSGSGG SDIVMTQSPS SLSASVGDRV TITCQASQDI TNYLSWYQQK PGKAPKLLIN    180
DASNLETGVP SRFSGSGSGT DFTFTISSLQ PEDIATYYCQ QYDTLPITFG QGTRLEIKR     239

```
SEQ ID NO: 116           moltype = AA   length = 239
FEATURE                  Location/Qualifiers
source                   1..239
                         mol_type = protein
                         organism = Synthetic construct
SEQUENCE: 116
```
EVQLVESGGG SVQPGGSLRL SCAASGFTFS SYGMNWIRQA PGKGLEWITY ISSSGGHTYY    60
ADSVKGRFTI SRDNAKNSLY LQMNSLRAED TAVYYCARGQ GPFEYWGQGT LVTVSSGGRG    120
SGGGGSGSGG SDIVMTQSPS SLSASVGDRV TITCQASQDI SNYLSWYQQK PGKAPKLLIS    180
DASNLETGVP SRFSGSGSGT DFTFTISSLQ PEDIATYYCQ QYDNLPITFG QGTRLEIKR     239

```
SEQ ID NO: 117           moltype = AA   length = 239
FEATURE                  Location/Qualifiers
source                   1..239
                         mol_type = protein
                         organism = Synthetic construct
SEQUENCE: 117
```
EVQLVESGGG SVQPGGSLRL SCAASGFTFS SYGMSWVRQA PGKGLEWISY ISSSGGHTYY    60
ADSVKGQFTI SRDNAKNSLY LQMNSLRAED TAVYYCARGS GSPDYWGQGT LVTVSSGGRG    120
SGGGGSGSGG SDIVMTQSPS SLSASVGDRV TITCQASQDI TNYLSWYQQK PGKAPKLLIN    180
DASNLETGVP SRFSGSGSGT DFTFTISSLQ PEDIATYYCQ QYDTLPITFG QGTRLEIKR     239

```
SEQ ID NO: 118            moltype = AA  length = 239
FEATURE                   Location/Qualifiers
source                    1..239
                          mol_type = protein
                          organism = Synthetic construct
SEQUENCE: 118
EVQLVESGGG SVQPGGSLRL SCAASGFTFS SYGMSWVRQA PGKGLEWISY ISSSGGHTYY    60
ADSVKGQFTI SRDNAKNSLY LQMNSLRAED TAVYYCARGS GSFDYWGQGT LVTVSSGGRG   120
SGGGGSGSGG SDIVMTQSPS SLSASVGDRV TITCQASQDI SNYLSWYQQK PGKAPKLLIN   180
DASNLETGVP SRFSGSGSGT DFTFTISSLQ PEDIATYYCQ QYDNLPITFG QGTRLEIKR    239

SEQ ID NO: 119            moltype = AA  length = 239
FEATURE                   Location/Qualifiers
source                    1..239
                          mol_type = protein
                          organism = Synthetic construct
SEQUENCE: 119
EVQLVESGGG SVQPGGSLRL SCAASGFTFS SYGMSWIRQA PGKGLEWVSY ISSSGGHTYY    60
ADSVKGRFTI SRDNAKNSLY LQMNSLRAED TAVYYCARYS GAFDHWGQGT LVTVSSGGGG   120
SGGGGSGGGG SDIVMTQSPS SLSASVGDRV TITCQASQDI SNYLSWYQQK PGKAPKLLIS   180
DASNLETGVP SRFSGSGSGT DFTFTISSLQ PEDIATYYCQ QYDNLPITFG QGTRLEIKR    239

SEQ ID NO: 120            moltype = AA  length = 239
FEATURE                   Location/Qualifiers
source                    1..239
                          mol_type = protein
                          organism = Synthetic construct
SEQUENCE: 120
EVQLVESGGG SVQPGGSLRL SCAASGFTFS SYGMSWIRQA PGKGLEWVSY ISSSGGHTYY    60
ADSVKGRFTI SRDNAKNSLY LQMNSLRAED TAVYYCARYS GAFDHWGQGT LVTVSSGGGG   120
SGGGGSGGGG SDIVMTQSPS SLSASVGDRV TITCQASQDI SNYLSWYQQK PGKAPKLLIN   180
DASNLETGVP SRFSGSGSGT DFTFTISSLQ PEDIATYYCQ QYDNLPITFG QGTRLEIKR    239

SEQ ID NO: 121            moltype = AA  length = 239
FEATURE                   Location/Qualifiers
source                    1..239
                          mol_type = protein
                          organism = Synthetic construct
SEQUENCE: 121
EVQLVESGGG SVQPGGSLRL SCAASGFTFS SYGMSWVRQA PGKGLEWISY ISSSGGHTYY    60
ADSVKGRFTI SRDNAKNSLY LQMNSLRAED TAVYYCARYS GAFDRWGQGT PVTVSSGGGG   120
SGGGGSGGGG SDIVMTQSPS SLSASVGDRV TITCQASQDI TNYLSWYQQK PGKAPKLLIN   180
DASNLETGVP SRFSGSGSGT DFTFTISSLQ PEDIATYYCQ QYDTLPITFG QGTRLEIKR    239

SEQ ID NO: 122            moltype = AA  length = 239
FEATURE                   Location/Qualifiers
source                    1..239
                          mol_type = protein
                          organism = Synthetic construct
SEQUENCE: 122
EVQLVESGGG SVQPGGSLRL SCAASGFTFS SYGMSWVRQA PGKGLEWISY ISSSGGHTYY    60
ADSVKGRFTI SRDNAKNSLY LQMNSLRAED TAVYYCARYS GAFDRWGQGT PVTVSSGGGG   120
SGGGGSGGGG SDIVMTQSPS SLSASVGDRV TITCQASQDI SNYLSWYQQK PGKAPKLLIN   180
DASNLETGVP SRFSGSGSGT DFTFTISSLQ PEDIATYYCQ QYDNLPITFG QGTRLEIKR    239

SEQ ID NO: 123            moltype = AA  length = 239
FEATURE                   Location/Qualifiers
source                    1..239
                          mol_type = protein
                          organism = Synthetic construct
SEQUENCE: 123
EVQLVESGGG SVQPGGSLRL SCAASGFTFS SYGMNWIRQA PGKGLEWITY ISSSGGHTYY    60
ADSVKGRFTI SRDNAKNSLY LQMNSLRAED TAVYYCARGQ GPFEYWGQGT LVTVSSGGGG   120
SGGGGSGSGG SDIVMTQSPS SLSASVGDRV TITCQASQDI TNYLSWYQQK PGKAPKLLIN   180
DASNLETGVP SRFSGSGSGT DFTFTISSLQ PEDIATYYCQ QYDTLPITFG QGTRLEIKR    239

SEQ ID NO: 124            moltype = AA  length = 239
FEATURE                   Location/Qualifiers
source                    1..239
                          mol_type = protein
                          organism = Synthetic construct
SEQUENCE: 124
EVQLVESGGG SVQPGGSLRL SCAASGFTFS SYGMNWIRQA PGKGLEWITY ISSSGGHTYY    60
ADSVKGRFTI SRDNAKNSLY LQMNSLRAED TAVYYCARGQ GPFEYWGQGT LVTVSSGGGG   120
SGGGGSGGGG SDIVMTQSPS SLSASVGDRV TITCQASQDI SNYLSWYQQK PGKAPKLLIS   180
DASNLETGVP SRFSGSGSGT DFTFTISSLQ PEDIATYYCQ QYDNLPITFG QGTRLEIKR    239

SEQ ID NO: 125            moltype = AA  length = 239
FEATURE                   Location/Qualifiers
```

```
                        source              1..239
                                            mol_type = protein
                                            organism = Synthetic construct
SEQUENCE: 125
EVQLVESGGG SVQPGGSLRL SCAASGFTFS SYGMSWVRQA PGKGLEWISY ISSSGGHTYY   60
ADSVKGQFTI SRDNAKNSLY LQMNSLRAED TAVYYCARGS GSFDYWGQGT LVTVSSGGGG  120
SGGGGSGGGG SDIVMTQSPS SLSASVGDRV TITCQASQDI TNYLSWYQQK PGKAPKLLIN  180
DASNLETGVP SRFSGSGSGT DFTFTISSLQ PEDIATYYCQ QYDTLPITFG QGTRLEIKR   239

SEQ ID NO: 126          moltype = AA  length = 239
FEATURE                 Location/Qualifiers
source                  1..239
                        mol_type = protein
                        organism = Synthetic construct
SEQUENCE: 126
EVQLVESGGG SVQPGGSLRL SCAASGFTFS SYGMSWVRQA PGKGLEWISY ISSSGGHTYY   60
ADSVKGQFTI SRDNAKNSLY LQMNSLRAED TAVYYCARGS GSFDYWGQGT LVTVSSGGGG  120
SGGGGSGGGG SDIVMTQSPS SLSASVGDRV TITCQASQDI SNYLSWYQQK PGKAPKLLIN  180
DASNLETGVP SRFSGSGSGT DFTFTISSLQ PEDIATYYCQ QYDNLPITFG QGTRLEIKR   239

SEQ ID NO: 127          moltype = AA  length = 446
FEATURE                 Location/Qualifiers
source                  1..446
                        mol_type = protein
                        organism = Synthetic construct
SEQUENCE: 127
EVQLVESGGG SVQPGGSLRL SCAASGFTFS SYGMSWIRQA PGKGLEWVSY ISSSGGHTYY   60
ADSVKGRFTI SRDNAKNSLY LQMNSLRAED TAVYYCARYS GAFDHWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGAPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 128          moltype = AA  length = 214
FEATURE                 Location/Qualifiers
source                  1..214
                        mol_type = protein
                        organism = Synthetic construct
SEQUENCE: 128
DIVMTQSPSS LSASVGDRVT ITCQASQDIT NYLSWYQQKP GKAPKLLIND ASNLETGVPS   60
RFSGSGSGTD FTFTISSLQP EDIATYYCQQ YDTLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 129          moltype = AA  length = 446
FEATURE                 Location/Qualifiers
source                  1..446
                        mol_type = protein
                        organism = Synthetic construct
SEQUENCE: 129
EVQLVESGGG SVQPGGSLRL SCAASGFTFS SYGMSWVRQA PGKGLEWISY ISSSGGHTYY   60
ADSVKGRFTI SRDNAKNSLY LQMNSLRAED TAVYYCARYS GAFDRWGQGT PVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGAPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 130          moltype = AA  length = 214
FEATURE                 Location/Qualifiers
source                  1..214
                        mol_type = protein
                        organism = Synthetic construct
SEQUENCE: 130
DIVMTQSPSS LSASVGDRVT ITCQASQDIS NYLSWYQQKP GKAPKLLISD ASNLETGVPS   60
RFSGSGSGTD FTFTISSLQP EDIATYYCQQ YDNLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 131          moltype = AA  length = 446
FEATURE                 Location/Qualifiers
source                  1..446
                        mol_type = protein
                        organism = Synthetic construct
SEQUENCE: 131
EVQLVESGGG SVQPGGSLRL SCAASGFTFS SYGMNWIRQA PGKGLEWITY ISSSGGHTYY   60
```

```
ADSVKGRFTI SRDNAKNSLY LQMNSLRAED TAVYYCARGQ GPFEYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PEAAGAPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 132          moltype = AA   length = 214
FEATURE                 Location/Qualifiers
source                  1..214
                        mol_type = protein
                        organism = Synthetic construct
SEQUENCE: 132
DIVMTQSPSS LSASVGDRVT ITCQASQDIS NYLSWYQQKP GKAPKLLIND ASNLETGVPS    60
RFSGSGSGTD FTFTISSLQP EDIATYYCQQ YDNLPITFGQ GTRLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 133          moltype = AA   length = 446
FEATURE                 Location/Qualifiers
source                  1..446
                        mol_type = protein
                        organism = Synthetic construct
SEQUENCE: 133
EVQLVESGGG SVQPGGSLRL SCAASGFTFS SYGMSWVRQA PGKGLEWISY ISSSGGHTYY    60
ADSVKGQFTI SRDNAKNSLY LQMNSLRAED TAVYYCARGS GSFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PEAAGAPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 134          moltype = AA   length = 462
FEATURE                 Location/Qualifiers
source                  1..462
                        mol_type = protein
                        organism = Synthetic construct
SEQUENCE: 134
QVQLQQSGPG LVKPSQTLSL TCAISGDSVS GYSAAWNWIR QSPSRGLEWL GRTYYRSKWY    60
NDYAVSVKSR ITINPDTSKN QFSLQLNSVT PEDTAVYYCA RDYYGSESYY NRGYYYYGMD   120
VWGQGTTVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKKV EPKSCDKTHT   240
CPPCPAPEAA GAPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR EEMTKNQVSL TCLVKGFYPS DIAVEWESNG QPENNYKTTP PVLDSDGSFF   420
LYSKLTVDKS RWQQGNVFSC SVMHEALHNH YTQKSLSLSP GK                      462

SEQ ID NO: 135          moltype = AA   length = 462
FEATURE                 Location/Qualifiers
source                  1..462
                        mol_type = protein
                        organism = Synthetic construct
SEQUENCE: 135
QVQLQQSGPG LVKPSQTLSL TCAISGDSVS GYSAAWNWIR QSPSRGLEWL GRTYYRSKWY    60
NDYAVSVKSR ITINPDTSKN QFSLQLNSVT PEDTAVYYCA RDYYGSESYY NRGYYYYGMD   120
VWGQGTTVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSNTKVDKKV EPKSCDKTHT   240
CPPCPAPELL GGPSVFLFPP KPKDTLMISR TPEVTCVVVD VSHEDPEVKF NWYVDGVEVH   300
NAKTKPREEQ YNSTYRVVSV LTVLHQDWLN GKEYKCKVSN KALPAPIEKT ISKAKGQPRE   360
PQVYTLPPSR EEMTKNQVSL TCLVKGFYPS DIAVEWESNG QPENNYKTTP PVLDSDGSFF   420
LYSKLTVDKS RWQQGNVFSC SVMHEALHNH YTQKSLSLSP GK                      462

SEQ ID NO: 136          moltype = AA   length = 462
FEATURE                 Location/Qualifiers
source                  1..462
                        mol_type = protein
                        organism = Synthetic construct
SEQUENCE: 136
QVQLQQSGPG LVKPSQTLSL TCAISGDSVS GYSAAWNWIR QSPSRGLEWL GRTYYRSKWY    60
NDYAVSVKSR ITINPDTSKN QFSLQLNSVT PEDTAVYYCA RDYYGSESYY NRGYYYYGMD   120
VWGQGTTVTV SSASTKGPSV FPLAPSSKST SGGTAALGCL VKDYFPEPVT VSWNSGALTS   180
GVHTFPAVLQ SSGLYSLSSV VTVPSSSLGT QTYICNVNHK PSDTKVDKKV EPKSCDKTHT   240
CPPCPAPEAA GGPSVFLFPP KPKDTLMISR TPEVTCVVVD VSHEDPEVKF NWYVDGVEVH   300
NAKTKPREEE YNSTYRVVSV LTVLHQDWLN GKEYKCKVSN KALPAPIEKT ISKAKGQPRE   360
PQVYTLPPCR EEMTKNQVSL WCLVKGFYPS DIAVEWESDG QPENNYKTTP PVLDSDGSFF   420
LYSKLTVDKS RWEQGDVFSC SVMHEALHNH YTQKSLSLSP GK                      462
```

```
SEQ ID NO: 137          moltype = AA  length = 446
FEATURE                 Location/Qualifiers
source                  1..446
                        mol_type = protein
                        organism = Synthetic construct
SEQUENCE: 137
EVQLVESGGG SVQPGGSLRL SCAASGFTFS SYGMSWIRQA PGKGLEWVSY ISSSGGHTYY    60
ADSVKGRFTI SRDNAKNSLY LQMNSLRAED TAVYYCARYS GAFDHWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PEAAGGPSVF   240
LFPPKPKDTL MISRTPEVTC VVVDVSHEDP EVKFNWYVDG VEVHNAKTKP REEQYASTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 138          moltype = AA  length = 7
FEATURE                 Location/Qualifiers
source                  1..7
                        mol_type = protein
                        organism = Synthetic construct
SEQUENCE: 138
SYSAAWN                                                              7

SEQ ID NO: 139          moltype = AA  length = 18
FEATURE                 Location/Qualifiers
source                  1..18
                        mol_type = protein
                        organism = Synthetic construct
SEQUENCE: 139
RTYYRSKWFN DYAVSVKS                                                 18

SEQ ID NO: 140          moltype = AA  length = 20
FEATURE                 Location/Qualifiers
source                  1..20
                        mol_type = protein
                        organism = Synthetic construct
SEQUENCE: 140
DYYGSESYYN RGYYYYGLDV                                               20

SEQ ID NO: 141          moltype = AA  length = 11
FEATURE                 Location/Qualifiers
source                  1..11
                        mol_type = protein
                        organism = Synthetic construct
SEQUENCE: 141
RASPSISSAL A                                                        11

SEQ ID NO: 142          moltype = AA  length = 7
FEATURE                 Location/Qualifiers
source                  1..7
                        mol_type = protein
                        organism = Synthetic construct
SEQUENCE: 142
DESSQEG                                                              7

SEQ ID NO: 143          moltype = AA  length = 9
FEATURE                 Location/Qualifiers
source                  1..9
                        mol_type = protein
                        organism = Synthetic construct
SEQUENCE: 143
QQFNEYPLT                                                            9

SEQ ID NO: 144          moltype = AA  length = 10
FEATURE                 Location/Qualifiers
source                  1..10
                        mol_type = protein
                        organism = Synthetic construct
SEQUENCE: 144
GDSVSSYSAA                                                          10

SEQ ID NO: 145          moltype = AA  length = 9
FEATURE                 Location/Qualifiers
source                  1..9
                        mol_type = protein
                        organism = Synthetic construct
SEQUENCE: 145
TYYRSKWFN                                                            9
```

```
SEQ ID NO: 146         moltype = AA  length = 22
FEATURE                Location/Qualifiers
source                 1..22
                       mol_type = protein
                       organism = Synthetic construct
SEQUENCE: 146
ARDYYGSESY YNRGYYYYGL DV                                             22

SEQ ID NO: 147         moltype = AA  length = 6
FEATURE                Location/Qualifiers
source                 1..6
                       mol_type = protein
                       organism = Synthetic construct
SEQUENCE: 147
PSISSA                                                                6

SEQ ID NO: 148         moltype =     length =
SEQUENCE: 148
000

SEQ ID NO: 149         moltype = AA  length = 9
FEATURE                Location/Qualifiers
source                 1..9
                       mol_type = protein
                       organism = Synthetic construct
SEQUENCE: 149
QQFNEYPLT                                                             9

SEQ ID NO: 150         moltype = AA  length = 462
FEATURE                Location/Qualifiers
source                 1..462
                       mol_type = protein
                       organism = Synthetic construct
SEQUENCE: 150
QVQLQQSGPG LVKPSQTLSL TCAISGDSVS GYSAAWNWIR QSPSRGLEWL GRTYYRSKWY     60
NDYAVSVKSR ITINPDTSKN QFSLQLNSVT PEDTAVYYCA RDYYGSESYY NRGYYYYGMD    120
VWGQGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKKV EPKSCDKTHT    240
CPPCPAPEAA GAPSVFLFPP KPKDTLYITR EPEVTCVVVD VSHEDPEVKF NWYVDGVEVH    300
NAKTKPREEQ YNSTYRVVSV LTVLHQDWLN GKEYKCKVSN KALPAPIEKT ISKAKGQPRE    360
PQVYTLPPSR EEMTKNQVSL TCLVKGFYPS DIAVEWESNG QPENNYKTTP PVLDSDGSFF    420
LYSKLTVDKS RWQQGNVFSC SVMHEALHNH YTQKSLSLSP GK                       462

SEQ ID NO: 151         moltype = AA  length = 462
FEATURE                Location/Qualifiers
source                 1..462
                       mol_type = protein
                       organism = Synthetic construct
SEQUENCE: 151
QVQLQQSGPG LVKPSQTLSL TCAISGDSVS SYSAAWNWIR QSPSRGLEWL GRTYYRSKWF     60
NDYAVSVKSR ITINPDTSKN QFSLQLNSVT PEDTAVYYCA RDYYGSESYY NRGYYYYGLD    120
VWGQGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKKV EPKSCDKTHT    240
CPPCPAPEAA GAPSVFLFPP KPKDTLMISR TPEVTCVVVD VSHEDPEVKF NWYVDGVEVH    300
NAKTKPREEQ YNSTYRVVSV LTVLHQDWLN GKEYKCKVSN KALPAPIEKT ISKAKGQPRE    360
PQVYTLPPSR EEMTKNQVSL TCLVKGFYPS DIAVEWESNG QPENNYKTTP PVLDSDGSFF    420
LYSKLTVDKS RWQQGNVFSC SVMHEALHNH YTQKSLSLSP GK                       462

SEQ ID NO: 152         moltype = AA  length = 214
FEATURE                Location/Qualifiers
source                 1..214
                       mol_type = protein
                       organism = Synthetic construct
SEQUENCE: 152
AIQLTQSPSS LSASVGDRVT ITCRASPSIS SALAWYQQKP GKAPKLLMYD ESSQEGSVPS     60
RFSGSGSGTD FTLTISSLQP EDFATYYCQQ FNEYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 153         moltype = AA  length = 462
FEATURE                Location/Qualifiers
source                 1..462
                       mol_type = protein
                       organism = Synthetic construct
SEQUENCE: 153
QVQLQQSGPG LVKPSQTLSL TCAISGDSVS GYSAAWNWIR QSPSRGLEWL GRTYYRSKWY     60
NDYAVSVKSR ITINPDTSKN QFSLQLNSVT PEDTAVYYCA RDYYGSESYY NRGYYYYGMD    120
VWGQGTTVTV SSASTKGPSV FPLAPSSKST SGGTAALGCL VKDYFPEPVT VSWNSGALTS    180
GVHTFPAVLQ SSGLYSLSSV VTVPSSSLGT QTYICNVNHK PSNTKVDKKV EPKSCDKTHT    240
```

```
CPPCPAPEAA GAPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR EEMTKNQVSL TCLVKGFYPS DIAVEWESNG QPENNYKTTP PVLDSDGSFF  420
LYSKLTVDKS RWQQGNVFSC SVLHEALHSH YTQKSLSLSP GK                    462
```